US011649249B2

(12) United States Patent
Parham et al.

(10) Patent No.: US 11,649,249 B2
(45) Date of Patent: May 16, 2023

(54) COMPOUNDS FOR ELECTRONIC DEVICES

(71) Applicant: Merck Patent GmbH, Darmstadt (DE)

(72) Inventors: Amir Parham, Frankfurt am Main (DE); Jonas Kroeber, Frankfurt am Main (DE); Dominik Joosten, Ober-Ramstadt (DE); Aurélie Ludemann, Frankfurt am Main (DE); Tobias Grossmann, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 593 days.

(21) Appl. No.: 16/606,784

(22) PCT Filed: Apr. 24, 2018

(86) PCT No.: PCT/EP2018/060405
§ 371 (c)(1),
(2) Date: Oct. 21, 2019

(87) PCT Pub. No.: WO2018/197447
PCT Pub. Date: Nov. 1, 2018

(65) Prior Publication Data
US 2020/0199154 A1    Jun. 25, 2020

(30) Foreign Application Priority Data

Apr. 25, 2017  (EP) .................................... 17168075

(51) Int. Cl.
| | | |
|---|---|---|
| C07D 513/16 | (2006.01) | |
| C07D 498/16 | (2006.01) | |
| C07D 519/00 | (2006.01) | |
| C07D 498/04 | (2006.01) | |
| C07D 513/04 | (2006.01) | |
| H01L 51/00 | (2006.01) | |

(52) U.S. Cl.
CPC ......... *C07D 513/16* (2013.01); *C07D 498/04* (2013.01); *C07D 498/16* (2013.01); *C07D 513/04* (2013.01); *C07D 519/00* (2013.01); *H01L 51/0067* (2013.01); *H01L 51/0068* (2013.01); *H01L 51/0072* (2013.01); *H01L 51/0073* (2013.01)

(58) Field of Classification Search
None
See application file for complete search history.

(56) References Cited

U.S. PATENT DOCUMENTS

| | | | |
|---|---|---|---|
| 8,932,731 B2 | 1/2015 | Parhan et al. | |
| 10,008,673 B2 | 6/2018 | Brocke et al. | |
| 2009/0295275 A1 | 12/2009 | Parham et al. | |
| 2012/0319052 A1 | 12/2012 | Brocke et al. | |
| 2013/0313532 A1 | 11/2013 | Watanabe et al. | |
| 2014/0225083 A1 | 8/2014 | Kim et al. | |
| 2015/0322198 A1* | 11/2015 | Hayer ................. | H01L 51/0036 558/290 |
| 2016/0099416 A1 | 4/2016 | Itoi | |
| 2016/0293853 A1 | 10/2016 | Zeng et al. | |
| 2017/0174705 A1 | 6/2017 | Kato et al. | |
| 2017/0183360 A1 | 6/2017 | Ishii et al. | |

FOREIGN PATENT DOCUMENTS

| | | |
|---|---|---|
| CN | 102782894 A | 11/2012 |
| CN | 109963859 A | 7/2019 |
| EP | 3133661 A1 | 2/2017 |
| EP | 3184522 A1 | 6/2017 |
| JP | 2013-243299 A | 12/2013 |
| JP | 2016-162982 A | 9/2016 |
| KR | 10-2017-0074811 A | 6/2017 |
| KR | 10-2017-0077781 A | 7/2017 |
| KR | 10-2019-0085070 A | 7/2019 |
| WO | WO-2007031165 A2 | 3/2007 |
| WO | WO-2011107186 A2 | 9/2011 |
| WO | 2016/194717 A1 | 12/2016 |
| WO | 2018/095839 A2 | 5/2018 |

OTHER PUBLICATIONS

International Search Report for PCT/EP2018/060405 dated Aug. 21, 2018.
Written Opinion of the International Searching Authority for PCT/EP2018/060405 dated Aug. 21, 2018.

* cited by examiner

*Primary Examiner* — Jay Yang
(74) *Attorney, Agent, or Firm* — Faegre Drinker Biddle & Reath LLP

(57) ABSTRACT

The present application relates to bridged triarylamines conforming to a defined formula. These compounds are suitable for use in electronic devices. The present application further relates to processes for preparing the compounds, and to electronic devices comprising the compounds.

18 Claims, No Drawings

COMPOUNDS FOR ELECTRONIC DEVICES

CROSS-REFERENCE TO RELATED APPLICATIONS

This application is a national stage application (under 35 U.S.C. § 371) of PCT/EP2018/060405, filed Apr. 24, 2018, which claims benefit of European Application No. 17168075.4, filed Apr. 25, 2017, both of which are incorporated herein by reference in their entirety.

The present application relates to bridged triarylamines of a formula (I) defined further down that are substituted by a carbazole derivative. The compounds are suitable for use in electronic devices. The present application further relates to processes for preparing the compounds mentioned, and to electronic devices comprising the compounds mentioned.

Electronic devices in the context of this application are understood to mean what are called organic electronic devices, which contain organic semiconductor materials as functional materials. More particularly, these are understood to mean OLEDs (organic electroluminescent devices). The term OLEDs is understood to mean electronic devices which have one or more layers comprising organic compounds and emit light on application of electrical voltage. The construction and general principle of function of OLEDs are known to those skilled in the art.

In electronic devices, especially OLEDs, there is great interest in improving the performance data, especially lifetime, efficiency and operating voltage. In these aspects, it has not yet been possible to find any entirely satisfactory solution.

A great influence on the performance data of electronic devices is possessed by emission layers comprising phosphorescent emitters and layers having an electron-transporting function. For use in these layers, there is still a search for new materials, especially materials having hole-transporting and electron-transporting properties.

Among the materials disclosed in the prior art for use as matrix materials in emission layers comprising phosphorescent emitters are lactam derivatives, triazine derivatives and triarylamine derivatives. Known materials for electron-transporting layers are especially compounds that bear one or more electron-deficient heteroaryl groups, especially one or more groups selected from triazine groups, pyrimidine groups and quinoline groups.

However, there is still a need for alternative compounds suitable for use in electronic devices.

There is additionally also a need for improvement with regard to the performance data of the compounds in use in electronic devices, especially with regard to lifetime, operating voltage and efficiency.

It has been found that particular bridged triarylamine compounds that bear a carbazole derivative as substituent are of excellent suitability for use in electronic devices, especially for use in OLEDs, even more especially for use therein as matrix materials for phosphorescent emitters or as materials in an electron-transporting layer.

The compounds found show one or more, preferably more than one, of the following advantageous technical effects:
- when used in OLEDs they lead to high efficiency of the OLEDs
- when used in OLEDs they lead to a long lifetime of the OLEDs
- when used in OLEDs they lead to a low operating voltage of the OLEDs
- they have very good processability.

The present application thus provides compounds of formula (I)

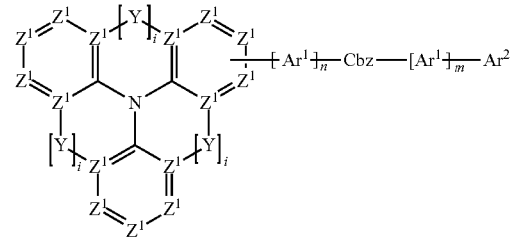

Formula (I)

where the variables that occur are as follows:

Y is the same or different at each instance and is selected from a single bond, O and S, where there is at least one Y group selected from O and S;

$Z^1$ is the same or different at each instance and is $CR^1$, N or C, where a $Z^1$ group is C in the specific case when a Y group is bonded to it;

$Ar^1$ is the same or different at each instance and is an aromatic ring system which has 6 to 24 aromatic ring atoms and may be substituted by one or more $R^2$ radicals, or a heteroaromatic ring system which has 5 to 24 aromatic ring atoms and may be substituted by one or more $R^2$ radicals;

Cbz is a divalent group substituted at each of its unoccupied positions by an $R^3$ radical, and containing one or more structural elements of the formula (Cbz)

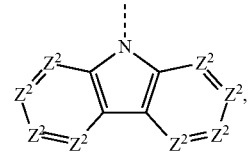

Formula (Cbz)

where one of the two bonds of the divalent group to the rest of the compound is the dotted bond on the nitrogen atom of the formula (Cbz),
where the second of these two bonds may be at any unoccupied position in the group, and where $Z^2$ is the same or different at each instance and is selected from C and N;

$Ar^2$ is an electron-deficient heteroaryl group which has 5 to 30 aromatic ring atoms and may be substituted by one or more $R^4$ radicals;

$R^1$, $R^2$, $R^3$, $R^4$ are the same or different at each instance and are selected from H, D, F, $C(=O)R^5$, CN, $Si(R^5)_3$, $N(R^5)_2$, $P(=O)(R^5)_2$, $OR^5$, $S(=O)R^5$, $S(=O)_2R^5$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$ or $R^2$ or $R^3$ or $R^4$ radicals may be joined to one another and may form a ring; where the alkyl, alkoxy, alkenyl and alkynyl groups mentioned and the aromatic ring systems and heteroaromatic ring systems mentioned may each be substituted by one or more $R^5$ radicals; and where one or more $CH_2$ groups in the alkyl, alkoxy, alkenyl and alkynyl groups mentioned may be replaced by —R$^5$C=CR$^5$—, —C≡C—, Si(R$^5$)$_2$, C=O, C=NR$^5$, —C(=O)O—, —C(=O)NR$^5$—, NR$^5$, P(=O)(R$^5$), —O—, —S—, SO or SO$_2$;

R$^5$ is the same or different at each instance and is selected from H, D, F, C(=O)R$^6$, CN, Si(R$^6$)$_3$, N(R$^6$)$_2$, P(=O)(R$^6$)$_2$, OR$^6$, S(=O)R$^6$, S(=O)$_2$R$^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R$^5$ radicals may be joined to one another and may form a ring; where the alkyl, alkoxy, alkenyl and alkynyl groups mentioned and the aromatic ring systems and heteroaromatic ring systems mentioned may each be substituted by one or more R$^6$ radicals; and where one or more CH$_2$ groups in the alkyl, alkoxy, alkenyl and alkynyl groups mentioned may be replaced by —R$^6$C=CR$^6$—, —C≡C—, Si(R$^6$)$_2$, C=O, C=NR$^6$, —C(=O)O—, —C(=O)NR$^6$—, NR$^6$, P(=O)(R$^6$), —O—, —S—, SO or SO$_2$;

R$^6$ is the same or different at each instance and is selected from H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more R$^6$ radicals may be joined to one another and may form a ring; and where the alkyl, alkoxy, alkenyl and alkynyl groups, aromatic ring systems and heteroaromatic ring systems mentioned may be substituted by F or CN;

i is the same or different at each instance and is 0 or 1, where at least two indices i in formula (I) are 1, and where the Y group in question is absent when the corresponding index i=0;

n is 0, 1, 2, 3 or 4;

m is 0, 1, 2, 3 or 4.

The embodiment in which n=2 is understood to mean that two Ar$^1$ groups are bonded in succession, resulting in a structure

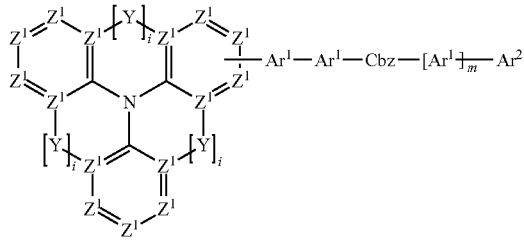

The same applies to embodiments with n=3 and n=4, such that there are then respectively three and four Ar$^1$ groups bonded in succession.

The same applies to embodiments with m=2 and m=3 and m=4.

When n=0 and m=0, the Ar$^1$ group in question is absent, and so the groups that bind to this Ar$^1$ group are bonded directly to one another.

An aryl group in the context of this invention contains 6 to 40 aromatic ring atoms of which none is a heteroatom. An aryl group in the context of this invention is understood to mean either a simple aromatic cycle, i.e. benzene, or a fused aromatic polycycle, for example naphthalene, phenanthrene or anthracene. A fused aromatic polycycle in the context of the present application consists of two or more simple aromatic cycles fused to one another. Fusion between cycles is understood here to mean that the cycles share at least one edge with one another.

A heteroaryl group in the context of this invention contains 5 to 40 aromatic ring atoms of which at least one is a heteroatom. The heteroatoms of the heteroaryl group are preferably selected from N, O and S. A heteroaryl group in the context of this invention is either a simple heteroaromatic cycle, for example pyridine, pyrimidine or thiophene, or a fused heteroaromatic polycycle, for example quinoline or carbazole. A fused heteroaromatic polycycle in the context of the present application consists of two or more simple heteroaromatic cycles fused to one another. Fusion between cycles is understood here to mean that the cycles share at least one edge with one another.

An aryl or heteroaryl group, each of which may be substituted by the abovementioned radicals and which may be joined to the aromatic or heteroaromatic system via any desired positions, is especially understood to mean groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the context of this invention contains 6 to 40 carbon atoms in the ring system and does not include any heteroatoms as aromatic ring atoms. An aromatic ring system in the context of this invention therefore does not contain any heteroaryl groups. An aromatic ring system in the context of this invention shall be understood to mean a system which does not necessarily contain only aryl groups but in which it is also possible for a plurality of aryl groups to be bonded by a single bond or by a non-aromatic unit, for example one or more optionally substituted C, Si, N, O or S atoms. In this case, the non-aromatic unit comprises preferably less than 10% of the atoms other than H, based on the total number of atoms other than H in the system. For example, systems such as 9,9'-spirobifluorene, 9,9'-diarylfluorene, triarylamine, diaryl ethers and stilbene are also to be regarded as aromatic ring systems in the context of this invention, and likewise systems in which two or more aryl groups are joined, for example, by a linear or cyclic alkyl, alkenyl or alkynyl group or by a silyl group. In addition, systems in which two or more aryl groups are joined to one another via single bonds are also regarded as aromatic ring systems in the context of this invention, for example systems such as biphenyl and terphenyl.

A heteroaromatic ring system in the context of this invention contains 5 to 40 aromatic ring atoms, at least one of which is a heteroatom. The heteroatoms of the heteroaromatic ring system are preferably selected from N, O and/or S. A heteroaromatic ring system corresponds to the definition stated above for an aromatic ring system, but has at least one heteroatom as one of the aromatic ring atoms. In this way, it differs from an aromatic ring system in the sense of the definition of the present application, which, according to this definition, cannot contain any heteroatom as aromatic ring atom.

An aromatic ring system having 6 to 40 aromatic ring atoms or a heteroaromatic ring system having 5 to 40 aromatic ring atoms is especially understood to mean groups derived from the groups mentioned above under aryl groups and heteroaryl groups, and from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole, or from combinations of these groups.

In the context of the present invention, a straight-chain alkyl group having 1 to 20 carbon atoms and a branched or cyclic alkyl group having 3 to 20 carbon atoms and an alkenyl or alkynyl group having 2 to 40 carbon atoms in which individual hydrogen atoms or $CH_2$ groups may also be substituted by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals.

An alkoxy or thioalkyl group having 1 to 20 carbon atoms in which individual hydrogen atoms or $CH_2$ groups may also be replaced by the groups mentioned above in the definition of the radicals is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The wording that two or more radicals together may form a ring, in the context of the present application, shall be understood to mean, inter alia, that the two radicals are joined to one another by a chemical bond. In addition, however, the abovementioned wording should also be understood to mean that, if one of the two radicals is hydrogen, the second radical binds to the position to which the hydrogen atom was bonded, forming a ring.

An electron-deficient heteroaryl group as $Ar^2$ group that may be substituted by one or more $R^4$ radicals is especially understood to mean a heteroaryl group which has 5 to 30 aromatic ring atoms and contains at least one heteroaromatic five-membered ring having two or more heteroatoms selected from N, O and S or at least one heteroaromatic six-membered ring having one or more heteroatoms selected from N, O and S.

Preferred embodiments of the electron-deficient heteroaryl group $Ar^2$ conform to one of the following formulae:

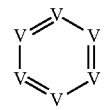

(Ar²-A)

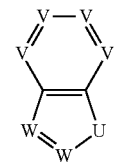

(Ar²-B)

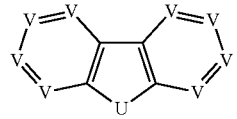

(Ar²-C)

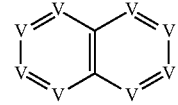

(Ar²-D)

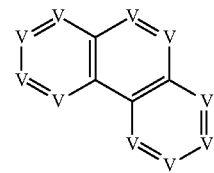

(Ar²-E)

where the variables that occur are defined as follows:

V is the same or different at each instance and is N or $CR^4$, where at least one V group in each of formulae (Ar²-A), (Ar²-C), (Ar²-D) and (Ar²-E) is N;

W is the same or different at each instance and is N or $CR^4$;

U is $NR^4$;

where at least one group selected from W and V groups in formula (Ar²-B) is N; and where one $R^4$ group per formula is replaced by the bond to the $Ar^1$ group or Cbz.

$Ar^2$ is more preferably selected from pyridine, pyrimidine, pyridazine, pyrazine, triazine, azacarbazole, benzimidazole, quinoline, quinazoline, benzo[h]quinazoline, phenanthroline, phenanthridine, diazaphenanthrene, and acridine, each of which may be substituted by one or more $R^4$ radicals. Very particular preference is given to triazine and quinazoline, each of which may be substituted by one or more $R^4$ radicals, very particular preference to triazine and 2-quinazoline, each of which may be substituted by one or more $R^4$ radicals.

Very particularly preferred Ar² groups are selected from groups of the following formulae:
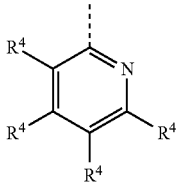
Formula (Ar²-1)
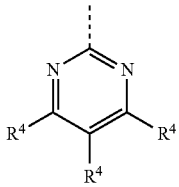
Formula (Ar²-2)
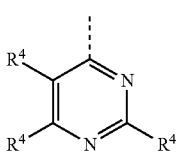
Formula (Ar²-3)
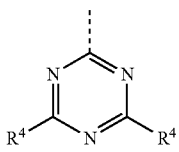
Formula (Ar²-4)
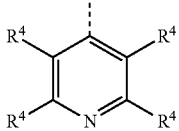
Formula (Ar²-5)
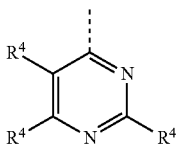
Formula (Ar²-6)
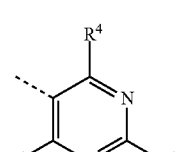
Formula (Ar²-7)
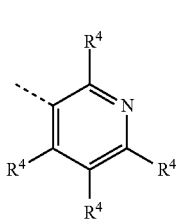
Formula (Ar²-8)
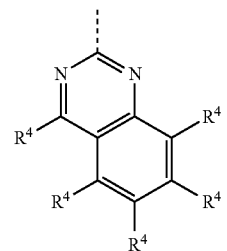
Formula (Ar²-9)
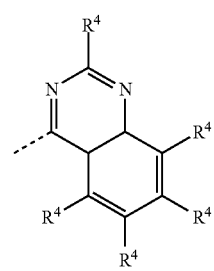
Formula (Ar²-10)
Formula (Ar²-11)
Formula (Ar²-12)
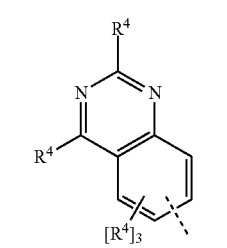
Formula (Ar²-13)
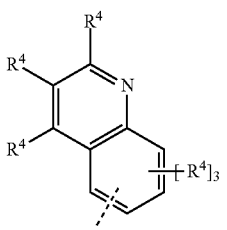
Formula (Ar²-14)

Formula (Ar²-15)
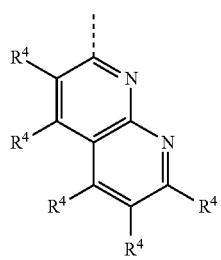

Formula (Ar²-16)
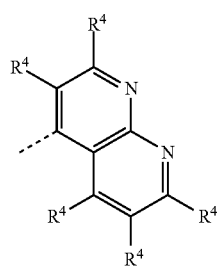

Formula (Ar²-17)
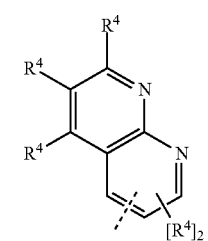

Formula (Ar²-18)
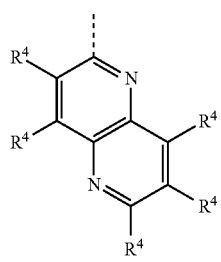

Formula (Ar²-19)
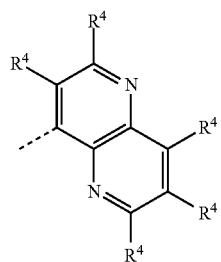

Formula (Ar²-20)
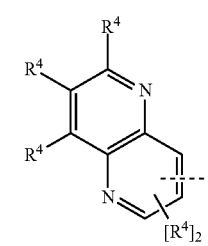

Formula (Ar²-21)
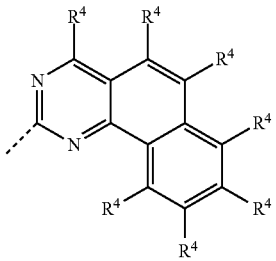

Formula (Ar²-22)
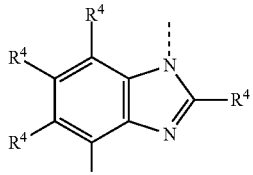

Formula (Ar²-23)
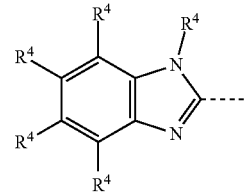

where the dotted bond represents the bond to the Ar¹ or Cbz group.

$R^4$ radicals in the abovementioned formulae are preferably selected from H and aromatic ring systems which have 6 to 12 aromatic ring atoms and may each be substituted by one or more $R^5$ groups.

Among the abovementioned formulae, particular preference is given to the formulae (Ar²-1), (Ar²-2), (Ar²-4), (Ar²-6), (Ar²-7), (Ar²-9) and (Ar²-10).

A divalent group containing one or more structural elements of the formula (Cbz) is understood to mean a group containing i) as well as the structural element of the formula (Cbz) further structural elements bonded to the structural element of the formula (Cbz), and/or containing ii) the structural element of the formula (Cbz) as part of a greater coherent group.

Examples of case ii) are divalent groups of the formulae below:

(Cbz-Ex-1)
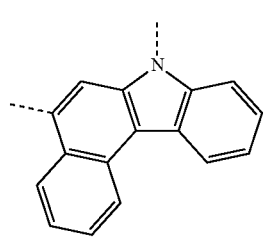

(Cbz-Ex-2)
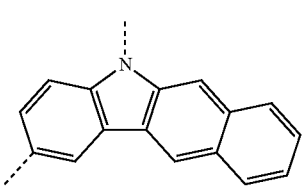

(Cbz-Ex-3)

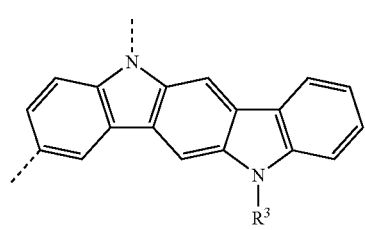

(Cbz-Ex-4)

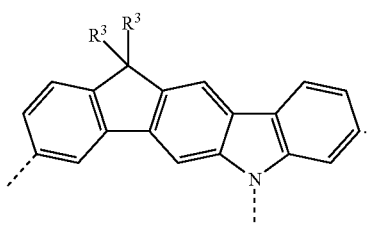

In formula (Cbz), it is preferable that $Z^2$ is C.

Preferred Cbz groups are selected from carbazole, azacarbazole, benzocarbazole, dibenzocarbazole, indenocarbazole, indolocarbazole, carbazole fused to benzofuran and carbazole fused to benzothiophene, where the groups mentioned may each be substituted by one or more $R^3$ radicals.

Preferred Cbz groups conform to the following formulae:

Formula (Cbz-1)

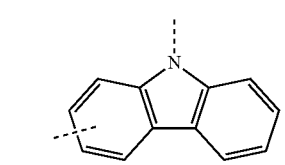

Formula (Cbz-2)

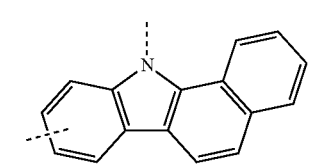

Formula (Cbz-3)

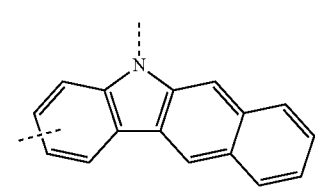

Formula (Cbz-4)

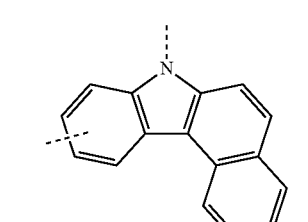

Formula (Cbz-5)

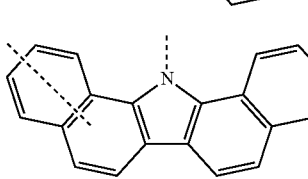

Formula (Cbz-6)

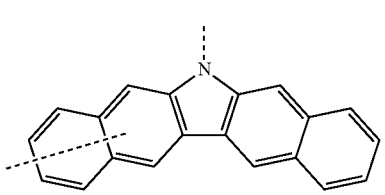

Formula (Cbz-7)

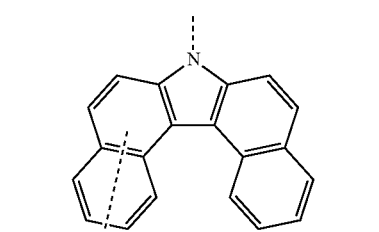

Formula (Cbz-8)

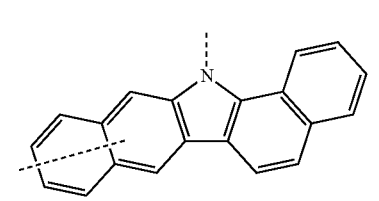

Formula (Cbz-9)

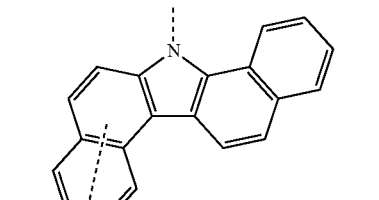

Formula (Cbz-10)

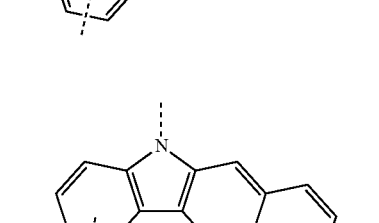

Formula (Cbz-11)

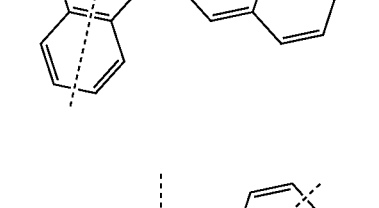

Formula (Cbz-12)

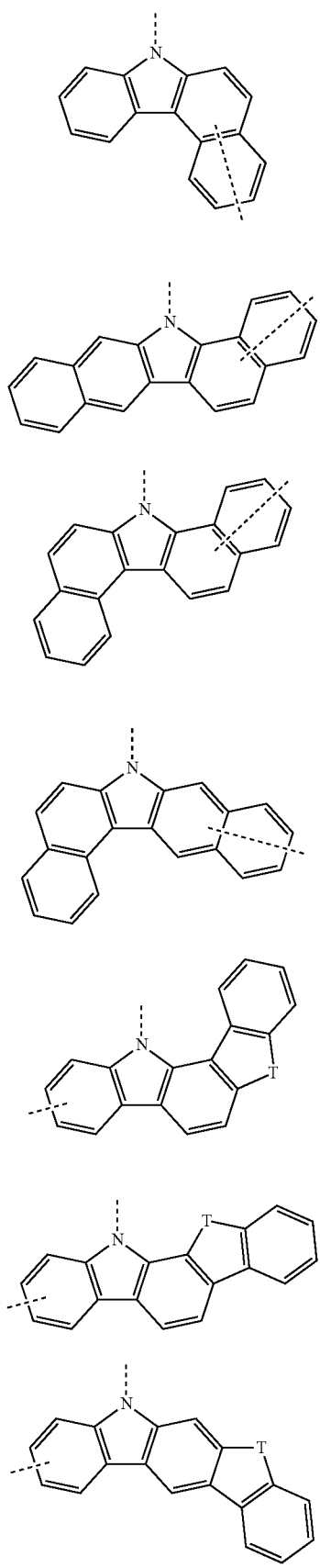

-continued

Formula (Cbz-27)

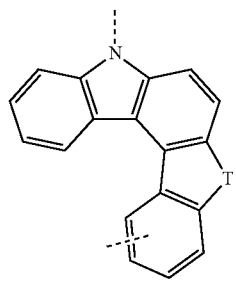

Formula (Cbz-28)

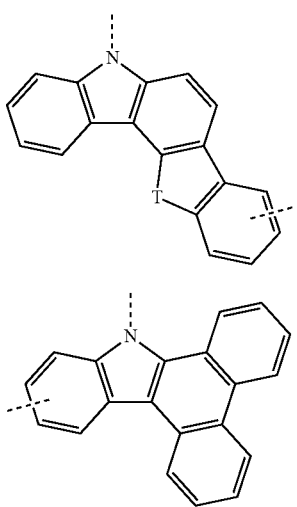

Formula (Cbz-29)

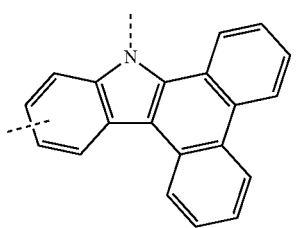

where:
T is C(R$^3$)$_2$, O, S or NR$^3$;
where the dotted bonds represent the bonds to the rest of the compound, and
where the groups in the abovementioned formulae may each be substituted by an R$^3$ radical at any position shown as unsubstituted.

Among the abovementioned formulae, particular preference is given to the formulae (Cbz-1), (Cbz-2), (Cbz-4), (Cbz-18), (Cbz-19), (Cbz-20), (Cbz-22) and (Cbz-29). Very particular preference is given to the formula (Cbz-1).

In the formulae (Cbz-1) to (Cbz-4) and (Cbz-17) to (Cbz-22), it is preferable that that bond to the rest of the compound via the six-membered ring is in the position para to the nitrogen atom.

Preferred embodiments of groups of the formula (Cbz-1) are the groups of the formulae (Cbz-1-1) to (Cbz-1-3) shown hereinafter, more preferably (Cbz-1-2), Formula (Cbz-1-1)

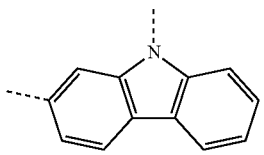

Formula (Cbz-1-2)

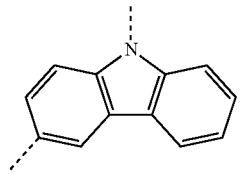

Formula (Cbz-1-3)

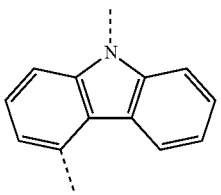

where the dotted bonds represent the bonds to the rest of the compound, and
where the groups in the abovementioned formulae may each be substituted by an R$^3$ radical at any position shown as unsubstituted.

In addition, it is preferable that the groups of the abovementioned formulae do not bear any substituents at the positions shown as unsubstituted.

Preferably, Y is the same at each instance. In addition, it is preferable that Y is the same or different at each instance and is selected from O and S. More preferably, Y is O.

It is preferable that not more than 2 Z$^1$ groups per formula (I) are N. More preferably, Z$^1$ is CR$^1$ or C, where a Z$^1$ group is C in the specific case when a Y group is bonded to it.

Preferably, Ar$^1$ is the same or different at each instance and is a divalent group derived from the base skeletons of benzene, biphenyl, terphenyl, naphthalene, dibenzofuran, dibenzothiophene, carbazole and fluorene, where the divalent group may be substituted by one or more R$^2$ radicals. More preferably, Ar$^1$ is 1,2-phenylene, 1,3-phenylene or 1,4-phenylene, each of which may be substituted by one or more R$^2$ radicals.

Preferably, R$^1$, R$^2$, R$^3$ and R$^4$ are the same or different at each instance and are selected from H, D, F, CN, Si(R$^5$)$_3$, N(R$^5$)$_2$, straight-chain alkyl or alkoxy groups having 1 to 20 carbon atoms, branched or cyclic alkyl or alkoxy groups having 3 to 20 carbon atoms, aromatic ring systems having 6 to 40 aromatic ring atoms and heteroaromatic ring systems having 5 to 40 aromatic ring atoms, where the alkyl and alkoxy groups mentioned, the aromatic ring systems mentioned and the heteroaromatic ring systems mentioned may each be substituted by one or more R$^5$ radicals; and where one or more CH$_2$ groups in the alkyl or alkoxy groups mentioned may be replaced by —C≡C—, —R$^5$C=CR$^5$—, Si(R$^5$)$_2$, C=O, C=NR$^5$, —NR$^5$—, —O—, —S—, —C(=O)O— or —C(=O)NR$^5$—. More preferably, R$^1$, R$^2$, R$^3$ and R$^4$ are the same or different at each instance and are selected from H, F, CN, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where said alkyl groups, said aromatic ring systems and said heteroaromatic ring systems may each be substituted by one or more R$^5$ radicals.

Most preferably, R$^1$ is H. Most preferably in addition, R$^2$ is H. Most preferably in addition, R$^3$ is H. Most preferably in addition, R$^4$ is the same or different at each instance and is selected from H, aromatic ring systems having 6 to 40 aromatic ring atoms, and heteroaromatic ring systems having 5 to 40 aromatic ring atoms.

Preferably, R$^5$ is the same or different at each instance and is selected from H, D, F, CN, Si(R$^6$)$_3$, N(R$^6$)$_2$, straight-chain alkyl or alkoxy groups having 1 to 20 carbon atoms, branched or cyclic alkyl or alkoxy groups having 3 to 20 carbon atoms, aromatic ring systems having 6 to 40 aromatic ring atoms and heteroaromatic ring systems having 5 to 40 aromatic ring atoms; where the alkyl and alkoxy groups mentioned, the aromatic ring systems mentioned and the heteroaromatic ring systems mentioned may each be substituted by one or more $R^6$ radicals; and where one or more $CH_2$ groups in the alkyl or alkoxy groups mentioned may be replaced by —C≡C—, —$R^6$C=C$R^6$—, Si($R^6$)$_2$, C=O, C=N$R^6$, —N$R^6$—, —O—, —S—, —C(=O)O— or —C(=O)N$R^6$—. More preferably, $R^5$ is H.

Preferably, $R^6$ is the same or different at each instance and is selected from H, D, F, CN, alkyl groups having 1 to 20 carbon atoms, aromatic ring systems having 6 to 40 aromatic ring atoms, and heteroaromatic ring systems having 5 to 40 aromatic ring atoms. More preferably, $R^6$ is H.

Preferably, two of the three indices i in formula (I) are 1, and one of the three indices i is 0.

Preferably, m is 0 or 1, more preferably 0.

Preferably, n is 0 or 1, more preferably 0.

Preferred embodiments of the formula (I) correspond to the following formulae (I-1) to (I-24):

Formula (I-1)

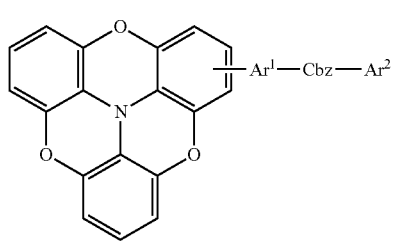

Formula (I-2)

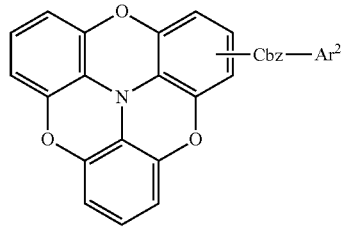

Formula (I-3)

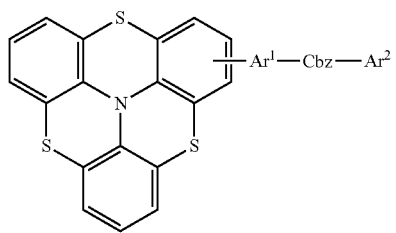

Formula (I-4)

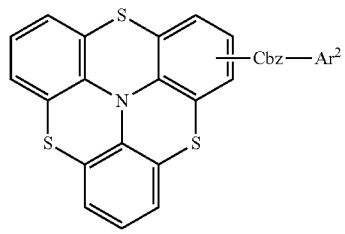

Formula (I-5)

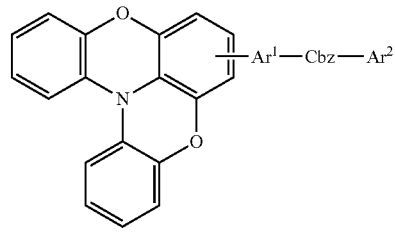

Formula (I-6)

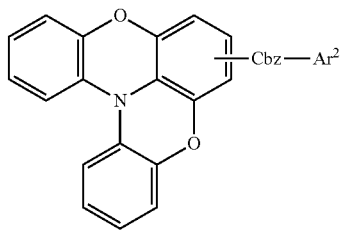

Formula (I-7)

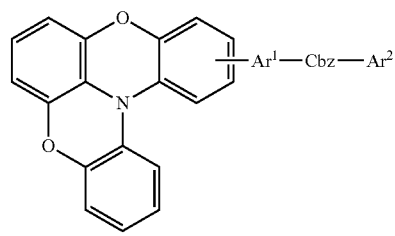

Formula (I-8)

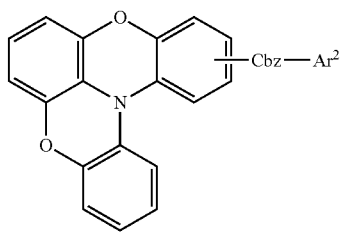

Formula (I-9)

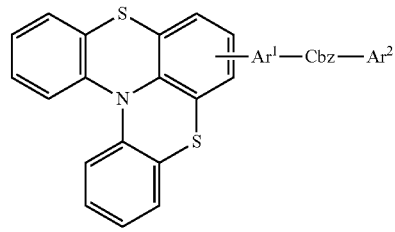

Formula (I-10)

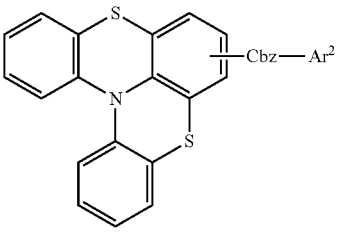

-continued
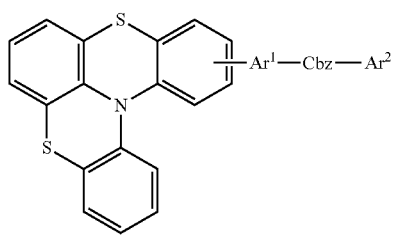
Formula (I-11)
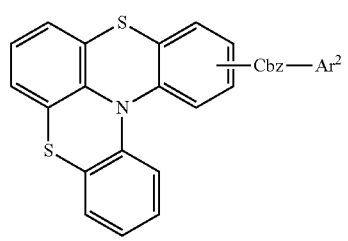
Formula (I-12)
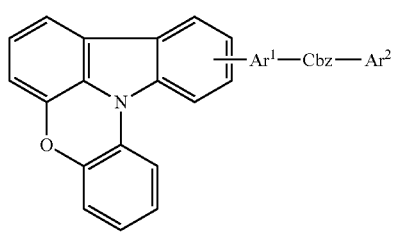
Formula (I-13)
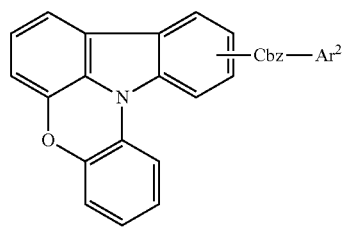
Formula (I-14)
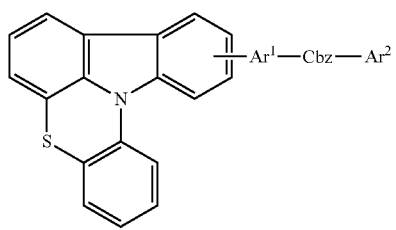
Formula (I-15)
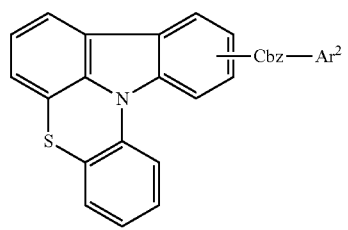
Formula (I-16)
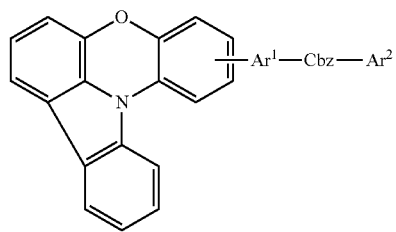
Formula (I-17)
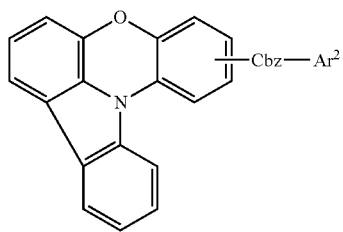
Formula (I-18)
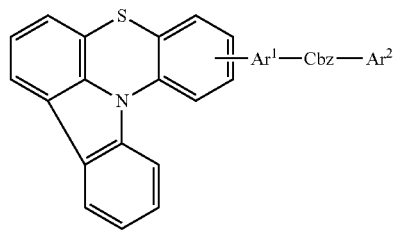
Formula (I-19)
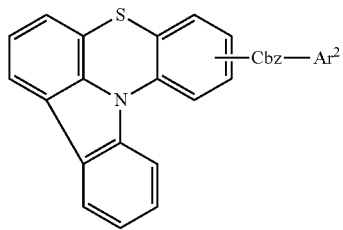
Formula (I-20)
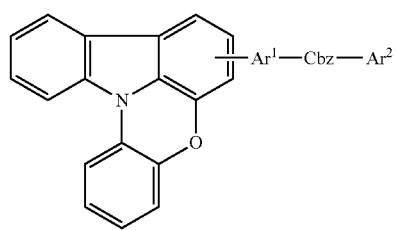
Formula (I-21)
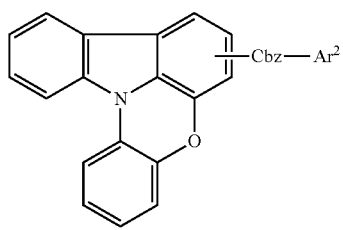
Formula (I-22)

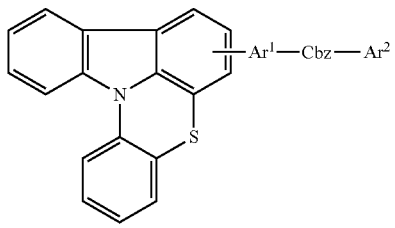

Formula (I-23)

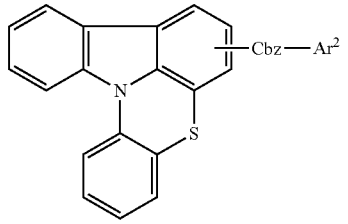

Formula (I-24)

where the variables that occur are as defined above, and the formulae may be substituted at each of the positions shown as unsubstituted on the aromatic six-membered rings by an $R^1$ group.

Preferably, the compounds of the formulae (I-1) to (I-24) are unsubstituted at all positions shown as unsubstituted on the six-membered rings.

In addition, it is preferable that the compound parts -Cbz-$Ar^2$ and —$Ar^1$-Cbz-$Ar^2$ in the formulae (I-1) to (I-24) are each bonded to the aromatic six-membered ring in the position para to the nitrogen atom, as shown by the following example for formula (I-1):

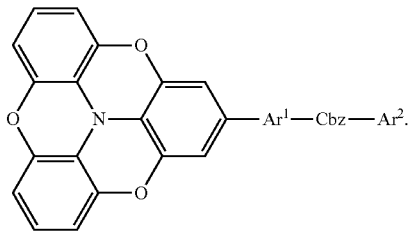

Formula (I-1-a)

For the formulae (I-1) to (I-24), the above generally preferred embodiments of the variables are still applicable.

Especially preferred are the following embodiments of the formulae (I-1) to (I-24) in which the Cbz group conforms to one of the preferred formulae (Cbz-1) to (Cbz-29):

| Formula | Parent structure | Cbz group |
|---|---|---|
| Formula (I-1-1) | Formula (I-1) | Formula (Cbz-1) |
| Formula (I-1-2) | Formula (I-1) | Formula (Cbz-2) |
| Formula (I-1-3) | Formula (I-1) | Formula (Cbz-3) |
| Formula (I-1-4) | Formula (I-1) | Formula (Cbz-4) |
| Formula (I-1-5) | Formula (I-1) | Formula (Cbz-5) |
| Formula (I-1-6) | Formula (I-1) | Formula (Cbz-6) |
| Formula (I-1-7) | Formula (I-1) | Formula (Cbz-7) |
| Formula (I-1-8) | Formula (I-1) | Formula (Cbz-8) |
| Formula (I-1-9) | Formula (I-1) | Formula (Cbz-9) |
| Formula (I-1-10) | Formula (I-1) | Formula (Cbz-10) |
| Formula (I-1-11) | Formula (I-1) | Formula (Cbz-11) |
| Formula (I-1-12) | Formula (I-1) | Formula (Cbz-12) |
| Formula (I-1-13) | Formula (I-1) | Formula (Cbz-13) |
| Formula (I-1-14) | Formula (I-1) | Formula (Cbz-14) |
| Formula (I-1-15) | Formula (I-1) | Formula (Cbz-15) |
| Formula (I-1-16) | Formula (I-1) | Formula (Cbz-16) |
| Formula (I-1-17) | Formula (I-1) | Formula (Cbz-17) |
| Formula (I-1-18) | Formula (I-1) | Formula (Cbz-18) |
| Formula (I-1-19) | Formula (I-1) | Formula (Cbz-19) |
| Formula (I-1-20) | Formula (I-1) | Formula (Cbz-20) |
| Formula (I-1-21) | Formula (I-1) | Formula (Cbz-21) |
| Formula (I-1-22) | Formula (I-1) | Formula (Cbz-22) |
| Formula (I-1-23) | Formula (I-1) | Formula (Cbz-23) |
| Formula (I-1-24) | Formula (I-1) | Formula (Cbz-24) |
| Formula (I-1-25) | Formula (I-1) | Formula (Cbz-25) |
| Formula (I-1-26) | Formula (I-1) | Formula (Cbz-26) |
| Formula (I-1-27) | Formula (I-1) | Formula (Cbz-27) |
| Formula (I-1-28) | Formula (I-1) | Formula (Cbz-28) |
| Formula (I-1-29) | Formula (I-1) | Formula (Cbz-29) |
| Formula (I-2-1) | Formula (I-2) | Formula (Cbz-1) |
| Formula (I-2-2) | Formula (I-2) | Formula (Cbz-2) |
| Formula (I-2-3) | Formula (I-2) | Formula (Cbz-3) |
| Formula (I-2-4) | Formula (I-2) | Formula (Cbz-4) |
| Formula (I-2-5) | Formula (I-2) | Formula (Cbz-5) |
| Formula (I-2-6) | Formula (I-2) | Formula (Cbz-6) |
| Formula (I-2-7) | Formula (I-2) | Formula (Cbz-7) |
| Formula (I-2-8) | Formula (I-2) | Formula (Cbz-8) |
| Formula (I-2-9) | Formula (I-2) | Formula (Cbz-9) |
| Formula (I-2-10) | Formula (I-2) | Formula (Cbz-10) |
| Formula (I-2-11) | Formula (I-2) | Formula (Cbz-11) |
| Formula (I-2-12) | Formula (I-2) | Formula (Cbz-12) |
| Formula (I-2-13) | Formula (I-2) | Formula (Cbz-13) |
| Formula (I-2-14) | Formula (I-2) | Formula (Cbz-14) |
| Formula (I-2-15) | Formula (I-2) | Formula (Cbz-15) |
| Formula (I-2-16) | Formula (I-2) | Formula (Cbz-16) |
| Formula (I-2-17) | Formula (I-2) | Formula (Cbz-17) |
| Formula (I-2-18) | Formula (I-2) | Formula (Cbz-18) |
| Formula (I-2-19) | Formula (I-2) | Formula (Cbz-19) |
| Formula (I-2-20) | Formula (I-2) | Formula (Cbz-20) |
| Formula (I-2-21) | Formula (I-2) | Formula (Cbz-21) |
| Formula (I-2-22) | Formula (I-2) | Formula (Cbz-22) |
| Formula (I-2-23) | Formula (I-2) | Formula (Cbz-23) |
| Formula (I-2-24) | Formula (I-2) | Formula (Cbz-24) |
| Formula (I-2-25) | Formula (I-2) | Formula (Cbz-25) |
| Formula (I-2-26) | Formula (I-2) | Formula (Cbz-26) |
| Formula (I-2-27) | Formula (I-2) | Formula (Cbz-27) |
| Formula (I-2-28) | Formula (I-2) | Formula (Cbz-28) |
| Formula (I-2-29) | Formula (I-2) | Formula (Cbz-29) |
| Formula (I-3-1) | Formula (I-3) | Formula (Cbz-1) |
| Formula (I-3-2) | Formula (I-3) | Formula (Cbz-2) |
| Formula (I-3-3) | Formula (I-3) | Formula (Cbz-3) |
| Formula (I-3-4) | Formula (I-3) | Formula (Cbz-4) |
| Formula (I-3-5) | Formula (I-3) | Formula (Cbz-5) |
| Formula (I-3-6) | Formula (I-3) | Formula (Cbz-6) |
| Formula (I-3-7) | Formula (I-3) | Formula (Cbz-7) |
| Formula (I-3-8) | Formula (I-3) | Formula (Cbz-8) |
| Formula (I-3-9) | Formula (I-3) | Formula (Cbz-9) |
| Formula (I-3-10) | Formula (I-3) | Formula (Cbz-10) |
| Formula (I-3-11) | Formula (I-3) | Formula (Cbz-11) |
| Formula (I-3-12) | Formula (I-3) | Formula (Cbz-12) |
| Formula (I-3-13) | Formula (I-3) | Formula (Cbz-13) |
| Formula (I-3-14) | Formula (I-3) | Formula (Cbz-14) |
| Formula (I-3-15) | Formula (I-3) | Formula (Cbz-15) |
| Formula (I-3-16) | Formula (I-3) | Formula (Cbz-16) |
| Formula (I-3-17) | Formula (I-3) | Formula (Cbz-17) |
| Formula (I-3-18) | Formula (I-3) | Formula (Cbz-18) |
| Formula (I-3-19) | Formula (I-3) | Formula (Cbz-19) |
| Formula (I-3-20) | Formula (I-3) | Formula (Cbz-20) |
| Formula (I-3-21) | Formula (I-3) | Formula (Cbz-21) |
| Formula (I-3-22) | Formula (I-3) | Formula (Cbz-22) |
| Formula (I-3-23) | Formula (I-3) | Formula (Cbz-23) |
| Formula (I-3-24) | Formula (I-3) | Formula (Cbz-24) |
| Formula (I-3-25) | Formula (I-3) | Formula (Cbz-25) |
| Formula (I-3-26) | Formula (I-3) | Formula (Cbz-26) |
| Formula (I-3-27) | Formula (I-3) | Formula (Cbz-27) |
| Formula (I-3-28) | Formula (I-3) | Formula (Cbz-28) |
| Formula (I-3-29) | Formula (I-3) | Formula (Cbz-29) |
| Formula (I-4-1) | Formula (I-4) | Formula (Cbz-1) |
| Formula (I-4-2) | Formula (I-4) | Formula (Cbz-2) |
| Formula (I-4-3) | Formula (I-4) | Formula (Cbz-3) |
| Formula (I-4-4) | Formula (I-4) | Formula (Cbz-4) |

-continued

| Formula | Parent structure | Cbz group |
|---|---|---|
| Formula (I-4-5) | Formula (I-4) | Formula (Cbz-5) |
| Formula (I-4-6) | Formula (I-4) | Formula (Cbz-6) |
| Formula (I-4-7) | Formula (I-4) | Formula (Cbz-7) |
| Formula (I-4-8) | Formula (I-4) | Formula (Cbz-8) |
| Formula (I-4-9) | Formula (I-4) | Formula (Cbz-9) |
| Formula (I-4-10) | Formula (I-4) | Formula (Cbz-10) |
| Formula (I-4-11) | Formula (I-4) | Formula (Cbz-11) |
| Formula (I-4-12) | Formula (I-4) | Formula (Cbz-12) |
| Formula (I-4-13) | Formula (I-4) | Formula (Cbz-13) |
| Formula (I-4-14) | Formula (I-4) | Formula (Cbz-14) |
| Formula (I-4-15) | Formula (I-4) | Formula (Cbz-15) |
| Formula (I-4-16) | Formula (I-4) | Formula (Cbz-16) |
| Formula (I-4-17) | Formula (I-4) | Formula (Cbz-17) |
| Formula (I-4-18) | Formula (I-4) | Formula (Cbz-18) |
| Formula (I-4-19) | Formula (I-4) | Formula (Cbz-19) |
| Formula (I-4-20) | Formula (I-4) | Formula (Cbz-20) |
| Formula (I-4-21) | Formula (I-4) | Formula (Cbz-21) |
| Formula (I-4-22) | Formula (I-4) | Formula (Cbz-22) |
| Formula (I-4-23) | Formula (I-4) | Formula (Cbz-23) |
| Formula (I-4-24) | Formula (I-4) | Formula (Cbz-24) |
| Formula (I-4-25) | Formula (I-4) | Formula (Cbz-25) |
| Formula (I-4-26) | Formula (I-4) | Formula (Cbz-26) |
| Formula (I-4-27) | Formula (I-4) | Formula (Cbz-27) |
| Formula (I-4-28) | Formula (I-4) | Formula (Cbz-28) |
| Formula (I-4-29) | Formula (I-4) | Formula (Cbz-29) |
| Formula (I-5-1) | Formula (I-5) | Formula (Cbz-1) |
| Formula (I-5-2) | Formula (I-5) | Formula (Cbz-2) |
| Formula (I-5-3) | Formula (I-5) | Formula (Cbz-3) |
| Formula (I-5-4) | Formula (I-5) | Formula (Cbz-4) |
| Formula (I-5-5) | Formula (I-5) | Formula (Cbz-5) |
| Formula (I-5-6) | Formula (I-5) | Formula (Cbz-6) |
| Formula (I-5-7) | Formula (I-5) | Formula (Cbz-7) |
| Formula (I-5-8) | Formula (I-5) | Formula (Cbz-8) |
| Formula (I-5-9) | Formula (I-5) | Formula (Cbz-9) |
| Formula (I-5-10) | Formula (I-5) | Formula (Cbz-10) |
| Formula (I-5-11) | Formula (I-5) | Formula (Cbz-11) |
| Formula (I-5-12) | Formula (I-5) | Formula (Cbz-12) |
| Formula (I-5-13) | Formula (I-5) | Formula (Cbz-13) |
| Formula (I-5-14) | Formula (I-5) | Formula (Cbz-14) |
| Formula (I-5-15) | Formula (I-5) | Formula (Cbz-15) |
| Formula (I-5-16) | Formula (I-5) | Formula (Cbz-16) |
| Formula (I-5-17) | Formula (I-5) | Formula (Cbz-17) |
| Formula (I-5-18) | Formula (I-5) | Formula (Cbz-18) |
| Formula (I-5-19) | Formula (I-5) | Formula (Cbz-19) |
| Formula (I-5-20) | Formula (I-5) | Formula (Cbz-20) |
| Formula (I-5-21) | Formula (I-5) | Formula (Cbz-21) |
| Formula (I-5-22) | Formula (I-5) | Formula (Cbz-22) |
| Formula (I-5-23) | Formula (I-5) | Formula (Cbz-23) |
| Formula (I-5-24) | Formula (I-5) | Formula (Cbz-24) |
| Formula (I-5-25) | Formula (I-5) | Formula (Cbz-25) |
| Formula (I-5-26) | Formula (I-5) | Formula (Cbz-26) |
| Formula (I-5-27) | Formula (I-5) | Formula (Cbz-27) |
| Formula (I-5-28) | Formula (I-5) | Formula (Cbz-28) |
| Formula (I-5-29) | Formula (I-5) | Formula (Cbz-29) |
| Formula (I-6-1) | Formula (I-6) | Formula (Cbz-1) |
| Formula (I-6-2) | Formula (I-6) | Formula (Cbz-2) |
| Formula (I-6-3) | Formula (I-6) | Formula (Cbz-3) |
| Formula (I-6-4) | Formula (I-6) | Formula (Cbz-4) |
| Formula (I-6-5) | Formula (I-6) | Formula (Cbz-5) |
| Formula (I-6-6) | Formula (I-6) | Formula (Cbz-6) |
| Formula (I-6-7) | Formula (I-6) | Formula (Cbz-7) |
| Formula (I-6-8) | Formula (I-6) | Formula (Cbz-8) |
| Formula (I-6-9) | Formula (I-6) | Formula (Cbz-9) |
| Formula (I-6-10) | Formula (I-6) | Formula (Cbz-10) |
| Formula (I-6-11) | Formula (I-6) | Formula (Cbz-11) |
| Formula (I-6-12) | Formula (I-6) | Formula (Cbz-12) |
| Formula (I-6-13) | Formula (I-6) | Formula (Cbz-13) |
| Formula (I-6-14) | Formula (I-6) | Formula (Cbz-14) |
| Formula (I-6-15) | Formula (I-6) | Formula (Cbz-15) |
| Formula (I-6-16) | Formula (I-6) | Formula (Cbz-16) |
| Formula (I-6-17) | Formula (I-6) | Formula (Cbz-17) |
| Formula (I-6-18) | Formula (I-6) | Formula (Cbz-18) |
| Formula (I-6-19) | Formula (I-6) | Formula (Cbz-19) |
| Formula (I-6-20) | Formula (I-6) | Formula (Cbz-20) |
| Formula (I-6-21) | Formula (I-6) | Formula (Cbz-21) |
| Formula (I-6-22) | Formula (I-6) | Formula (Cbz-22) |
| Formula (I-6-23) | Formula (I-6) | Formula (Cbz-23) |
| Formula (I-6-24) | Formula (I-6) | Formula (Cbz-24) |
| Formula (I-6-25) | Formula (I-6) | Formula (Cbz-25) |
| Formula (I-6-26) | Formula (I-6) | Formula (Cbz-26) |
| Formula (I-6-27) | Formula (I-6) | Formula (Cbz-27) |
| Formula (I-6-28) | Formula (I-6) | Formula (Cbz-28) |
| Formula (I-6-29) | Formula (I-6) | Formula (Cbz-29) |
| Formula (I-7-1) | Formula (I-7) | Formula (Cbz-1) |
| Formula (I-7-2) | Formula (I-7) | Formula (Cbz-2) |
| Formula (I-7-3) | Formula (I-7) | Formula (Cbz-3) |
| Formula (I-7-4) | Formula (I-7) | Formula (Cbz-4) |
| Formula (I-7-5) | Formula (I-7) | Formula (Cbz-5) |
| Formula (I-7-6) | Formula (I-7) | Formula (Cbz-6) |
| Formula (I-7-7) | Formula (I-7) | Formula (Cbz-7) |
| Formula (I-7-8) | Formula (I-7) | Formula (Cbz-8) |
| Formula (I-7-9) | Formula (I-7) | Formula (Cbz-9) |
| Formula (I-7-10) | Formula (I-7) | Formula (Cbz-10) |
| Formula (I-7-11) | Formula (I-7) | Formula (Cbz-11) |
| Formula (I-7-12) | Formula (I-7) | Formula (Cbz-12) |
| Formula (I-7-13) | Formula (I-7) | Formula (Cbz-13) |
| Formula (I-7-14) | Formula (I-7) | Formula (Cbz-14) |
| Formula (I-7-15) | Formula (I-7) | Formula (Cbz-15) |
| Formula (I-7-16) | Formula (I-7) | Formula (Cbz-16) |
| Formula (I-7-17) | Formula (I-7) | Formula (Cbz-17) |
| Formula (I-7-18) | Formula (I-7) | Formula (Cbz-18) |
| Formula (I-7-19) | Formula (I-7) | Formula (Cbz-19) |
| Formula (I-7-20) | Formula (I-7) | Formula (Cbz-20) |
| Formula (I-7-21) | Formula (I-7) | Formula (Cbz-21) |
| Formula (I-7-22) | Formula (I-7) | Formula (Cbz-22) |
| Formula (I-7-23) | Formula (I-7) | Formula (Cbz-23) |
| Formula (I-7-24) | Formula (I-7) | Formula (Cbz-24) |
| Formula (I-7-25) | Formula (I-7) | Formula (Cbz-25) |
| Formula (I-7-26) | Formula (I-7) | Formula (Cbz-26) |
| Formula (I-7-27) | Formula (I-7) | Formula (Cbz-27) |
| Formula (I-7-28) | Formula (I-7) | Formula (Cbz-28) |
| Formula (I-7-29) | Formula (I-7) | Formula (Cbz-29) |
| Formula (I-8-1) | Formula (I-8) | Formula (Cbz-1) |
| Formula (I-8-2) | Formula (I-8) | Formula (Cbz-2) |
| Formula (I-8-3) | Formula (I-8) | Formula (Cbz-3) |
| Formula (I-8-4) | Formula (I-8) | Formula (Cbz-4) |
| Formula (I-8-5) | Formula (I-8) | Formula (Cbz-5) |
| Formula (I-8-6) | Formula (I-8) | Formula (Cbz-6) |
| Formula (I-8-7) | Formula (I-8) | Formula (Cbz-7) |
| Formula (I-8-8) | Formula (I-8) | Formula (Cbz-8) |
| Formula (I-8-9) | Formula (I-8) | Formula (Cbz-9) |
| Formula (I-8-10) | Formula (I-8) | Formula (Cbz-10) |
| Formula (I-8-11) | Formula (I-8) | Formula (Cbz-11) |
| Formula (I-8-12) | Formula (I-8) | Formula (Cbz-12) |
| Formula (I-8-13) | Formula (I-8) | Formula (Cbz-13) |
| Formula (I-8-14) | Formula (I-8) | Formula (Cbz-14) |
| Formula (I-8-15) | Formula (I-8) | Formula (Cbz-15) |
| Formula (I-8-16) | Formula (I-8) | Formula (Cbz-16) |
| Formula (I-8-17) | Formula (I-8) | Formula (Cbz-17) |
| Formula (I-8-18) | Formula (I-8) | Formula (Cbz-18) |
| Formula (I-8-19) | Formula (I-8) | Formula (Cbz-19) |
| Formula (I-8-20) | Formula (I-8) | Formula (Cbz-20) |
| Formula (I-8-21) | Formula (I-8) | Formula (Cbz-21) |
| Formula (I-8-22) | Formula (I-8) | Formula (Cbz-22) |
| Formula (I-8-23) | Formula (I-8) | Formula (Cbz-23) |
| Formula (I-8-24) | Formula (I-8) | Formula (Cbz-24) |
| Formula (I-8-25) | Formula (I-8) | Formula (Cbz-25) |
| Formula (I-8-26) | Formula (I-8) | Formula (Cbz-26) |
| Formula (I-8-27) | Formula (I-8) | Formula (Cbz-27) |
| Formula (I-8-28) | Formula (I-8) | Formula (Cbz-28) |
| Formula (I-8-29) | Formula (I-8) | Formula (Cbz-29) |
| Formula (I-9-1) | Formula (I-9) | Formula (Cbz-1) |
| Formula (I-9-2) | Formula (I-9) | Formula (Cbz-2) |
| Formula (I-9-3) | Formula (I-9) | Formula (Cbz-3) |
| Formula (I-9-4) | Formula (I-9) | Formula (Cbz-4) |
| Formula (I-9-5) | Formula (I-9) | Formula (Cbz-5) |
| Formula (I-9-6) | Formula (I-9) | Formula (Cbz-6) |
| Formula (I-9-7) | Formula (I-9) | Formula (Cbz-7) |
| Formula (I-9-8) | Formula (I-9) | Formula (Cbz-8) |
| Formula (I-9-9) | Formula (I-9) | Formula (Cbz-9) |
| Formula (I-9-10) | Formula (I-9) | Formula (Cbz-10) |
| Formula (I-9-11) | Formula (I-9) | Formula (Cbz-11) |
| Formula (I-9-12) | Formula (I-9) | Formula (Cbz-12) |
| Formula (I-9-13) | Formula (I-9) | Formula (Cbz-13) |

| Formula | Parent structure | Cbz group |
|---|---|---|
| Formula (I-9-14) | Formula (I-9) | Formula (Cbz-14) |
| Formula (I-9-15) | Formula (I-9) | Formula (Cbz-15) |
| Formula (I-9-16) | Formula (I-9) | Formula (Cbz-16) |
| Formula (I-9-17) | Formula (I-9) | Formula (Cbz-17) |
| Formula (I-9-18) | Formula (I-9) | Formula (Cbz-18) |
| Formula (I-9-19) | Formula (I-9) | Formula (Cbz-19) |
| Formula (I-9-20) | Formula (I-9) | Formula (Cbz-20) |
| Formula (I-9-21) | Formula (I-9) | Formula (Cbz-21) |
| Formula (I-9-22) | Formula (I-9) | Formula (Cbz-22) |
| Formula (I-9-23) | Formula (I-9) | Formula (Cbz-23) |
| Formula (I-9-24) | Formula (I-9) | Formula (Cbz-24) |
| Formula (I-9-25) | Formula (I-9) | Formula (Cbz-25) |
| Formula (I-9-26) | Formula (I-9) | Formula (Cbz-26) |
| Formula (I-9-27) | Formula (I-9) | Formula (Cbz-27) |
| Formula (I-9-28) | Formula (I-9) | Formula (Cbz-28) |
| Formula (I-9-29) | Formula (I-9) | Formula (Cbz-29) |
| Formula (I-10-1) | Formula (I-10) | Formula (Cbz-1) |
| Formula (I-10-2) | Formula (I-10) | Formula (Cbz-2) |
| Formula (I-10-3) | Formula (I-10) | Formula (Cbz-3) |
| Formula (I-10-4) | Formula (I-10) | Formula (Cbz-4) |
| Formula (I-10-5) | Formula (I-10) | Formula (Cbz-5) |
| Formula (I-10-6) | Formula (I-10) | Formula (Cbz-6) |
| Formula (I-10-7) | Formula (I-10) | Formula (Cbz-7) |
| Formula (I-10-8) | Formula (I-10) | Formula (Cbz-8) |
| Formula (I-10-9) | Formula (I-10) | Formula (Cbz-9) |
| Formula (I-10-10) | Formula (I-10) | Formula (Cbz-10) |
| Formula (I-10-11) | Formula (I-10) | Formula (Cbz-11) |
| Formula (I-10-12) | Formula (I-10) | Formula (Cbz-12) |
| Formula (I-10-13) | Formula (I-10) | Formula (Cbz-13) |
| Formula (I-10-14) | Formula (I-10) | Formula (Cbz-14) |
| Formula (I-10-15) | Formula (I-10) | Formula (Cbz-15) |
| Formula (I-10-16) | Formula (I-10) | Formula (Cbz-16) |
| Formula (I-10-17) | Formula (I-10) | Formula (Cbz-17) |
| Formula (I-10-18) | Formula (I-10) | Formula (Cbz-18) |
| Formula (I-10-19) | Formula (I-10) | Formula (Cbz-19) |
| Formula (I-10-20) | Formula (I-10) | Formula (Cbz-20) |
| Formula (I-10-21) | Formula (I-10) | Formula (Cbz-21) |
| Formula (I-10-22) | Formula (I-10) | Formula (Cbz-22) |
| Formula (I-10-23) | Formula (I-10) | Formula (Cbz-23) |
| Formula (I-10-24) | Formula (I-10) | Formula (Cbz-24) |
| Formula (I-10-25) | Formula (I-10) | Formula (Cbz-25) |
| Formula (I-10-26) | Formula (I-10) | Formula (Cbz-26) |
| Formula (I-10-27) | Formula (I-10) | Formula (Cbz-27) |
| Formula (I-10-28) | Formula (I-10) | Formula (Cbz-28) |
| Formula (I-10-29) | Formula (I-10) | Formula (Cbz-29) |
| Formula (I-11-1) | Formula (I-11) | Formula (Cbz-1) |
| Formula (I-11-2) | Formula (I-11) | Formula (Cbz-2) |
| Formula (I-11-3) | Formula (I-11) | Formula (Cbz-3) |
| Formula (I-11-4) | Formula (I-11) | Formula (Cbz-4) |
| Formula (I-11-5) | Formula (I-11) | Formula (Cbz-5) |
| Formula (I-11-6) | Formula (I-11) | Formula (Cbz-6) |
| Formula (I-11-7) | Formula (I-11) | Formula (Cbz-7) |
| Formula (I-11-8) | Formula (I-11) | Formula (Cbz-8) |
| Formula (I-11-9) | Formula (I-11) | Formula (Cbz-9) |
| Formula (I-11-10) | Formula (I-11) | Formula (Cbz-10) |
| Formula (I-11-11) | Formula (I-11) | Formula (Cbz-11) |
| Formula (I-11-12) | Formula (I-11) | Formula (Cbz-12) |
| Formula (I-11-13) | Formula (I-11) | Formula (Cbz-13) |
| Formula (I-11-14) | Formula (I-11) | Formula (Cbz-14) |
| Formula (I-11-15) | Formula (I-11) | Formula (Cbz-15) |
| Formula (I-11-16) | Formula (I-11) | Formula (Cbz-16) |
| Formula (I-11-17) | Formula (I-11) | Formula (Cbz-17) |
| Formula (I-11-18) | Formula (I-11) | Formula (Cbz-18) |
| Formula (I-11-19) | Formula (I-11) | Formula (Cbz-19) |
| Formula (I-11-20) | Formula (I-11) | Formula (Cbz-20) |
| Formula (I-11-21) | Formula (I-11) | Formula (Cbz-21) |
| Formula (I-11-22) | Formula (I-11) | Formula (Cbz-22) |
| Formula (I-11-23) | Formula (I-11) | Formula (Cbz-23) |
| Formula (I-11-24) | Formula (I-11) | Formula (Cbz-24) |
| Formula (I-11-25) | Formula (I-11) | Formula (Cbz-25) |
| Formula (I-11-26) | Formula (I-11) | Formula (Cbz-26) |
| Formula (I-11-27) | Formula (I-11) | Formula (Cbz-27) |
| Formula (I-11-28) | Formula (I-11) | Formula (Cbz-28) |
| Formula (I-11-29) | Formula (I-11) | Formula (Cbz-29) |
| Formula (I-12-1) | Formula (I-12) | Formula (Cbz-1) |
| Formula (I-12-2) | Formula (I-12) | Formula (Cbz-2) |
| Formula (I-12-3) | Formula (I-12) | Formula (Cbz-3) |
| Formula (I-12-4) | Formula (I-12) | Formula (Cbz-4) |
| Formula (I-12-5) | Formula (I-12) | Formula (Cbz-5) |
| Formula (I-12-6) | Formula (I-12) | Formula (Cbz-6) |
| Formula (I-12-7) | Formula (I-12) | Formula (Cbz-7) |
| Formula (I-12-8) | Formula (I-12) | Formula (Cbz-8) |
| Formula (I-12-9) | Formula (I-12) | Formula (Cbz-9) |
| Formula (I-12-10) | Formula (I-12) | Formula (Cbz-10) |
| Formula (I-12-11) | Formula (I-12) | Formula (Cbz-11) |
| Formula (I-12-12) | Formula (I-12) | Formula (Cbz-12) |
| Formula (I-12-13) | Formula (I-12) | Formula (Cbz-13) |
| Formula (I-12-14) | Formula (I-12) | Formula (Cbz-14) |
| Formula (I-12-15) | Formula (I-12) | Formula (Cbz-15) |
| Formula (I-12-16) | Formula (I-12) | Formula (Cbz-16) |
| Formula (I-12-17) | Formula (I-12) | Formula (Cbz-17) |
| Formula (I-12-18) | Formula (I-12) | Formula (Cbz-18) |
| Formula (I-12-19) | Formula (I-12) | Formula (Cbz-19) |
| Formula (I-12-20) | Formula (I-12) | Formula (Cbz-20) |
| Formula (I-12-21) | Formula (I-12) | Formula (Cbz-21) |
| Formula (I-12-22) | Formula (I-12) | Formula (Cbz-22) |
| Formula (I-12-23) | Formula (I-12) | Formula (Cbz-23) |
| Formula (I-12-24) | Formula (I-12) | Formula (Cbz-24) |
| Formula (I-12-25) | Formula (I-12) | Formula (Cbz-25) |
| Formula (I-12-26) | Formula (I-12) | Formula (Cbz-26) |
| Formula (I-12-27) | Formula (I-12) | Formula (Cbz-27) |
| Formula (I-12-28) | Formula (I-12) | Formula (Cbz-28) |
| Formula (I-12-29) | Formula (I-12) | Formula (Cbz-29) |
| Formula (I-13-1) | Formula (I-13) | Formula (Cbz-1) |
| Formula (I-13-2) | Formula (I-13) | Formula (Cbz-2) |
| Formula (I-13-3) | Formula (I-13) | Formula (Cbz-3) |
| Formula (I-13-4) | Formula (I-13) | Formula (Cbz-4) |
| Formula (I-13-5) | Formula (I-13) | Formula (Cbz-5) |
| Formula (I-13-6) | Formula (I-13) | Formula (Cbz-6) |
| Formula (I-13-7) | Formula (I-13) | Formula (Cbz-7) |
| Formula (I-13-8) | Formula (I-13) | Formula (Cbz-8) |
| Formula (I-13-9) | Formula (I-13) | Formula (Cbz-9) |
| Formula (I-13-10) | Formula (I-13) | Formula (Cbz-10) |
| Formula (I-13-11) | Formula (I-13) | Formula (Cbz-11) |
| Formula (I-13-12) | Formula (I-13) | Formula (Cbz-12) |
| Formula (I-13-13) | Formula (I-13) | Formula (Cbz-13) |
| Formula (I-13-14) | Formula (I-13) | Formula (Cbz-14) |
| Formula (I-13-15) | Formula (I-13) | Formula (Cbz-15) |
| Formula (I-13-16) | Formula (I-13) | Formula (Cbz-16) |
| Formula (I-13-17) | Formula (I-13) | Formula (Cbz-17) |
| Formula (I-13-18) | Formula (I-13) | Formula (Cbz-18) |
| Formula (I-13-19) | Formula (I-13) | Formula (Cbz-19) |
| Formula (I-13-20) | Formula (I-13) | Formula (Cbz-20) |
| Formula (I-13-21) | Formula (I-13) | Formula (Cbz-21) |
| Formula (I-13-22) | Formula (I-13) | Formula (Cbz-22) |
| Formula (I-13-23) | Formula (I-13) | Formula (Cbz-23) |
| Formula (I-13-24) | Formula (I-13) | Formula (Cbz-24) |
| Formula (I-13-25) | Formula (I-13) | Formula (Cbz-25) |
| Formula (I-13-26) | Formula (I-13) | Formula (Cbz-26) |
| Formula (I-13-27) | Formula (I-13) | Formula (Cbz-27) |
| Formula (I-13-28) | Formula (I-13) | Formula (Cbz-28) |
| Formula (I-13-29) | Formula (I-13) | Formula (Cbz-29) |
| Formula (I-14-1) | Formula (I-14) | Formula (Cbz-1) |
| Formula (I-14-2) | Formula (I-14) | Formula (Cbz-2) |
| Formula (I-14-3) | Formula (I-14) | Formula (Cbz-3) |
| Formula (I-14-4) | Formula (I-14) | Formula (Cbz-4) |
| Formula (I-14-5) | Formula (I-14) | Formula (Cbz-5) |
| Formula (I-14-6) | Formula (I-14) | Formula (Cbz-6) |
| Formula (I-14-7) | Formula (I-14) | Formula (Cbz-7) |
| Formula (I-14-8) | Formula (I-14) | Formula (Cbz-8) |
| Formula (I-14-9) | Formula (I-14) | Formula (Cbz-9) |
| Formula (I-14-10) | Formula (I-14) | Formula (Cbz-10) |
| Formula (I-14-11) | Formula (I-14) | Formula (Cbz-11) |
| Formula (I-14-12) | Formula (I-14) | Formula (Cbz-12) |
| Formula (I-14-13) | Formula (I-14) | Formula (Cbz-13) |
| Formula (I-14-14) | Formula (I-14) | Formula (Cbz-14) |
| Formula (I-14-15) | Formula (I-14) | Formula (Cbz-15) |
| Formula (I-14-16) | Formula (I-14) | Formula (Cbz-16) |
| Formula (I-14-17) | Formula (I-14) | Formula (Cbz-17) |
| Formula (I-14-18) | Formula (I-14) | Formula (Cbz-18) |
| Formula (I-14-19) | Formula (I-14) | Formula (Cbz-19) |
| Formula (I-14-20) | Formula (I-14) | Formula (Cbz-20) |
| Formula (I-14-21) | Formula (I-14) | Formula (Cbz-21) |
| Formula (I-14-22) | Formula (I-14) | Formula (Cbz-22) |

-continued

| Formula | Parent structure | Cbz group |
|---|---|---|
| Formula (I-14-23) | Formula (I-14) | Formula (Cbz-23) |
| Formula (I-14-24) | Formula (I-14) | Formula (Cbz-24) |
| Formula (I-14-25) | Formula (I-14) | Formula (Cbz-25) |
| Formula (I-14-26) | Formula (I-14) | Formula (Cbz-26) |
| Formula (I-14-27) | Formula (I-14) | Formula (Cbz-27) |
| Formula (I-14-28) | Formula (I-14) | Formula (Cbz-28) |
| Formula (I-14-29) | Formula (I-14) | Formula (Cbz-29) |
| Formula (I-15-1) | Formula (I-15) | Formula (Cbz-1) |
| Formula (I-15-2) | Formula (I-15) | Formula (Cbz-2) |
| Formula (I-15-3) | Formula (I-15) | Formula (Cbz-3) |
| Formula (I-15-4) | Formula (I-15) | Formula (Cbz-4) |
| Formula (I-15-5) | Formula (I-15) | Formula (Cbz-5) |
| Formula (I-15-6) | Formula (I-15) | Formula (Cbz-6) |
| Formula (I-15-7) | Formula (I-15) | Formula (Cbz-7) |
| Formula (I-15-8) | Formula (I-15) | Formula (Cbz-8) |
| Formula (I-15-9) | Formula (I-15) | Formula (Cbz-9) |
| Formula (I-15-10) | Formula (I-15) | Formula (Cbz-10) |
| Formula (I-15-11) | Formula (I-15) | Formula (Cbz-11) |
| Formula (I-15-12) | Formula (I-15) | Formula (Cbz-12) |
| Formula (I-15-13) | Formula (I-15) | Formula (Cbz-13) |
| Formula (I-15-14) | Formula (I-15) | Formula (Cbz-14) |
| Formula (I-15-15) | Formula (I-15) | Formula (Cbz-15) |
| Formula (I-15-16) | Formula (I-15) | Formula (Cbz-16) |
| Formula (I-15-17) | Formula (I-15) | Formula (Cbz-17) |
| Formula (I-15-18) | Formula (I-15) | Formula (Cbz-18) |
| Formula (I-15-19) | Formula (I-15) | Formula (Cbz-19) |
| Formula (I-15-20) | Formula (I-15) | Formula (Cbz-20) |
| Formula (I-15-21) | Formula (I-15) | Formula (Cbz-21) |
| Formula (I-15-22) | Formula (I-15) | Formula (Cbz-22) |
| Formula (I-15-23) | Formula (I-15) | Formula (Cbz-23) |
| Formula (I-15-24) | Formula (I-15) | Formula (Cbz-24) |
| Formula (I-15-25) | Formula (I-15) | Formula (Cbz-25) |
| Formula (I-15-26) | Formula (I-15) | Formula (Cbz-26) |
| Formula (I-15-27) | Formula (I-15) | Formula (Cbz-27) |
| Formula (I-15-28) | Formula (I-15) | Formula (Cbz-28) |
| Formula (I-15-29) | Formula (I-15) | Formula (Cbz-29) |
| Formula (I-16-1) | Formula (I-16) | Formula (Cbz-1) |
| Formula (I-16-2) | Formula (I-16) | Formula (Cbz-2) |
| Formula (I-16-3) | Formula (I-16) | Formula (Cbz-3) |
| Formula (I-16-4) | Formula (I-16) | Formula (Cbz-4) |
| Formula (I-16-5) | Formula (I-16) | Formula (Cbz-5) |
| Formula (I-16-6) | Formula (I-16) | Formula (Cbz-6) |
| Formula (I-16-7) | Formula (I-16) | Formula (Cbz-7) |
| Formula (I-16-8) | Formula (I-16) | Formula (Cbz-8) |
| Formula (I-16-9) | Formula (I-16) | Formula (Cbz-9) |
| Formula (I-16-10) | Formula (I-16) | Formula (Cbz-10) |
| Formula (I-16-11) | Formula (I-16) | Formula (Cbz-11) |
| Formula (I-16-12) | Formula (I-16) | Formula (Cbz-12) |
| Formula (I-16-13) | Formula (I-16) | Formula (Cbz-13) |
| Formula (I-16-14) | Formula (I-16) | Formula (Cbz-14) |
| Formula (I-16-15) | Formula (I-16) | Formula (Cbz-15) |
| Formula (I-16-16) | Formula (I-16) | Formula (Cbz-16) |
| Formula (I-16-17) | Formula (I-16) | Formula (Cbz-17) |
| Formula (I-16-18) | Formula (I-16) | Formula (Cbz-18) |
| Formula (I-16-19) | Formula (I-16) | Formula (Cbz-19) |
| Formula (I-16-20) | Formula (I-16) | Formula (Cbz-20) |
| Formula (I-16-21) | Formula (I-16) | Formula (Cbz-21) |
| Formula (I-16-22) | Formula (I-16) | Formula (Cbz-22) |
| Formula (I-16-23) | Formula (I-16) | Formula (Cbz-23) |
| Formula (I-16-24) | Formula (I-16) | Formula (Cbz-24) |
| Formula (I-16-25) | Formula (I-16) | Formula (Cbz-25) |
| Formula (I-16-26) | Formula (I-16) | Formula (Cbz-26) |
| Formula (I-16-27) | Formula (I-16) | Formula (Cbz-27) |
| Formula (I-16-28) | Formula (I-16) | Formula (Cbz-28) |
| Formula (I-16-29) | Formula (I-16) | Formula (Cbz-29) |
| Formula (I-17-1) | Formula (I-17) | Formula (Cbz-1) |
| Formula (I-17-2) | Formula (I-17) | Formula (Cbz-2) |
| Formula (I-17-3) | Formula (I-17) | Formula (Cbz-3) |
| Formula (I-17-4) | Formula (I-17) | Formula (Cbz-4) |
| Formula (I-17-5) | Formula (I-17) | Formula (Cbz-5) |
| Formula (I-17-6) | Formula (I-17) | Formula (Cbz-6) |
| Formula (I-17-7) | Formula (I-17) | Formula (Cbz-7) |
| Formula (I-17-8) | Formula (I-17) | Formula (Cbz-8) |
| Formula (I-17-9) | Formula (I-17) | Formula (Cbz-9) |
| Formula (I-17-10) | Formula (I-17) | Formula (Cbz-10) |
| Formula (I-17-11) | Formula (I-17) | Formula (Cbz-11) |
| Formula (I-17-12) | Formula (I-17) | Formula (Cbz-12) |
| Formula (I-17-13) | Formula (I-17) | Formula (Cbz-13) |
| Formula (I-17-14) | Formula (I-17) | Formula (Cbz-14) |
| Formula (I-17-15) | Formula (I-17) | Formula (Cbz-15) |
| Formula (I-17-16) | Formula (I-17) | Formula (Cbz-16) |
| Formula (I-17-17) | Formula (I-17) | Formula (Cbz-17) |
| Formula (I-17-18) | Formula (I-17) | Formula (Cbz-18) |
| Formula (I-17-19) | Formula (I-17) | Formula (Cbz-19) |
| Formula (I-17-20) | Formula (I-17) | Formula (Cbz-20) |
| Formula (I-17-21) | Formula (I-17) | Formula (Cbz-21) |
| Formula (I-17-22) | Formula (I-17) | Formula (Cbz-22) |
| Formula (I-17-23) | Formula (I-17) | Formula (Cbz-23) |
| Formula (I-17-24) | Formula (I-17) | Formula (Cbz-24) |
| Formula (I-17-25) | Formula (I-17) | Formula (Cbz-25) |
| Formula (I-17-26) | Formula (I-17) | Formula (Cbz-26) |
| Formula (I-17-27) | Formula (I-17) | Formula (Cbz-27) |
| Formula (I-17-28) | Formula (I-17) | Formula (Cbz-28) |
| Formula (I-17-29) | Formula (I-17) | Formula (Cbz-29) |
| Formula (I-18-1) | Formula (I-18) | Formula (Cbz-1) |
| Formula (I-18-2) | Formula (I-18) | Formula (Cbz-2) |
| Formula (I-18-3) | Formula (I-18) | Formula (Cbz-3) |
| Formula (I-18-4) | Formula (I-18) | Formula (Cbz-4) |
| Formula (I-18-5) | Formula (I-18) | Formula (Cbz-5) |
| Formula (I-18-6) | Formula (I-18) | Formula (Cbz-6) |
| Formula (I-18-7) | Formula (I-18) | Formula (Cbz-7) |
| Formula (I-18-8) | Formula (I-18) | Formula (Cbz-8) |
| Formula (I-18-9) | Formula (I-18) | Formula (Cbz-9) |
| Formula (I-18-10) | Formula (I-18) | Formula (Cbz-10) |
| Formula (I-18-11) | Formula (I-18) | Formula (Cbz-11) |
| Formula (I-18-12) | Formula (I-18) | Formula (Cbz-12) |
| Formula (I-18-13) | Formula (I-18) | Formula (Cbz-13) |
| Formula (I-18-14) | Formula (I-18) | Formula (Cbz-14) |
| Formula (I-18-15) | Formula (I-18) | Formula (Cbz-15) |
| Formula (I-18-16) | Formula (I-18) | Formula (Cbz-16) |
| Formula (I-18-17) | Formula (I-18) | Formula (Cbz-17) |
| Formula (I-18-18) | Formula (I-18) | Formula (Cbz-18) |
| Formula (I-18-19) | Formula (I-18) | Formula (Cbz-19) |
| Formula (I-18-20) | Formula (I-18) | Formula (Cbz-20) |
| Formula (I-18-21) | Formula (I-18) | Formula (Cbz-21) |
| Formula (I-18-22) | Formula (I-18) | Formula (Cbz-22) |
| Formula (I-18-23) | Formula (I-18) | Formula (Cbz-23) |
| Formula (I-18-24) | Formula (I-18) | Formula (Cbz-24) |
| Formula (I-18-25) | Formula (I-18) | Formula (Cbz-25) |
| Formula (I-18-26) | Formula (I-18) | Formula (Cbz-26) |
| Formula (I-18-27) | Formula (I-18) | Formula (Cbz-27) |
| Formula (I-18-28) | Formula (I-18) | Formula (Cbz-28) |
| Formula (I-18-29) | Formula (I-18) | Formula (Cbz-29) |
| Formula (I-19-1) | Formula (I-19) | Formula (Cbz-1) |
| Formula (I-19-2) | Formula (I-19) | Formula (Cbz-2) |
| Formula (I-19-3) | Formula (I-19) | Formula (Cbz-3) |
| Formula (I-19-4) | Formula (I-19) | Formula (Cbz-4) |
| Formula (I-19-5) | Formula (I-19) | Formula (Cbz-5) |
| Formula (I-19-6) | Formula (I-19) | Formula (Cbz-6) |
| Formula (I-19-7) | Formula (I-19) | Formula (Cbz-7) |
| Formula (I-19-8) | Formula (I-19) | Formula (Cbz-8) |
| Formula (I-19-9) | Formula (I-19) | Formula (Cbz-9) |
| Formula (I-19-10) | Formula (I-19) | Formula (Cbz-10) |
| Formula (I-19-11) | Formula (I-19) | Formula (Cbz-11) |
| Formula (I-19-12) | Formula (I-19) | Formula (Cbz-12) |
| Formula (I-19-13) | Formula (I-19) | Formula (Cbz-13) |
| Formula (I-19-14) | Formula (I-19) | Formula (Cbz-14) |
| Formula (I-19-15) | Formula (I-19) | Formula (Cbz-15) |
| Formula (I-19-16) | Formula (I-19) | Formula (Cbz-16) |
| Formula (I-19-17) | Formula (I-19) | Formula (Cbz-17) |
| Formula (I-19-18) | Formula (I-19) | Formula (Cbz-18) |
| Formula (I-19-19) | Formula (I-19) | Formula (Cbz-19) |
| Formula (I-19-20) | Formula (I-19) | Formula (Cbz-20) |
| Formula (I-19-21) | Formula (I-19) | Formula (Cbz-21) |
| Formula (I-19-22) | Formula (I-19) | Formula (Cbz-22) |
| Formula (I-19-23) | Formula (I-19) | Formula (Cbz-23) |
| Formula (I-19-24) | Formula (I-19) | Formula (Cbz-24) |
| Formula (I-19-25) | Formula (I-19) | Formula (Cbz-25) |
| Formula (I-19-26) | Formula (I-19) | Formula (Cbz-26) |
| Formula (I-19-27) | Formula (I-19) | Formula (Cbz-27) |
| Formula (I-19-28) | Formula (I-19) | Formula (Cbz-28) |
| Formula (I-19-29) | Formula (I-19) | Formula (Cbz-29) |
| Formula (I-20-1) | Formula (I-20) | Formula (Cbz-1) |
| Formula (I-20-2) | Formula (I-20) | Formula (Cbz-2) |

| Formula | Parent structure | Cbz group |
| --- | --- | --- |
| Formula (I-20-3) | Formula (I-20) | Formula (Cbz-3) |
| Formula (I-20-4) | Formula (I-20) | Formula (Cbz-4) |
| Formula (I-20-5) | Formula (I-20) | Formula (Cbz-5) |
| Formula (I-20-6) | Formula (I-20) | Formula (Cbz-6) |
| Formula (I-20-7) | Formula (I-20) | Formula (Cbz-7) |
| Formula (I-20-8) | Formula (I-20) | Formula (Cbz-8) |
| Formula (I-20-9) | Formula (I-20) | Formula (Cbz-9) |
| Formula (I-20-10) | Formula (I-20) | Formula (Cbz-10) |
| Formula (I-20-11) | Formula (I-20) | Formula (Cbz-11) |
| Formula (I-20-12) | Formula (I-20) | Formula (Cbz-12) |
| Formula (I-20-13) | Formula (I-20) | Formula (Cbz-13) |
| Formula (I-20-14) | Formula (I-20) | Formula (Cbz-14) |
| Formula (I-20-15) | Formula (I-20) | Formula (Cbz-15) |
| Formula (I-20-16) | Formula (I-20) | Formula (Cbz-16) |
| Formula (I-20-17) | Formula (I-20) | Formula (Cbz-17) |
| Formula (I-20-18) | Formula (I-20) | Formula (Cbz-18) |
| Formula (I-20-19) | Formula (I-20) | Formula (Cbz-19) |
| Formula (I-20-20) | Formula (I-20) | Formula (Cbz-20) |
| Formula (I-20-21) | Formula (I-20) | Formula (Cbz-21) |
| Formula (I-20-22) | Formula (I-20) | Formula (Cbz-22) |
| Formula (I-20-23) | Formula (I-20) | Formula (Cbz-23) |
| Formula (I-20-24) | Formula (I-20) | Formula (Cbz-24) |
| Formula (I-20-25) | Formula (I-20) | Formula (Cbz-25) |
| Formula (I-20-26) | Formula (I-20) | Formula (Cbz-26) |
| Formula (I-20-27) | Formula (I-20) | Formula (Cbz-27) |
| Formula (I-20-28) | Formula (I-20) | Formula (Cbz-28) |
| Formula (I-20-29) | Formula (I-20) | Formula (Cbz-29) |
| Formula (I-21-1) | Formula (I-21) | Formula (Cbz-1) |
| Formula (I-21-2) | Formula (I-21) | Formula (Cbz-2) |
| Formula (I-21-3) | Formula (I-21) | Formula (Cbz-3) |
| Formula (I-21-4) | Formula (I-21) | Formula (Cbz-4) |
| Formula (I-21-5) | Formula (I-21) | Formula (Cbz-5) |
| Formula (I-21-6) | Formula (I-21) | Formula (Cbz-6) |
| Formula (I-21-7) | Formula (I-21) | Formula (Cbz-7) |
| Formula (I-21-8) | Formula (I-21) | Formula (Cbz-8) |
| Formula (I-21-9) | Formula (I-21) | Formula (Cbz-9) |
| Formula (I-21-10) | Formula (I-21) | Formula (Cbz-10) |
| Formula (I-21-11) | Formula (I-21) | Formula (Cbz-11) |
| Formula (I-21-12) | Formula (I-21) | Formula (Cbz-12) |
| Formula (I-21-13) | Formula (I-21) | Formula (Cbz-13) |
| Formula (I-21-14) | Formula (I-21) | Formula (Cbz-14) |
| Formula (I-21-15) | Formula (I-21) | Formula (Cbz-15) |
| Formula (I-21-16) | Formula (I-21) | Formula (Cbz-16) |
| Formula (I-21-17) | Formula (I-21) | Formula (Cbz-17) |
| Formula (I-21-18) | Formula (I-21) | Formula (Cbz-18) |
| Formula (I-21-19) | Formula (I-21) | Formula (Cbz-19) |
| Formula (I-21-20) | Formula (I-21) | Formula (Cbz-20) |
| Formula (I-21-21) | Formula (I-21) | Formula (Cbz-21) |
| Formula (I-21-22) | Formula (I-21) | Formula (Cbz-22) |
| Formula (I-21-23) | Formula (I-21) | Formula (Cbz-23) |
| Formula (I-21-24) | Formula (I-21) | Formula (Cbz-24) |
| Formula (I-21-25) | Formula (I-21) | Formula (Cbz-25) |
| Formula (I-21-26) | Formula (I-21) | Formula (Cbz-26) |
| Formula (I-21-27) | Formula (I-21) | Formula (Cbz-27) |
| Formula (I-21-28) | Formula (I-21) | Formula (Cbz-28) |
| Formula (I-21-29) | Formula (I-21) | Formula (Cbz-29) |
| Formula (I-22-1) | Formula (I-22) | Formula (Cbz-1) |
| Formula (I-22-2) | Formula (I-22) | Formula (Cbz-2) |
| Formula (I-22-3) | Formula (I-22) | Formula (Cbz-3) |
| Formula (I-22-4) | Formula (I-22) | Formula (Cbz-4) |
| Formula (I-22-5) | Formula (I-22) | Formula (Cbz-5) |
| Formula (I-22-6) | Formula (I-22) | Formula (Cbz-6) |
| Formula (I-22-7) | Formula (I-22) | Formula (Cbz-7) |
| Formula (I-22-8) | Formula (I-22) | Formula (Cbz-8) |
| Formula (I-22-9) | Formula (I-22) | Formula (Cbz-9) |
| Formula (I-22-10) | Formula (I-22) | Formula (Cbz-10) |
| Formula (I-22-11) | Formula (I-22) | Formula (Cbz-11) |
| Formula (I-22-12) | Formula (I-22) | Formula (Cbz-12) |
| Formula (I-22-13) | Formula (I-22) | Formula (Cbz-13) |
| Formula (I-22-14) | Formula (I-22) | Formula (Cbz-14) |
| Formula (I-22-15) | Formula (I-22) | Formula (Cbz-15) |
| Formula (I-22-16) | Formula (I-22) | Formula (Cbz-16) |
| Formula (I-22-17) | Formula (I-22) | Formula (Cbz-17) |
| Formula (I-22-18) | Formula (I-22) | Formula (Cbz-18) |
| Formula (I-22-19) | Formula (I-22) | Formula (Cbz-19) |
| Formula (I-22-20) | Formula (I-22) | Formula (Cbz-20) |
| Formula (I-22-21) | Formula (I-22) | Formula (Cbz-21) |
| Formula (I-22-22) | Formula (I-22) | Formula (Cbz-22) |
| Formula (I-22-23) | Formula (I-22) | Formula (Cbz-23) |
| Formula (I-22-24) | Formula (I-22) | Formula (Cbz-24) |
| Formula (I-22-25) | Formula (I-22) | Formula (Cbz-25) |
| Formula (I-22-26) | Formula (I-22) | Formula (Cbz-26) |
| Formula (I-22-27) | Formula (I-22) | Formula (Cbz-27) |
| Formula (I-22-28) | Formula (I-22) | Formula (Cbz-28) |
| Formula (I-22-29) | Formula (I-22) | Formula (Cbz-29) |
| Formula (I-23-1) | Formula (I-23) | Formula (Cbz-1) |
| Formula (I-23-2) | Formula (I-23) | Formula (Cbz-2) |
| Formula (I-23-3) | Formula (I-23) | Formula (Cbz-3) |
| Formula (I-23-4) | Formula (I-23) | Formula (Cbz-4) |
| Formula (I-23-5) | Formula (I-23) | Formula (Cbz-5) |
| Formula (I-23-6) | Formula (I-23) | Formula (Cbz-6) |
| Formula (I-23-7) | Formula (I-23) | Formula (Cbz-7) |
| Formula (I-23-8) | Formula (I-23) | Formula (Cbz-8) |
| Formula (I-23-9) | Formula (I-23) | Formula (Cbz-9) |
| Formula (I-23-10) | Formula (I-23) | Formula (Cbz-10) |
| Formula (I-23-11) | Formula (I-23) | Formula (Cbz-11) |
| Formula (I-23-12) | Formula (I-23) | Formula (Cbz-12) |
| Formula (I-23-13) | Formula (I-23) | Formula (Cbz-13) |
| Formula (I-23-14) | Formula (I-23) | Formula (Cbz-14) |
| Formula (I-23-15) | Formula (I-23) | Formula (Cbz-15) |
| Formula (I-23-16) | Formula (I-23) | Formula (Cbz-16) |
| Formula (I-23-17) | Formula (I-23) | Formula (Cbz-17) |
| Formula (I-23-18) | Formula (I-23) | Formula (Cbz-18) |
| Formula (I-23-19) | Formula (I-23) | Formula (Cbz-19) |
| Formula (I-23-20) | Formula (I-23) | Formula (Cbz-20) |
| Formula (I-23-21) | Formula (I-23) | Formula (Cbz-21) |
| Formula (I-23-22) | Formula (I-23) | Formula (Cbz-22) |
| Formula (I-23-23) | Formula (I-23) | Formula (Cbz-23) |
| Formula (I-23-24) | Formula (I-23) | Formula (Cbz-24) |
| Formula (I-23-25) | Formula (I-23) | Formula (Cbz-25) |
| Formula (I-23-26) | Formula (I-23) | Formula (Cbz-26) |
| Formula (I-23-27) | Formula (I-23) | Formula (Cbz-27) |
| Formula (I-23-28) | Formula (I-23) | Formula (Cbz-28) |
| Formula (I-23-29) | Formula (I-23) | Formula (Cbz-29) |
| Formula (I-24-1) | Formula (I-24) | Formula (Cbz-1) |
| Formula (I-24-2) | Formula (I-24) | Formula (Cbz-2) |
| Formula (I-24-3) | Formula (I-24) | Formula (Cbz-3) |
| Formula (I-24-4) | Formula (I-24) | Formula (Cbz-4) |
| Formula (I-24-5) | Formula (I-24) | Formula (Cbz-5) |
| Formula (I-24-6) | Formula (I-24) | Formula (Cbz-6) |
| Formula (I-24-7) | Formula (I-24) | Formula (Cbz-7) |
| Formula (I-24-8) | Formula (I-24) | Formula (Cbz-8) |
| Formula (I-24-9) | Formula (I-24) | Formula (Cbz-9) |
| Formula (I-24-10) | Formula (I-24) | Formula (Cbz-10) |
| Formula (I-24-11) | Formula (I-24) | Formula (Cbz-11) |
| Formula (I-24-12) | Formula (I-24) | Formula (Cbz-12) |
| Formula (I-24-13) | Formula (I-24) | Formula (Cbz-13) |
| Formula (I-24-14) | Formula (I-24) | Formula (Cbz-14) |
| Formula (I-24-15) | Formula (I-24) | Formula (Cbz-15) |
| Formula (I-24-16) | Formula (I-24) | Formula (Cbz-16) |
| Formula (I-24-17) | Formula (I-24) | Formula (Cbz-17) |
| Formula (I-24-18) | Formula (I-24) | Formula (Cbz-18) |
| Formula (I-24-19) | Formula (I-24) | Formula (Cbz-19) |
| Formula (I-24-20) | Formula (I-24) | Formula (Cbz-20) |
| Formula (I-24-21) | Formula (I-24) | Formula (Cbz-21) |
| Formula (I-24-22) | Formula (I-24) | Formula (Cbz-22) |
| Formula (I-24-23) | Formula (I-24) | Formula (Cbz-23) |
| Formula (I-24-24) | Formula (I-24) | Formula (Cbz-24) |
| Formula (I-24-25) | Formula (I-24) | Formula (Cbz-25) |
| Formula (I-24-26) | Formula (I-24) | Formula (Cbz-26) |
| Formula (I-24-27) | Formula (I-24) | Formula (Cbz-27) |
| Formula (I-24-28) | Formula (I-24) | Formula (Cbz-28) |
| Formula (I-24-29) | Formula (I-24) | Formula (Cbz-29) |

For the abovementioned formulae, it is preferable that the compound parts -Cbz-Ar$^2$ and —Ar$^1$-Cbz-Ar$^2$ are each bonded to the aromatic six-membered ring in the position para to the nitrogen atom, as shown by the following example for formula (I-1):

Formula (I-1-a)
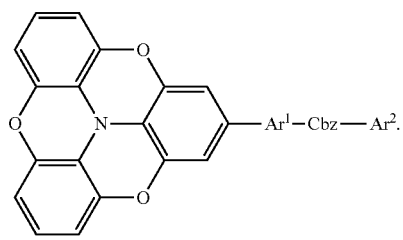
For the abovementioned formulae, it is preferable that the variables conform to the abovementioned preferred embodiments. It is especially preferable that the $Ar^1$ and $Ar^2$ groups therein conform to the abovementioned preferred embodiments.
Preferred explicit compounds of the formula (I) are shown below:
1
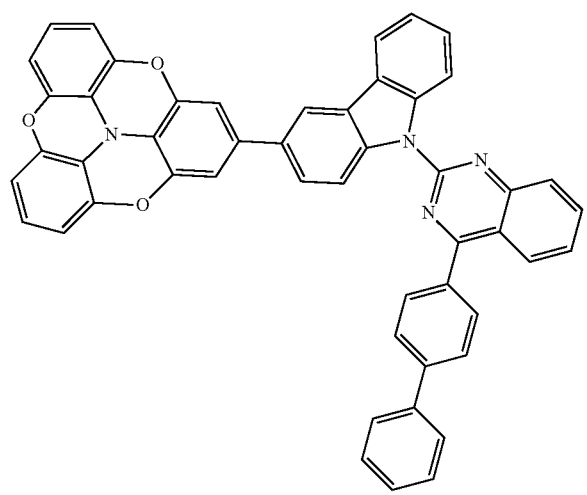
2
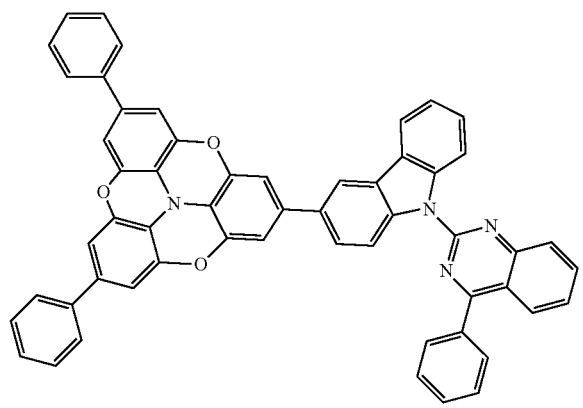
3
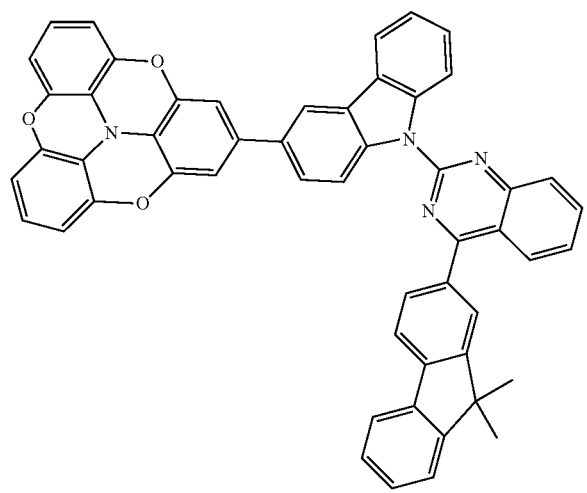
4
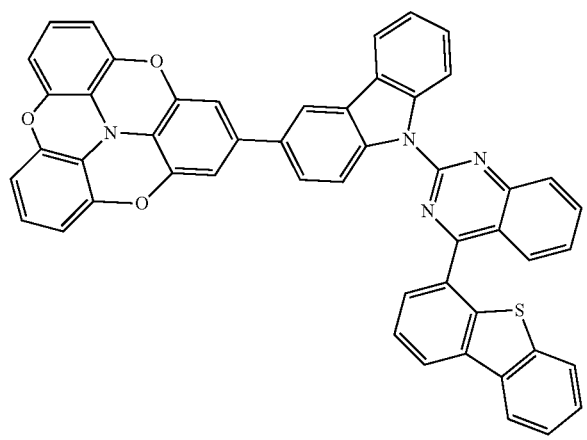

-continued
5
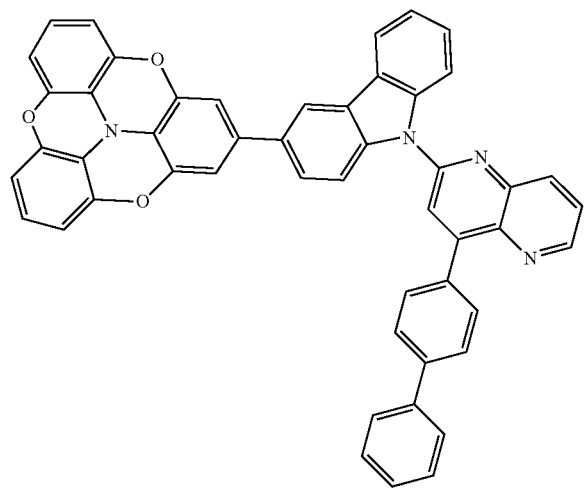
6
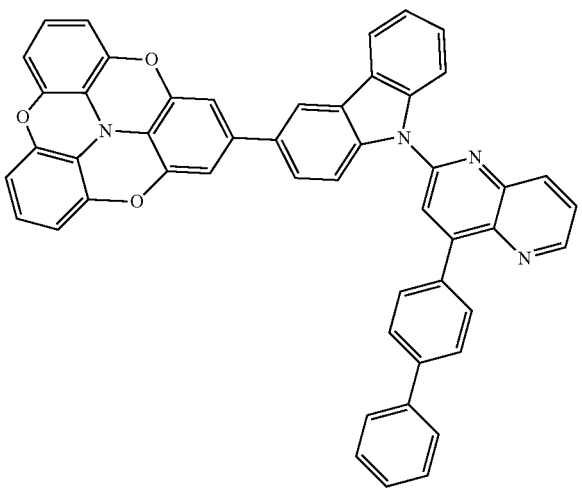
7
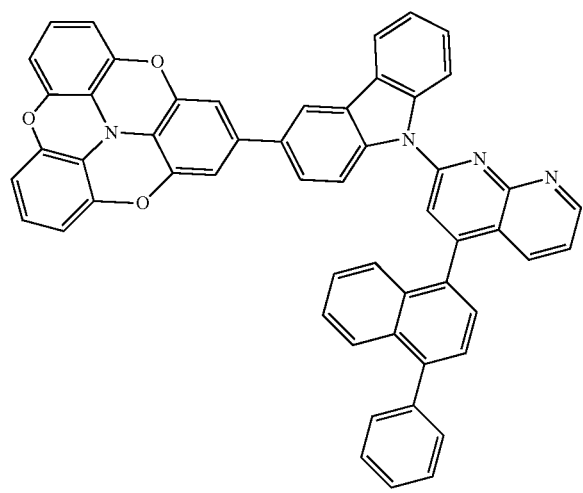
8
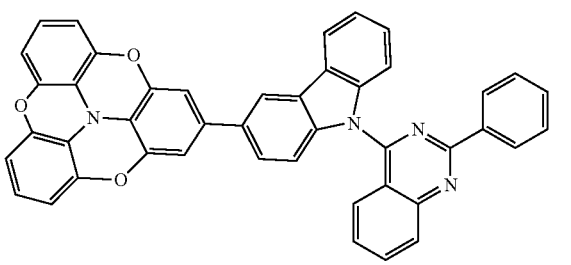
9
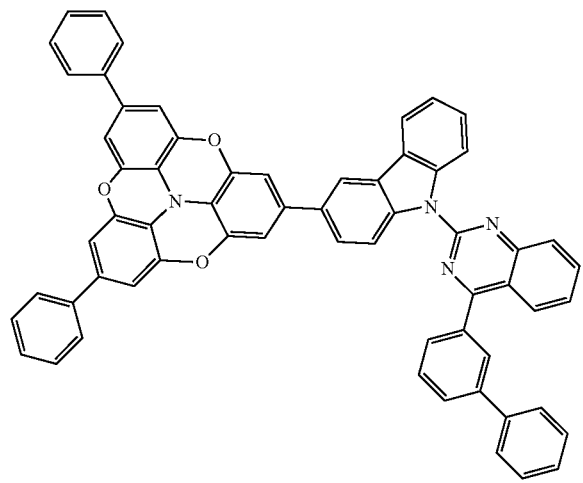
10
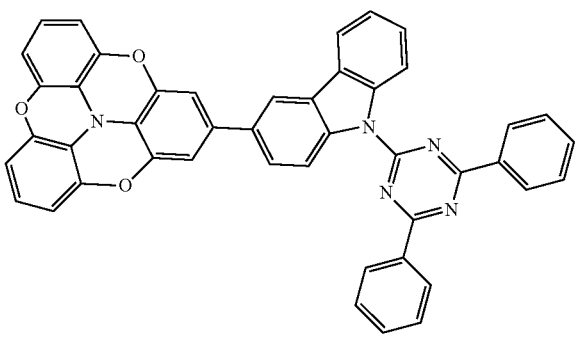

-continued
11
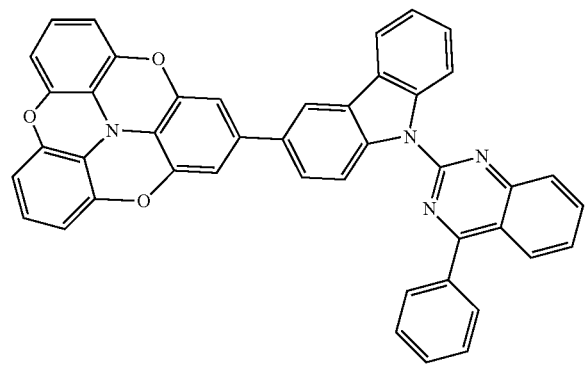
12
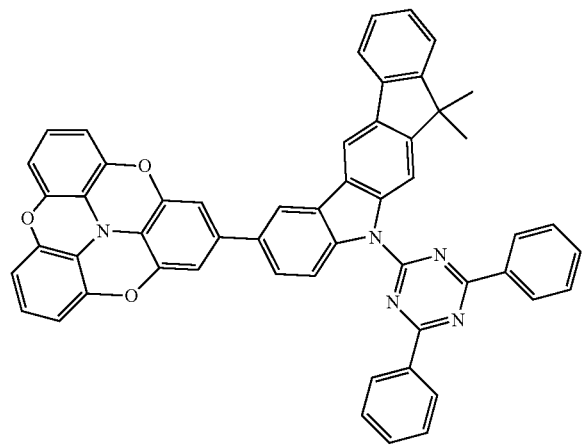
13
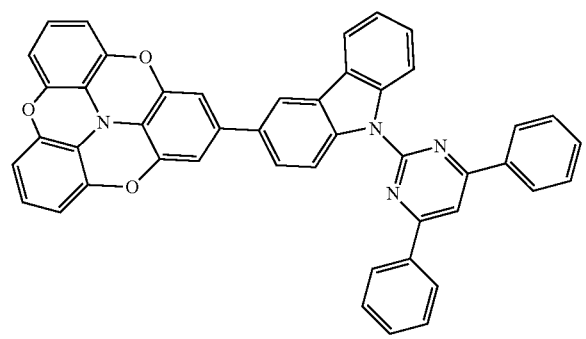
14
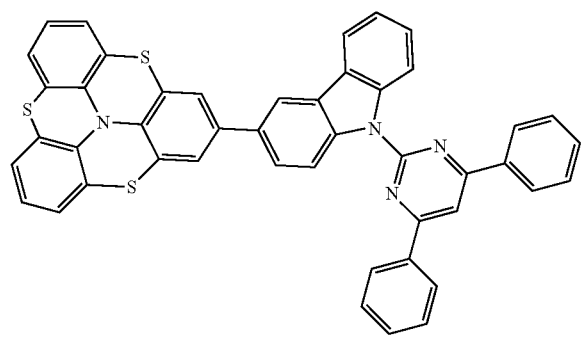
15
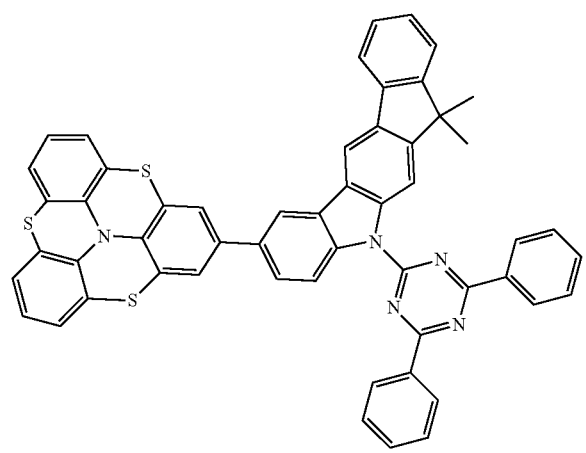
16
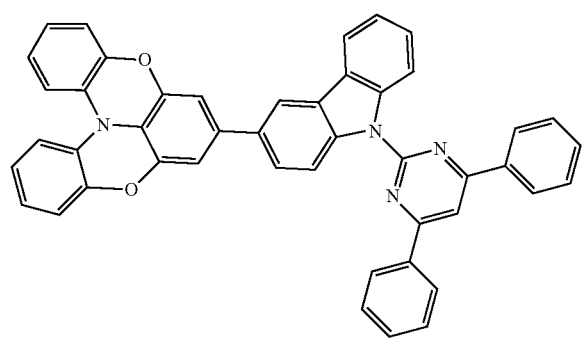

-continued
17
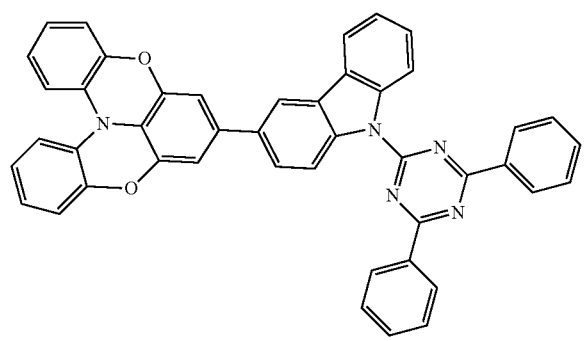
18
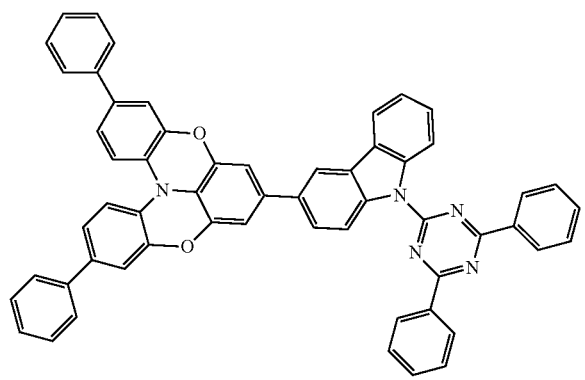
19
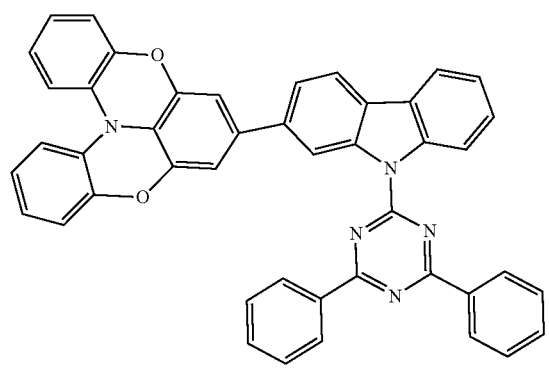
20
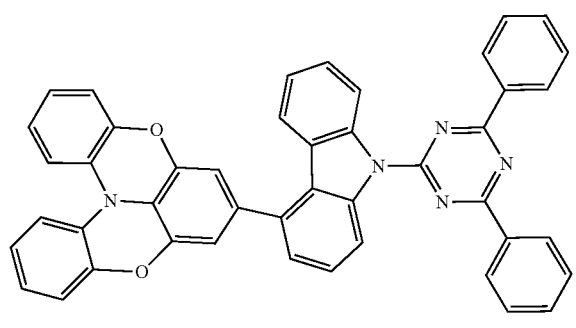
21
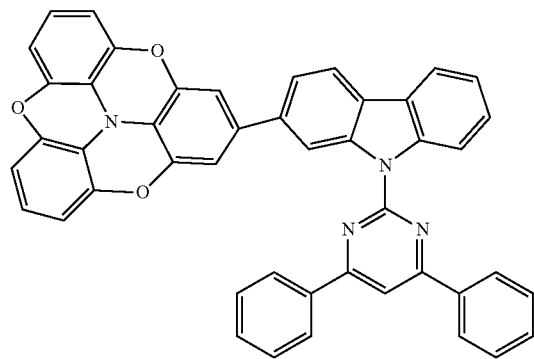
22
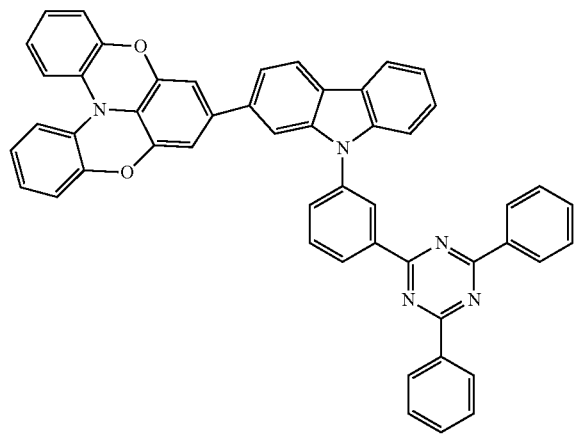
23
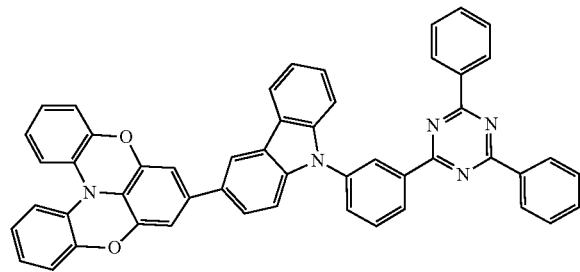
24
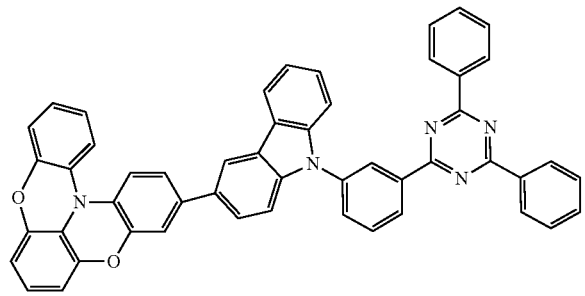

-continued
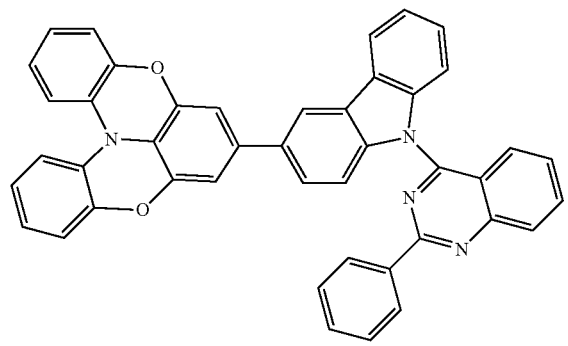
25
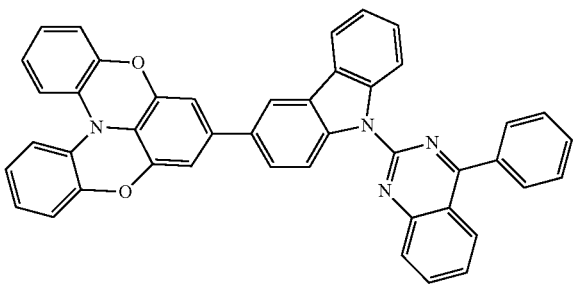
26
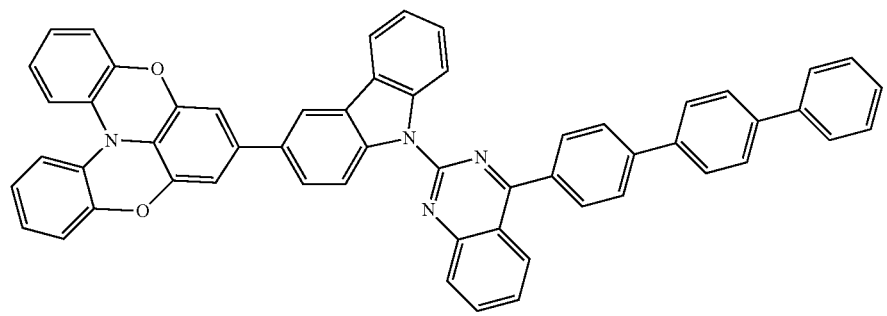
27
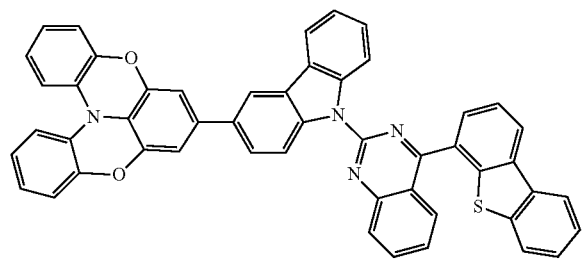
28
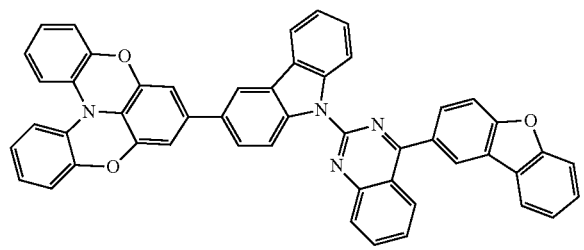
29
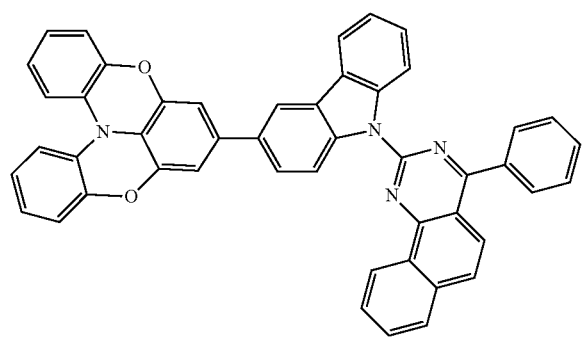
30
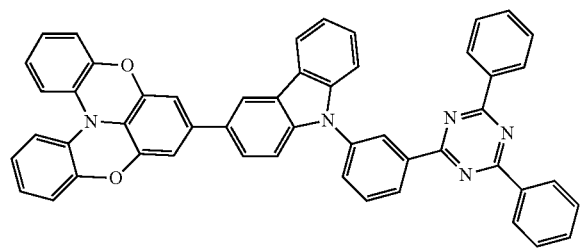
32
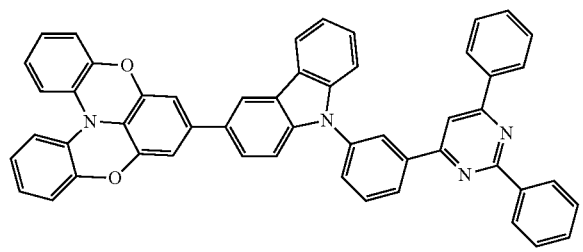
33

-continued
34
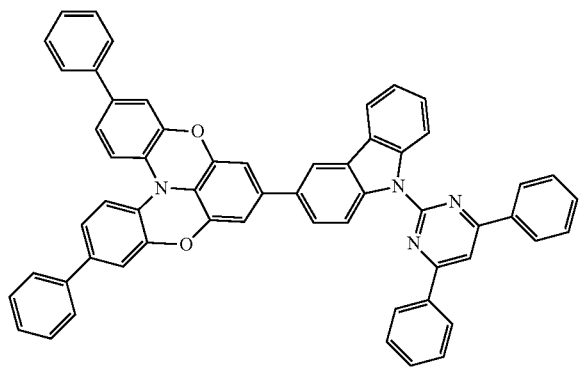
35
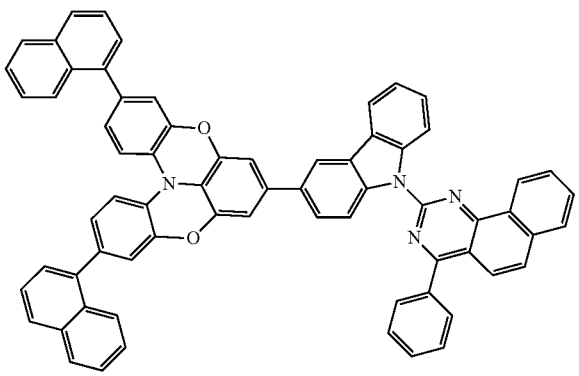
36
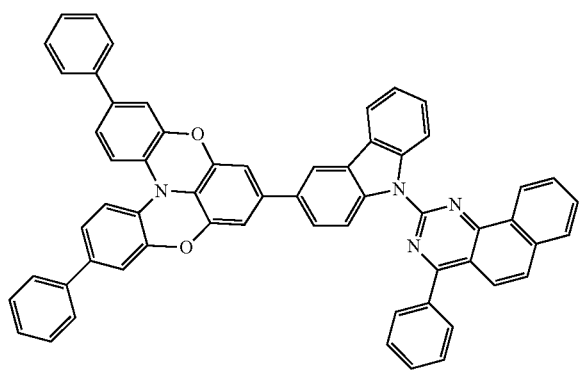
37
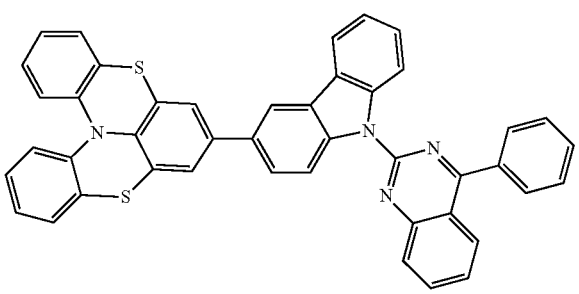
38
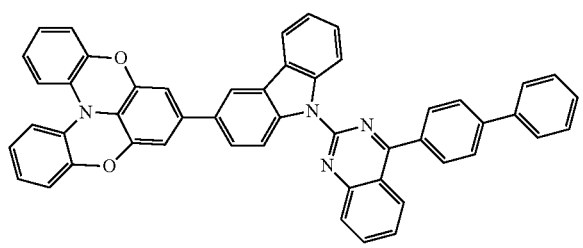
39
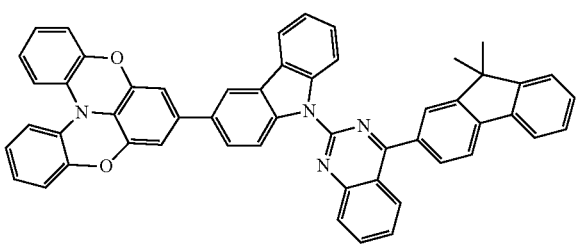
40
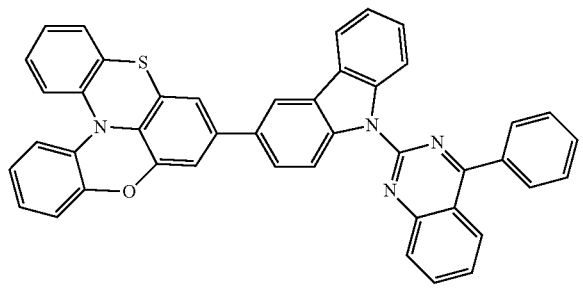
41
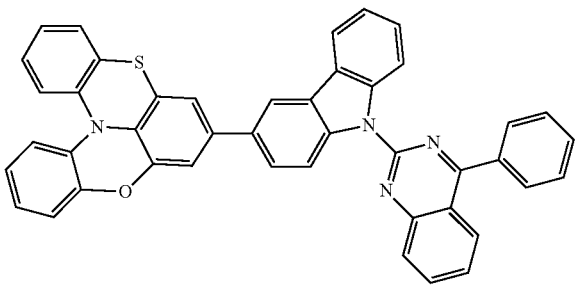

-continued
42
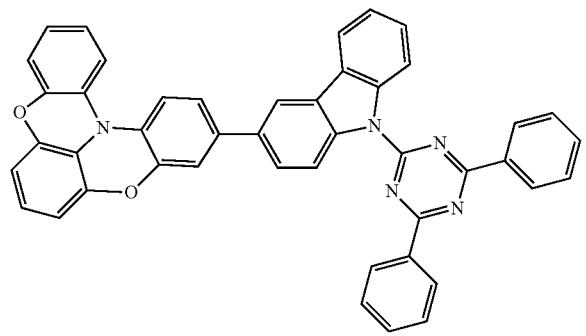
43
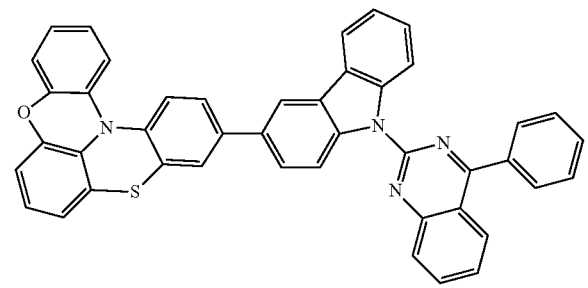
44
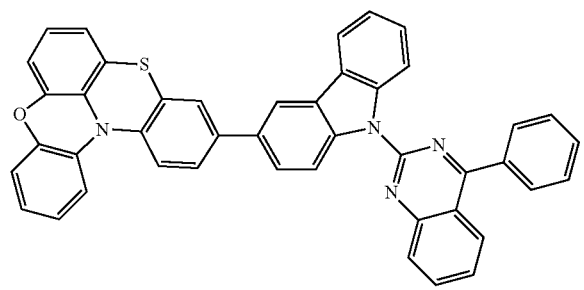
45
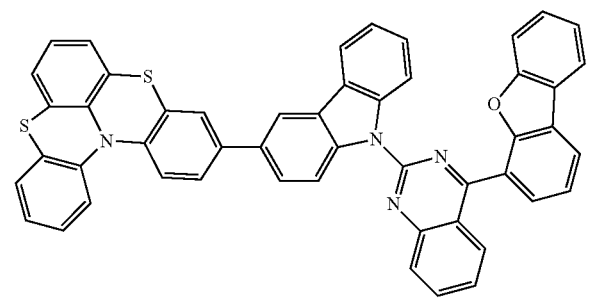
46
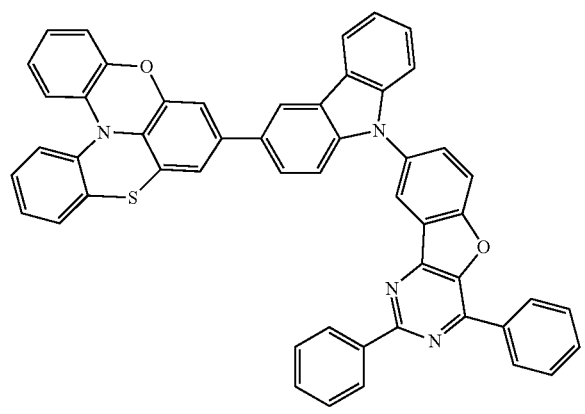
47
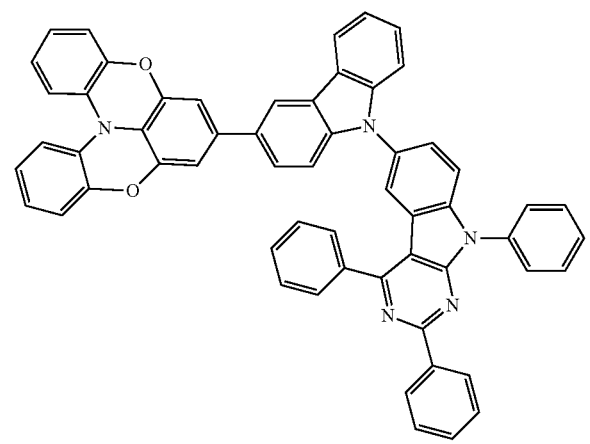

48
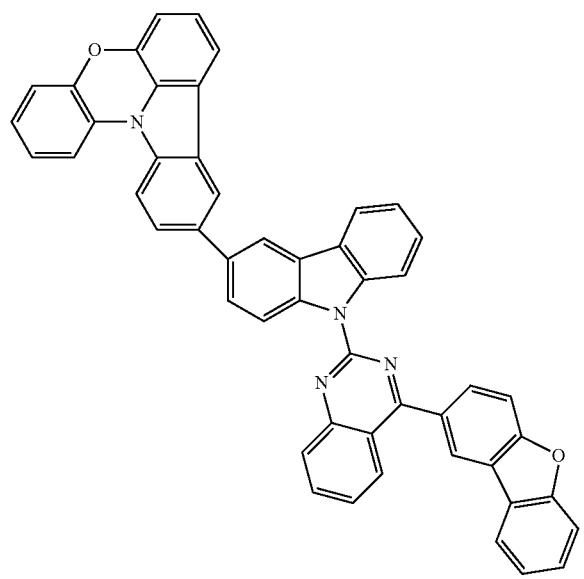
49
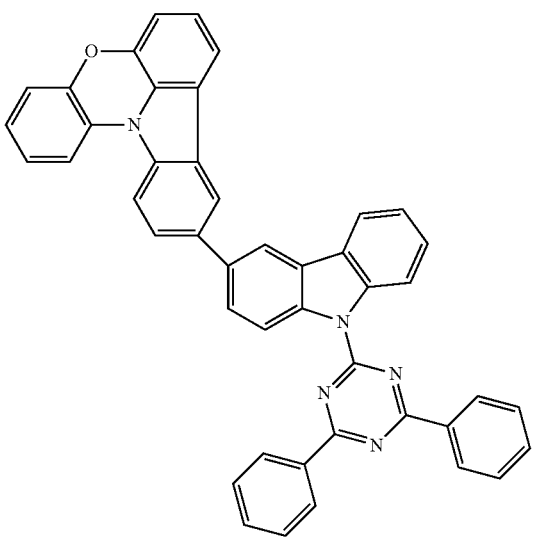
50
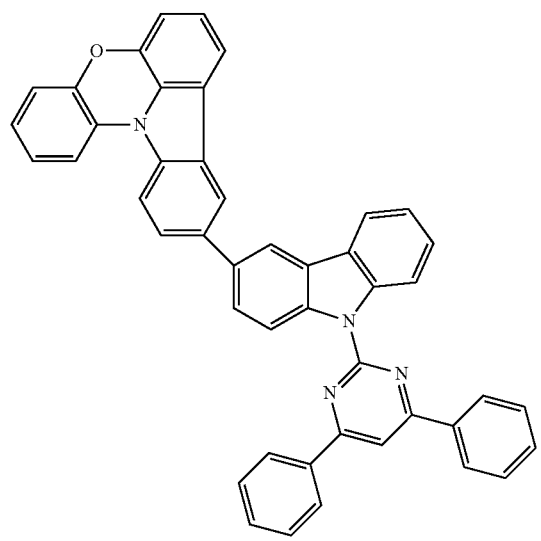
51
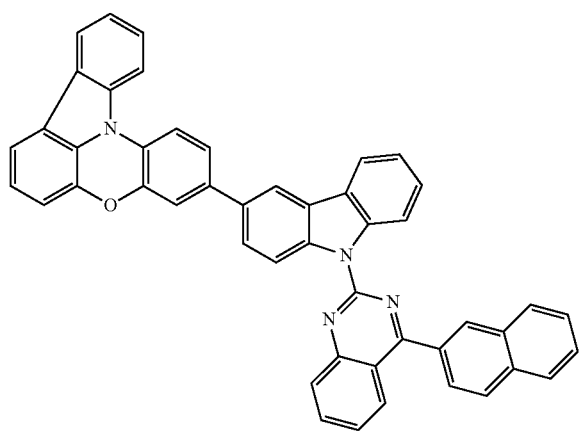

-continued
52
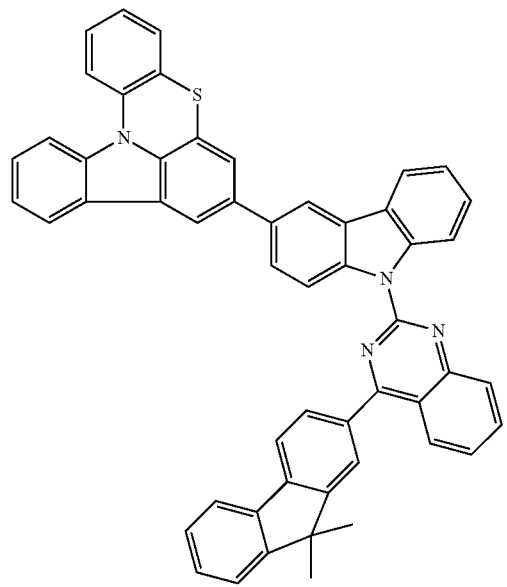
53
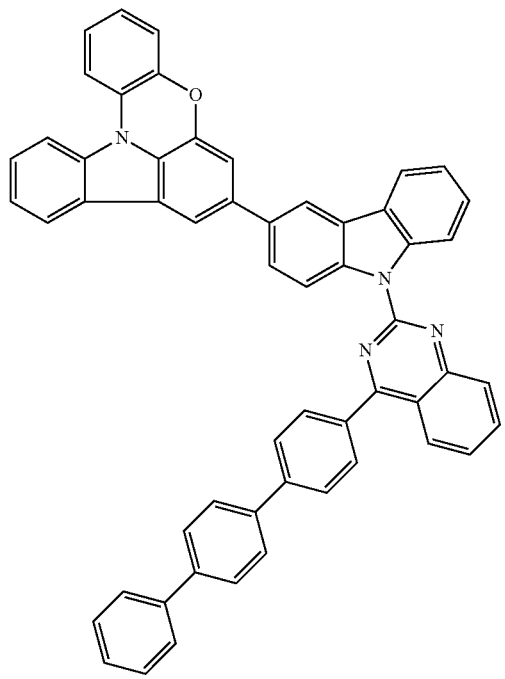
54
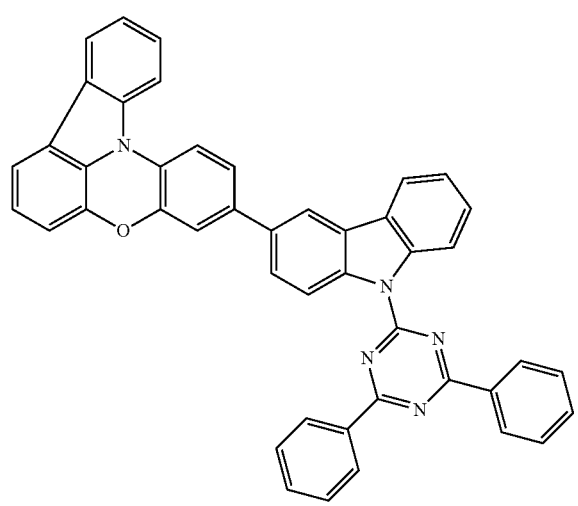
55
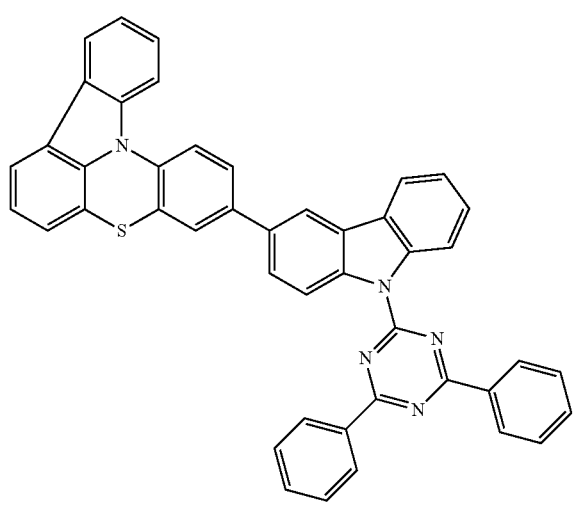

-continued
56
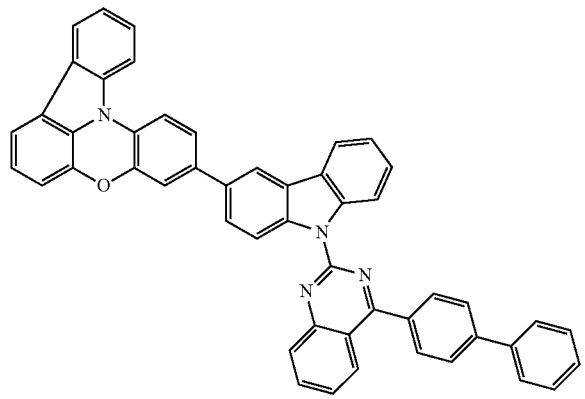
57
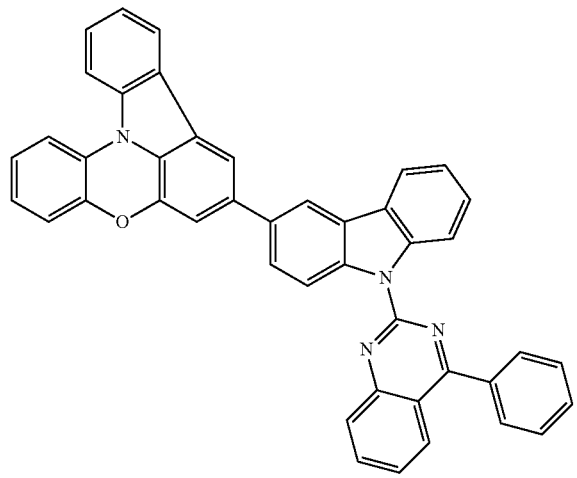
58
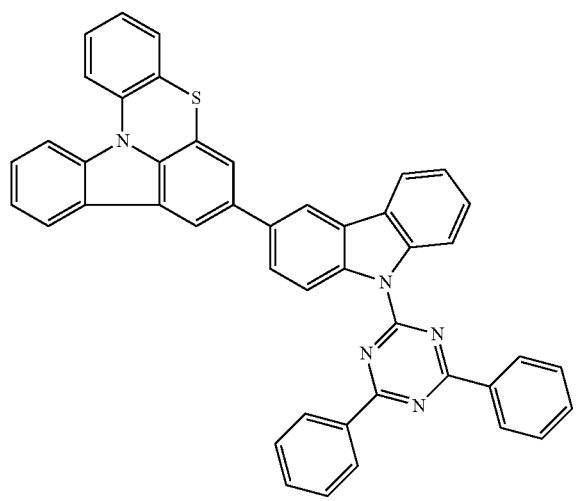
59
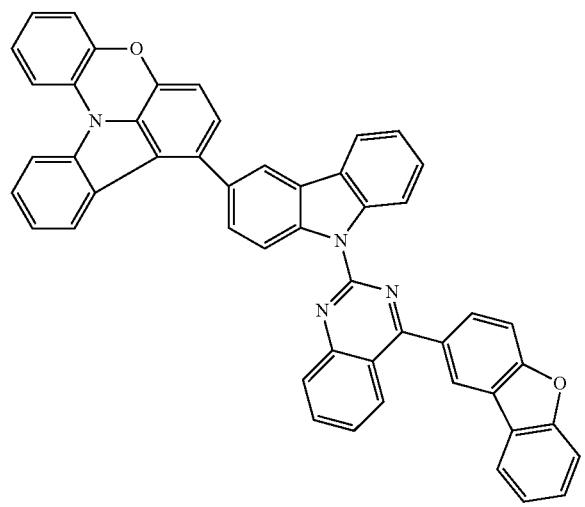
60
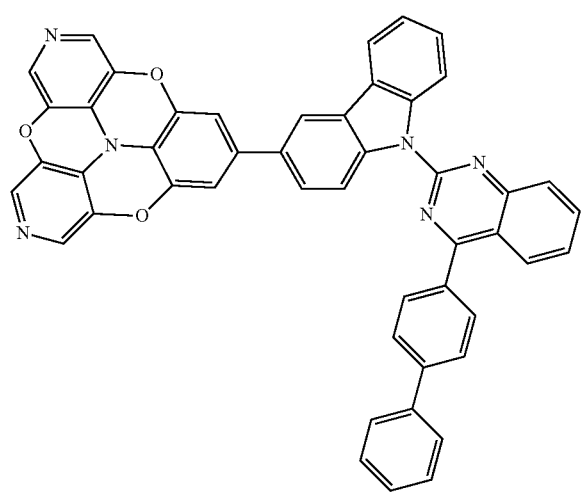
61
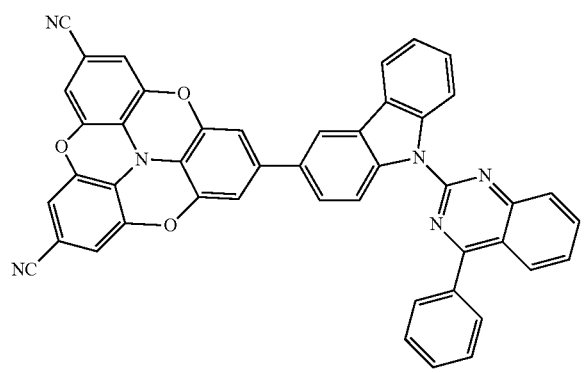

-continued
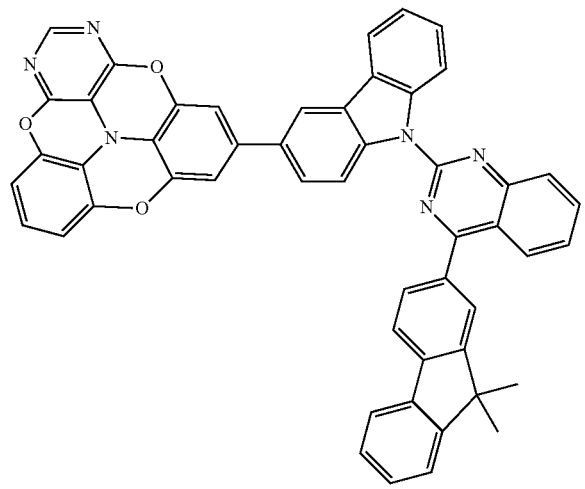
62
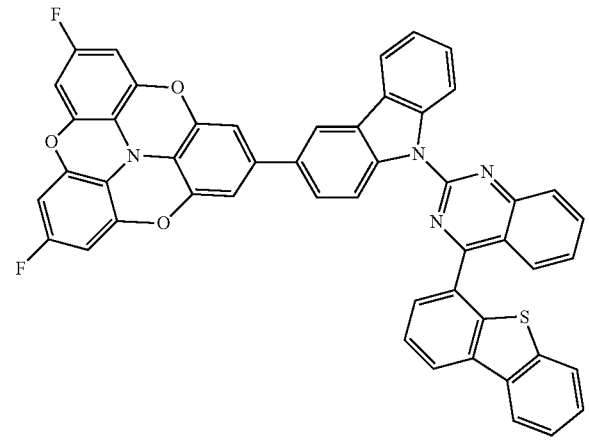
63
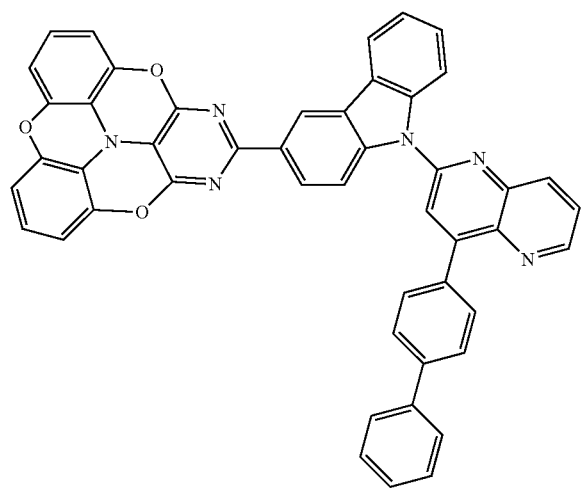
64
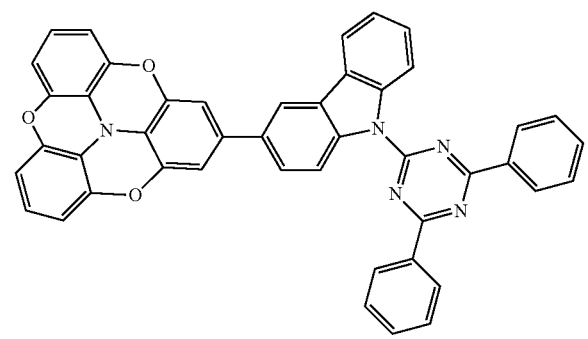
65
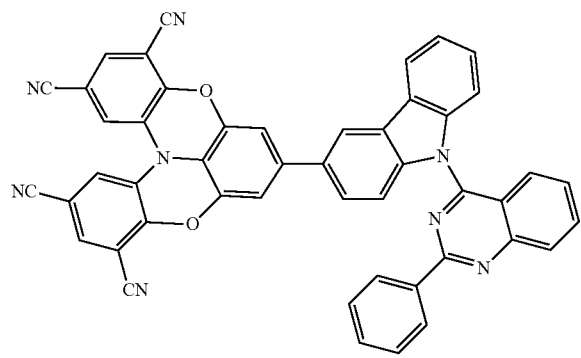
66
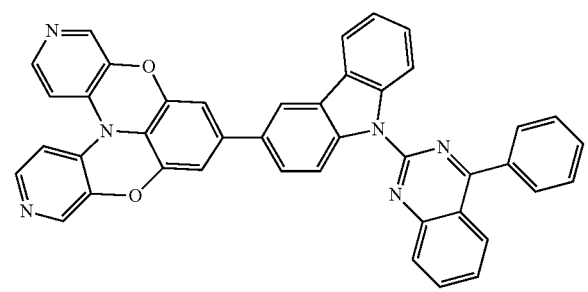
67

-continued
68
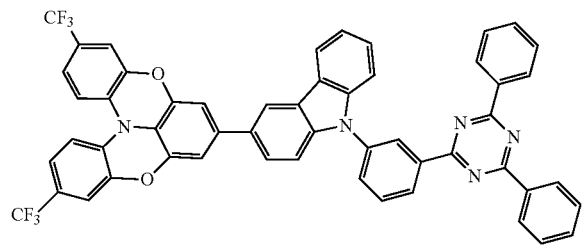
69
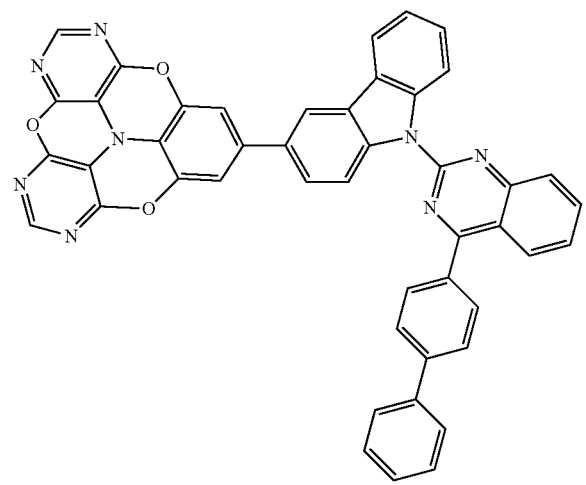
70
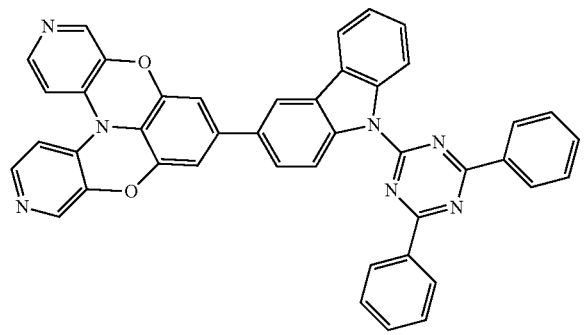
71
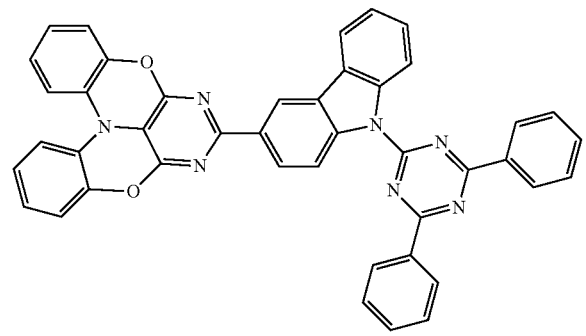
72
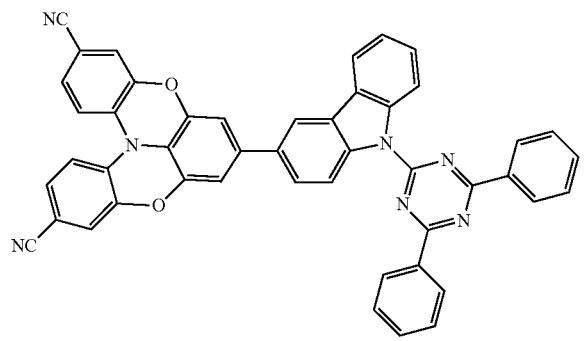
73
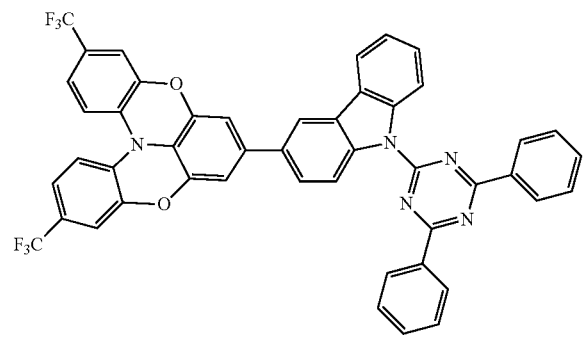
74
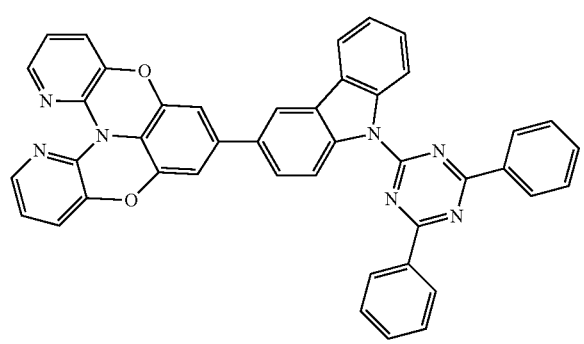
75
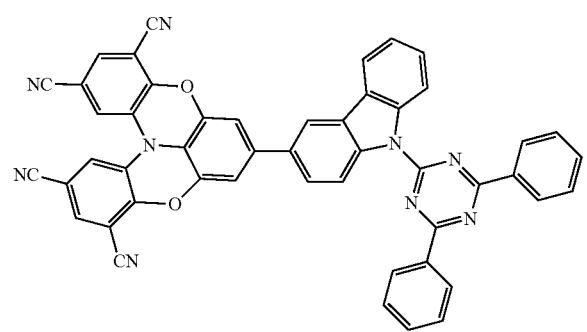

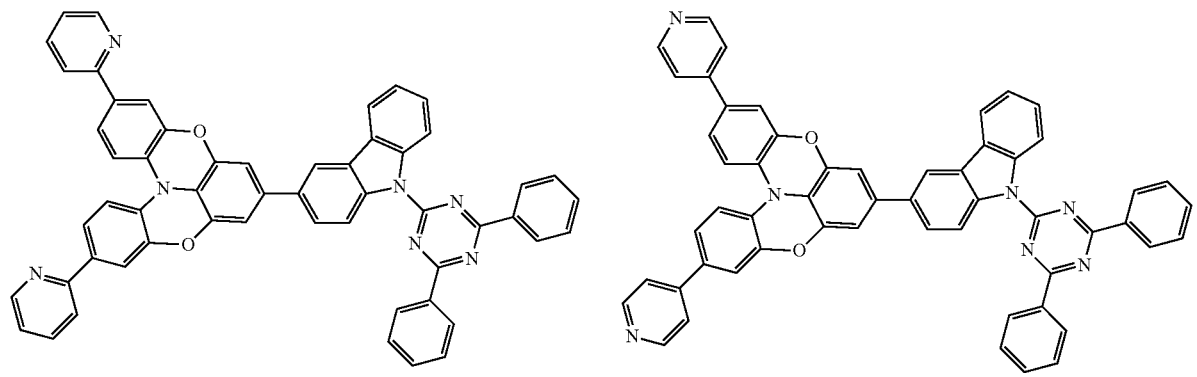

The compounds of the formula (I) can be prepared by customary methods of synthetic organic chemistry that are known to those skilled in the art. In the preparation of the compounds, transition metal-catalyzed coupling reactions in particular are used, such as halogenation reactions and Suzuki coupling reactions.

In the preparation of the compounds, the bridged triphenylamine group bearing a reactive group is preferably prepared first (schemes 1-5). Alternatively, many of these intermediates can also be obtained commercially.

Scheme 1 below shows by way of example how a triphenylamine group bridged with three oxygen bridges and bearing a bromine atom in the para position to the central amine group can be prepared.

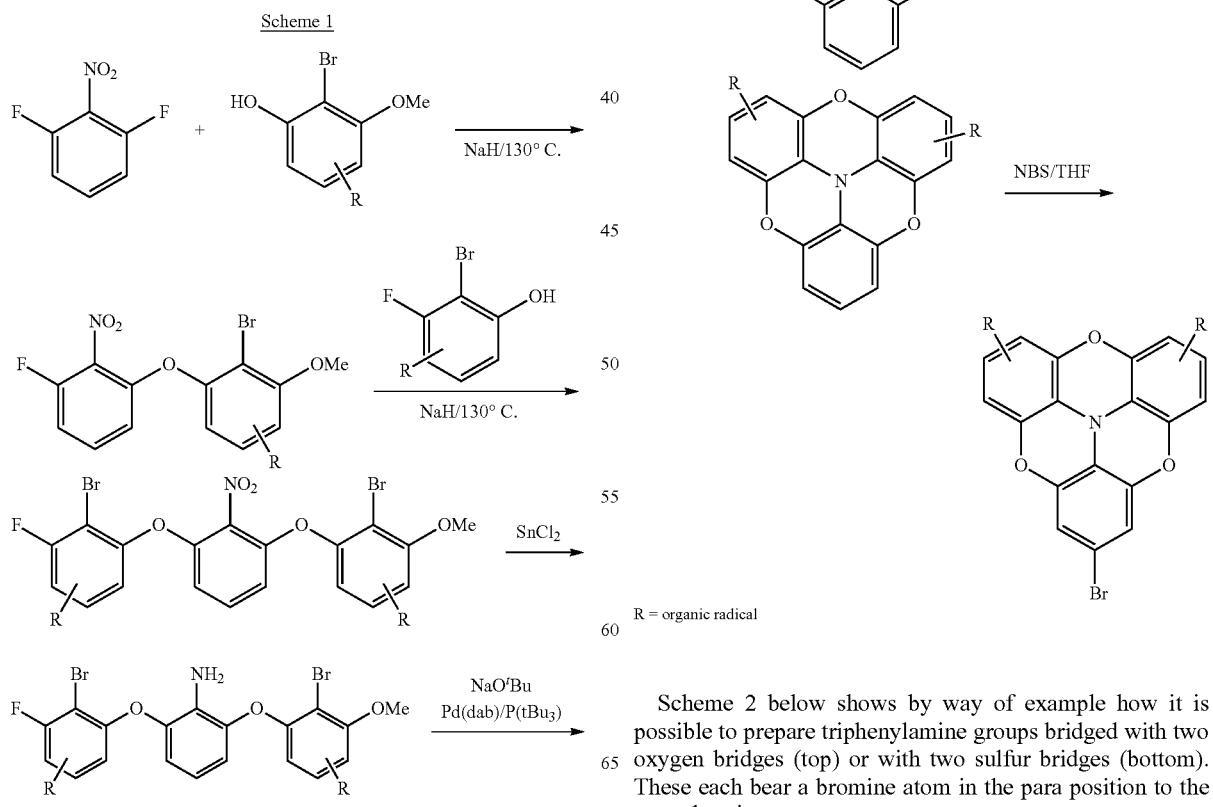

R = organic radical

Scheme 2 below shows by way of example how it is possible to prepare triphenylamine groups bridged with two oxygen bridges (top) or with two sulfur bridges (bottom). These each bear a bromine atom in the para position to the central amine group.

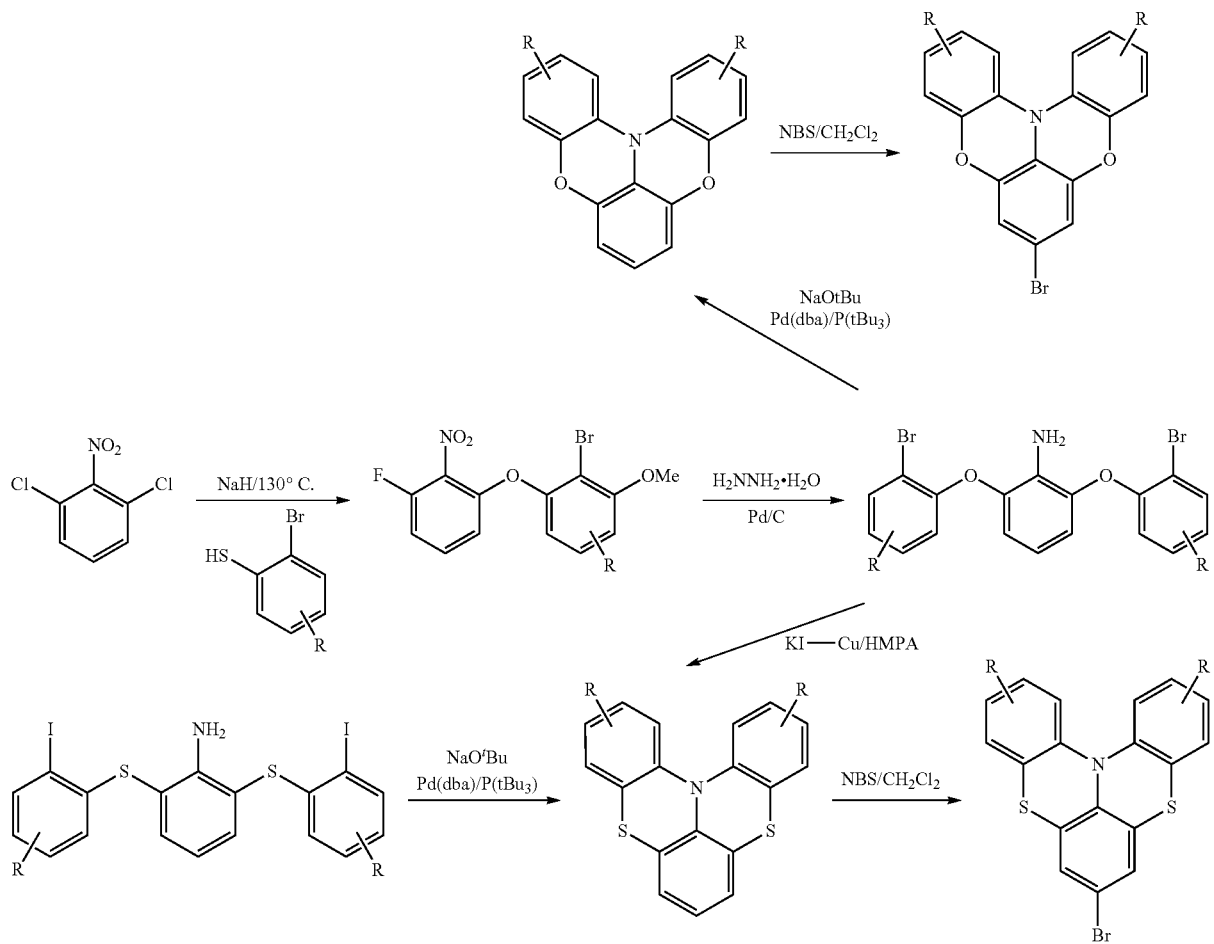
R = organic radical
Scheme 3 shows two routes to the triphenylamine groups bridged with two oxygen bridges, which can be used as an alternative to the route shown above in scheme 2.
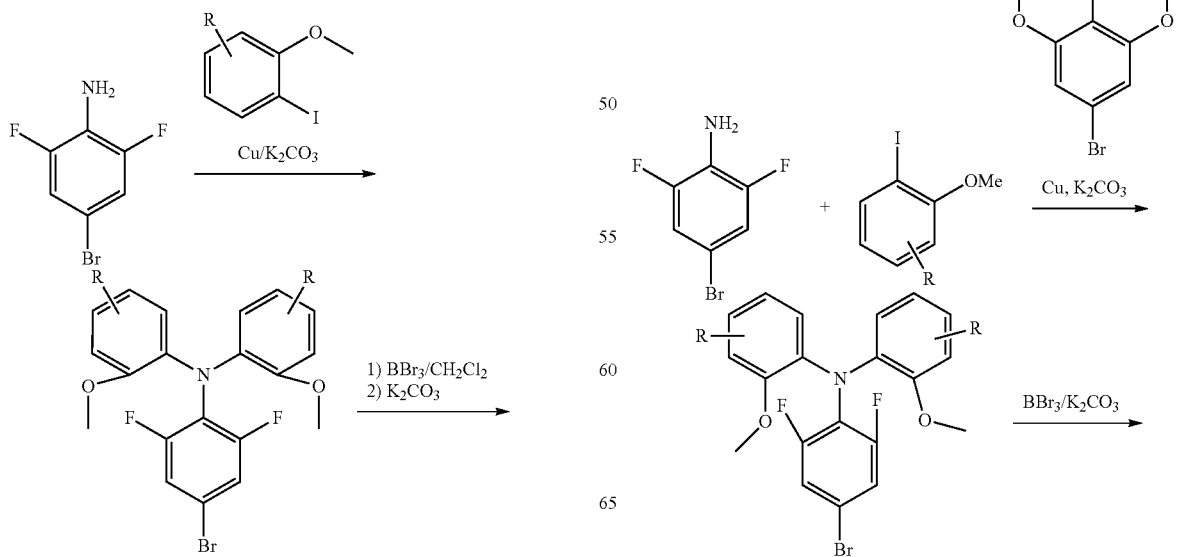

-continued

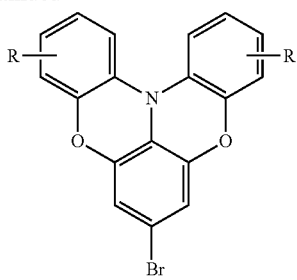

R = organic radical

Scheme 4 shows a route by which a triphenylamine group bridged with two oxygen bridges, having asymmetric substitution and bearing a bromine atom in the para position to the central amine group can be prepared.

Scheme 4

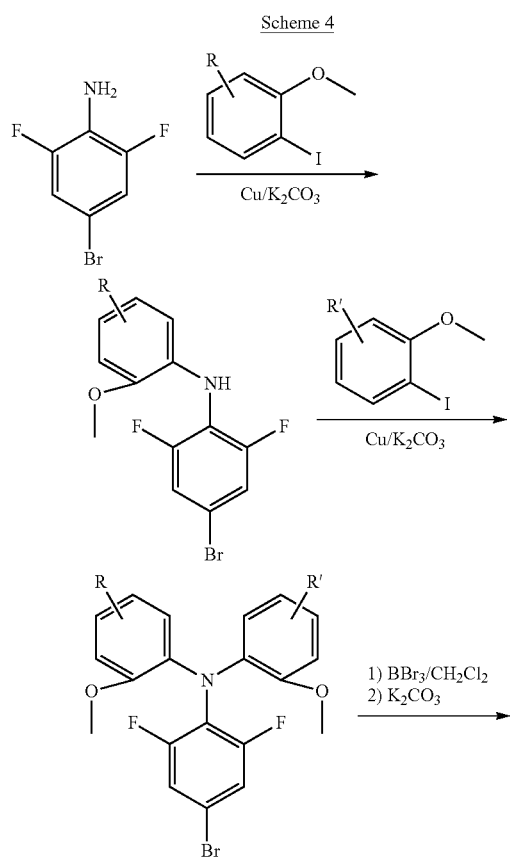

R = organic radical
R' = organic radical

Scheme 5 shows a synthesis for triphenylamine groups bridged with two oxygen bridges and bearing a bromine atom on a different phenyl group than is the case in the examples of schemes 2 to 4.

Scheme 5

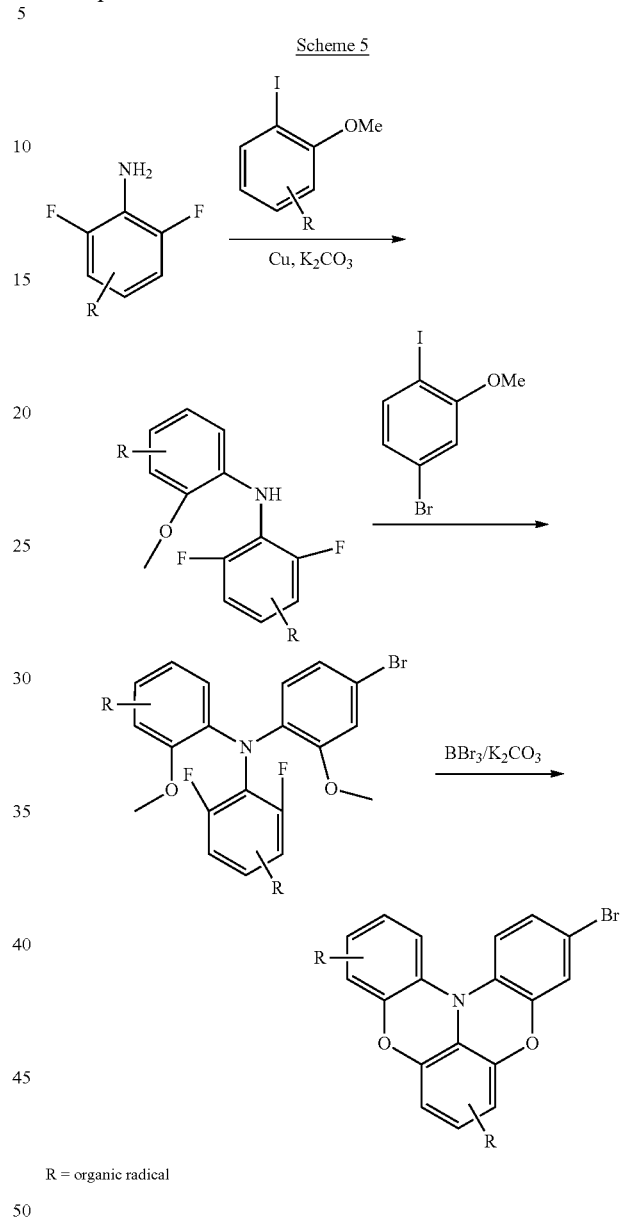

R = organic radical

After the preparation of the bridged triarylamine group bearing a reactive group, preferably a halogen atom, more preferably bromine, a carbazole derivative is bonded to the bridged triarylamine group in a Suzuki coupling (scheme 6).

Scheme 6

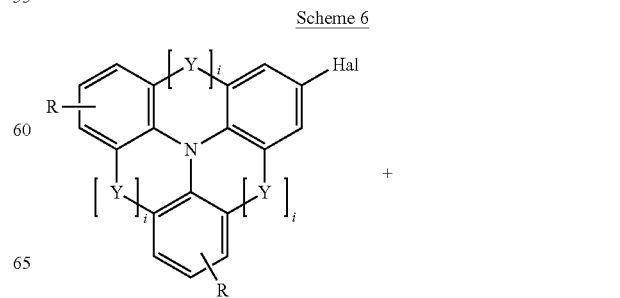

+

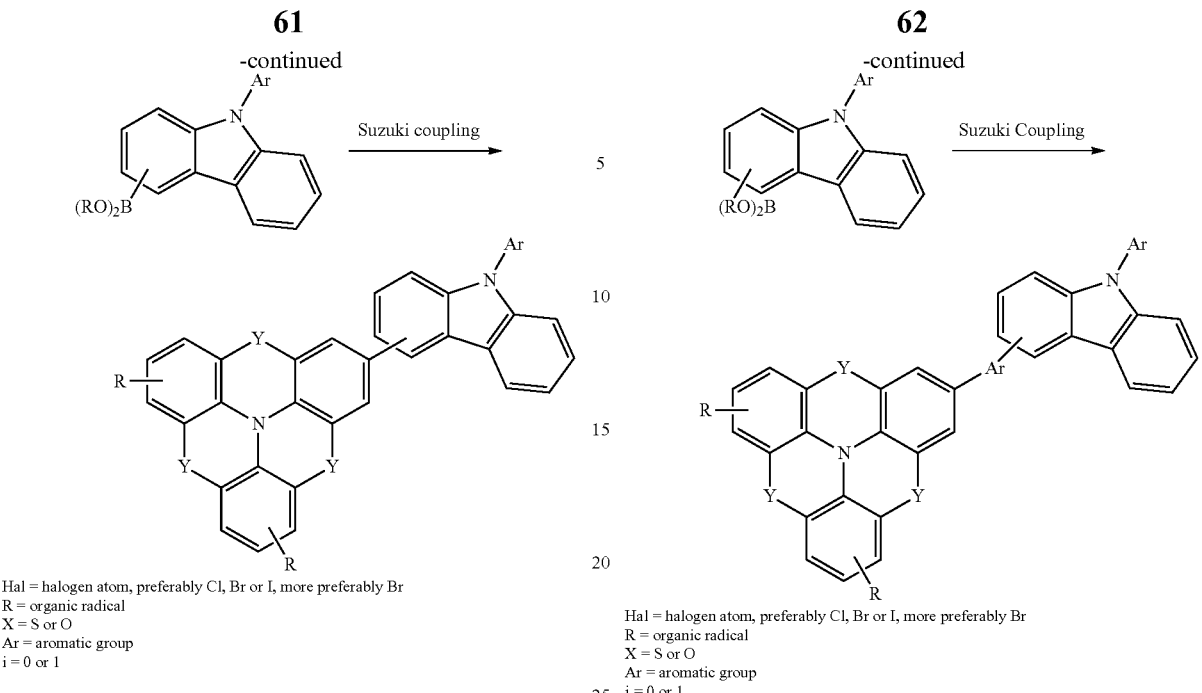

Hal = halogen atom, preferably Cl, Br or I, more preferably Br
R = organic radical
X = S or O
Ar = aromatic group
i = 0 or 1

In an alternative embodiment to scheme 6 (scheme 7), an aromatic group bearing a reactive group, preferably a halogen atom, is bonded to the bridged triarylamine group bearing a reactive group, preferably a halogen atom, more preferably bromine, in a Suzuki reaction. In a further step, a carbazole derivative is then attached in a further Suzuki reaction.

Scheme 7

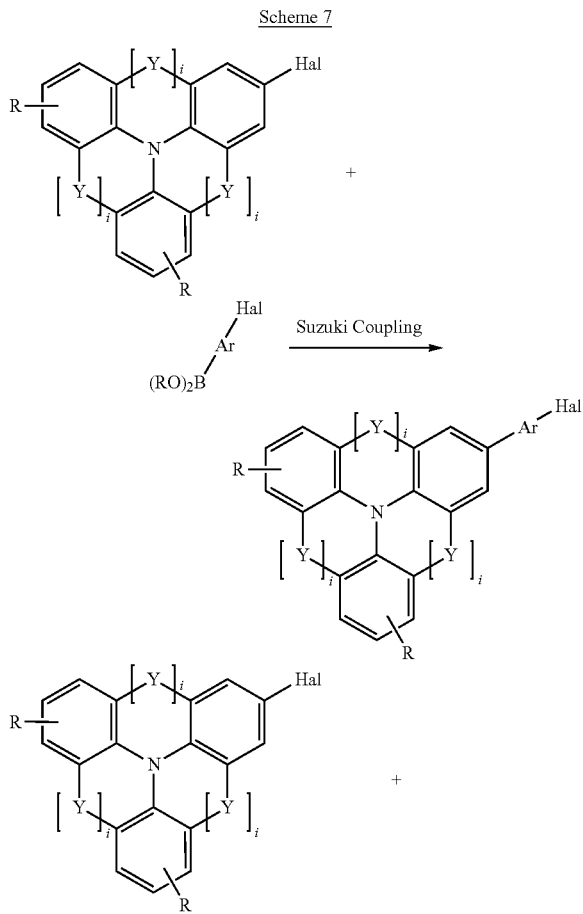

The compounds obtained can optionally be further modified and/or substituted in subsequent reactions.

The present invention thus provides a process for preparing a compound of the formula (I) as defined above, characterized in that, in a first step, a triphenylamine compound substituted by a reactive group on one of the phenyl groups is prepared, where the bridges between the phenyl groups are selected from single bond, O and S, and where at least 2 bridges are present, and in that, in a further step, a carbazole group is introduced into the compound via a transition metal-catalyzed coupling reaction.

The reactive group is preferably selected from halogen, more preferably bromine. The reaction in the further step is preferably a Suzuki coupling reaction. The carbazole group preferably has a reactive group, more preferably a boronic acid or a derivative of boronic acid, for example a boronic ester.

The above-described compounds, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (I), wherein the bond(s) to the polymer, oligomer or dendrimer may be localized at any desired positions substituted by $R^1$, $R^2$, $R^3$ or $R^4$ in formula (I). According to the linkage of the compound of formula (I), the compound is part of a side chain of the oligomer or polymer or part of the main chain. An oligomer in the context of this invention is understood to mean a compound formed from at least three monomer units. A polymer in the context of the invention is understood to mean a compound formed from at least ten monomer units. The polymers, oligomers or dendrimers of the invention may be conjugated, partly conjugated or nonconjugated. The oligomers or polymers of the invention may be linear, branched or dendritic. In the structures having linear linkage, the units of formula (I) may be joined directly to one another, or they may be joined to one another via a bivalent group, for example via a substituted or unsubstituted alkylene group, via a heteroatom or via a bivalent aromatic or heteroaromatic group. In branched and dendritic structures, it is possible, for example, for three or more units of formula (I) to be joined via a trivalent or higher-valency group, for example via a trivalent or higher-valency aromatic or heteroaromatic group, to give a branched or dendritic oligomer or polymer.

For the repeat units of formula (I) in oligomers, dendrimers and polymers, the same preferences apply as described above for compounds of formula (I).

For preparation of the oligomers or polymers, the monomers of the invention are homopolymerized or copolymerized with further monomers. Suitable and preferred comonomers are selected from fluorenes (for example according to EP 842208 or WO 2000/22026), spirobifluorenes (for example according to EP 707020, EP 894107 or WO 2006/061181), paraphenylenes (for example according to WO 1992/18552), carbazoles (for example according to WO 2004/070772 or WO 2004/113468), thiophenes (for example according to EP 1028136), dihydrophenanthrenes (for example according to WO 2005/014689 or WO 2007/006383), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers typically contain still further units, for example emitting (fluorescent or phosphorescent) units, for example vinyltriarylamines (for example according to WO 2007/068325) or phosphorescent metal complexes (for example according to WO 2006/003000), and/or charge transport units, especially those based on triarylamines.

The polymers and oligomers of the invention are generally prepared by polymerization of one or more monomer types, of which at least one monomer leads to repeat units of the formula (I) in the polymer. Suitable polymerization reactions are known to those skilled in the art and are described in the literature. Particularly suitable and preferred polymerization reactions which lead to formation of C—C or C—N bonds are the Suzuki polymerization, the Yamamoto polymerization, the Stille polymerization and the Hartwig-Buchwald polymerization.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising at least one compound of formula (I) and at least one solvent, preferably an organic solvent. The way in which such solutions can be prepared is known to those skilled in the art and is described, for example, in WO 2002/072714, WO 2003/019694 and the literature cited therein.

The compounds of the invention are suitable for use in electronic devices, especially in organic electroluminescent devices (OLEDs). Depending on the substitution, the compounds are used in different functions and layers.

The invention therefore further provides for the use of the compound of formula (I) in an electronic device. This electronic device is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and more preferably organic electroluminescent devices (OLEDs).

The invention further provides, as already set out above, an electronic device comprising at least one compound of formula (I). This electronic device is preferably selected from the abovementioned devices.

It is more preferably an organic electroluminescent device (OLED) comprising anode, cathode and at least one emitting layer, characterized in that at least one organic layer, which may be an emitting layer, an electron transport layer, a hole blocker layer or another layer, comprises at least one compound of formula (I).

Apart from the cathode, anode and emitting layer, the organic electroluminescent device may also comprise further layers. These are selected, for example, from in each case one or more hole injection layers, hole transport layers, hole blocker layers, electron transport layers, electron injection layers, electron blocker layers, exciton blocker layers, interlayers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions.

The sequence of the layers of the organic electroluminescent device comprising the compound of the formula (I) is preferably as follows: anode-hole injection layer-hole transport layer-optionally further hole transport layer(s)-optionally electron blocker layer-emitting layer-optionally hole blocker layer-electron transport layer-electron injection layer-cathode. It is additionally possible for further layers to be present in the OLED.

The organic electroluminescent device of the invention may contain two or more emitting layers. More preferably, these emission layers in this case have several emission maxima between 380 nm and 750 nm overall, such that the overall result is white emission; in other words, various emitting compounds which may fluoresce or phosphoresce and which emit blue, green, yellow, orange or red light are used in the emitting layers. Especially preferred are three-layer systems, i.e. systems having three emitting layers, where the three layers show blue, green and orange or red emission (for the basic construction see, for example, WO 2005/011013). The compounds of the invention are preferably present in the emitting layer or the hole transport layer.

It is preferable in accordance with the invention when the compound of formula (I) is used in an electronic device comprising one or more phosphorescent emitting compounds. In this case, the compound may be present in different layers, preferably in an electron transport layer or in an emitting layer. More preferably, it is present in an emitting layer in combination with a phosphorescent emitting compound.

The term "phosphorescent emitting compounds" typically encompasses compounds where the emission of light is effected through a spin-forbidden transition, for example a transition from an excited triplet state or a state having a higher spin quantum number, for example a quintet state.

Suitable phosphorescent emitting compounds (=triplet emitters) are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent emitting compounds, compounds containing copper, molybdenum, tungsten, rhenium, ruthenium, osmium, rhodium, iridium, palladium, platinum, silver, gold or europium, especially compounds containing iridium, platinum or copper. In the context of the present invention, all luminescent iridium, platinum or copper complexes are considered to be phosphorescent emitting compounds.

Examples of the above-described emitting compounds can be found in applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used for phosphorescent OLEDs according to the prior art and as known to those skilled in the art in the field of organic electroluminescent devices are suitable. It is also possible for the person skilled in the art, without exercising inventive skill, to use further phosphorescent complexes in combination with the compounds of formula (I) in organic electroluminescent devices. Further examples are listed in a table which follows.

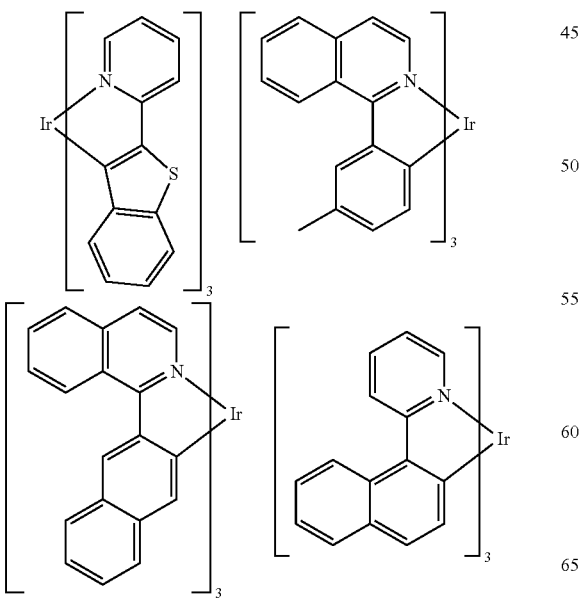

-continued

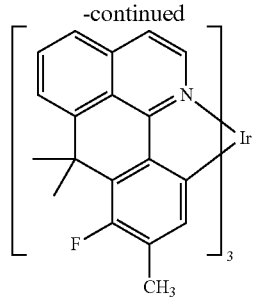

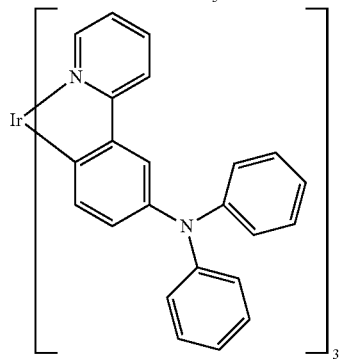

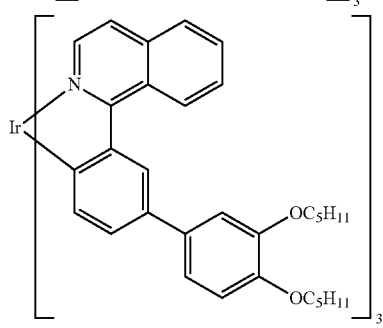

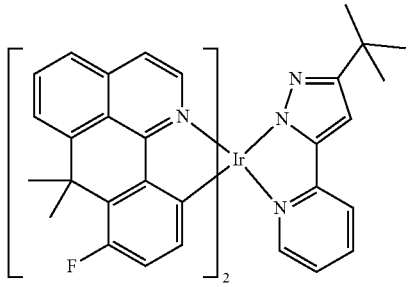

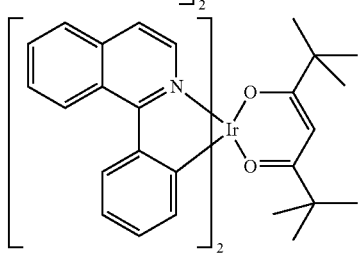

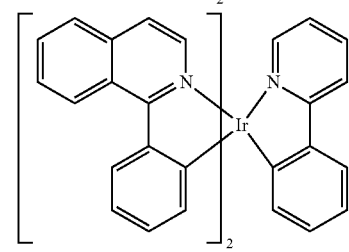

-continued
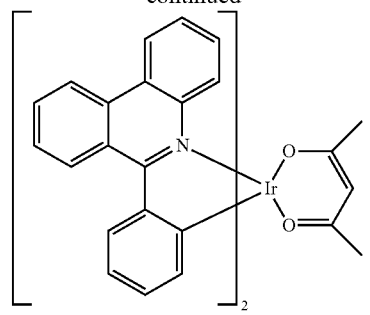
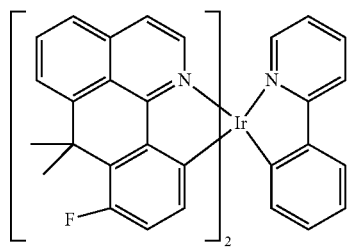
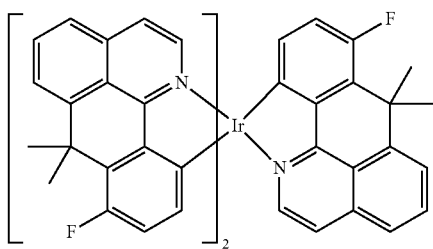
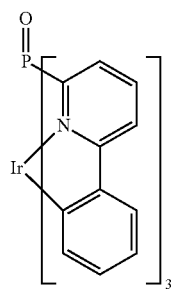
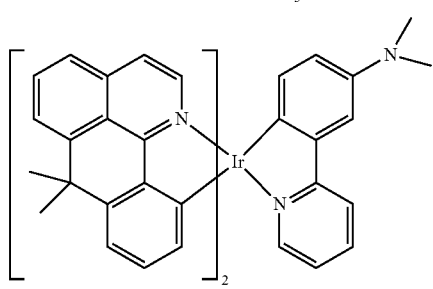
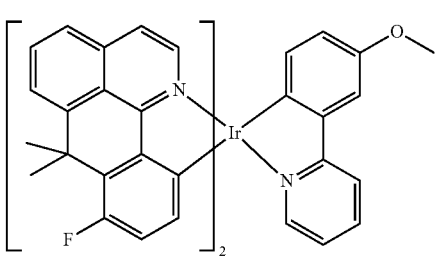
-continued
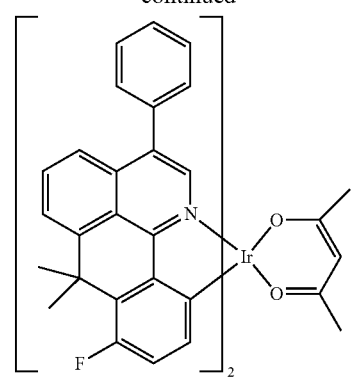
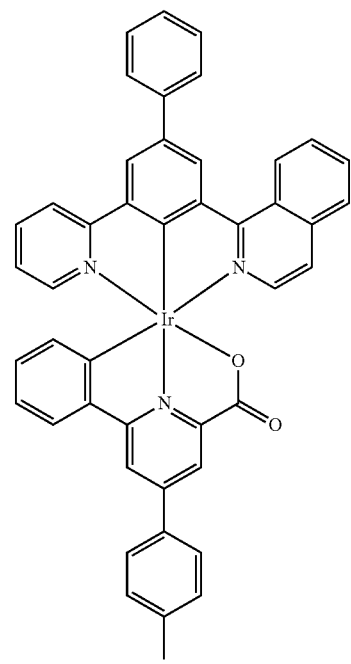
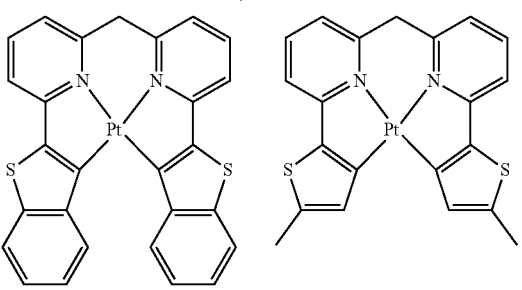
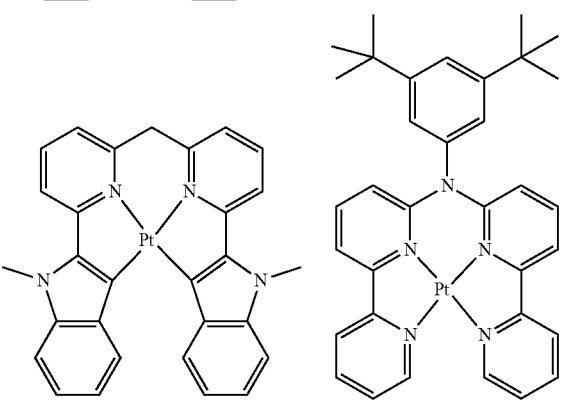

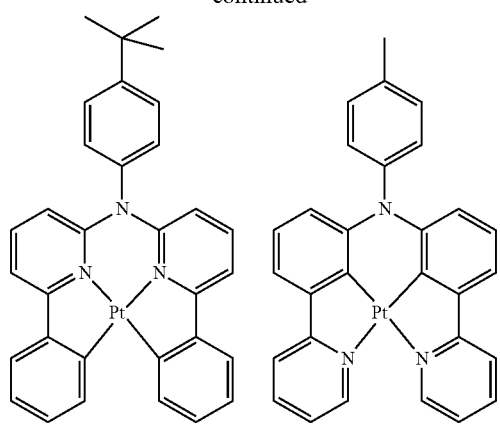
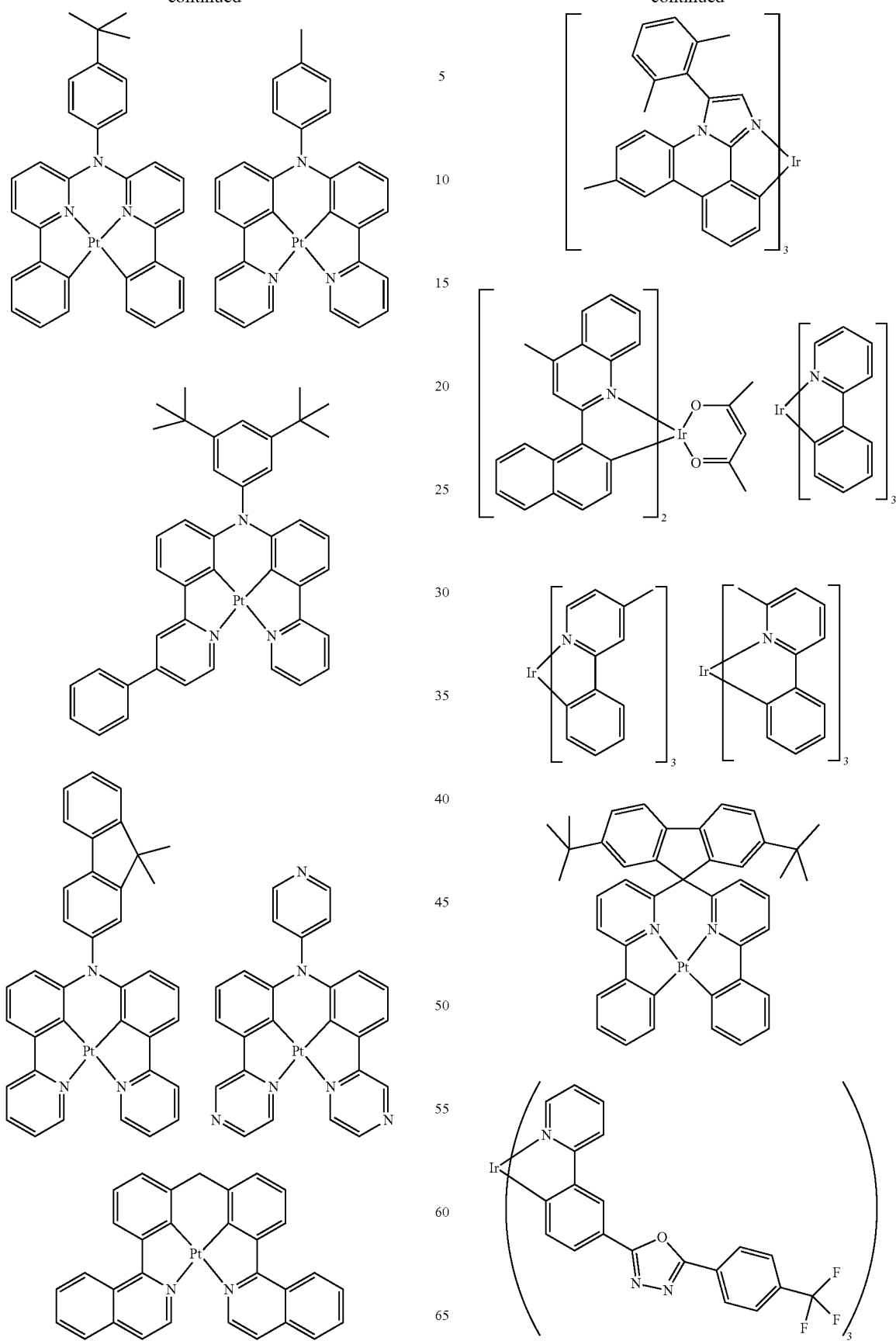

71
-continued
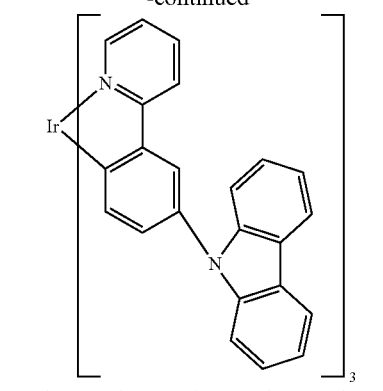
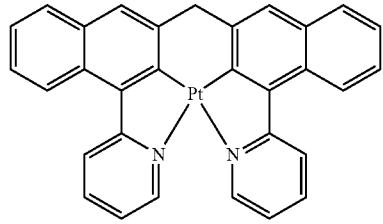
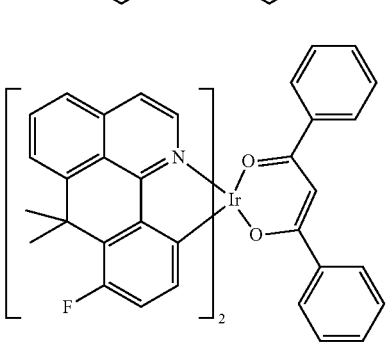
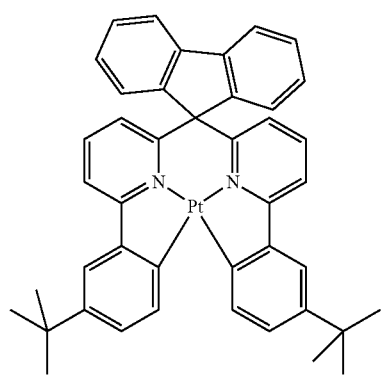
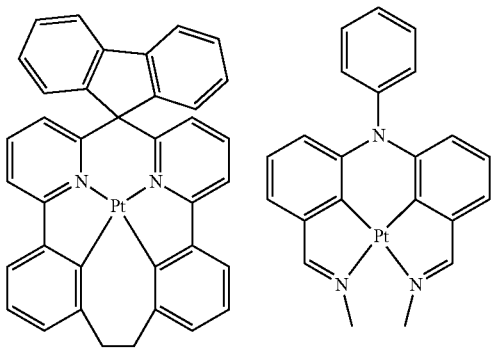
72
-continued
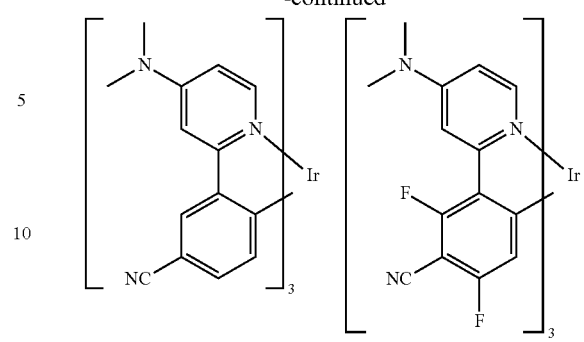
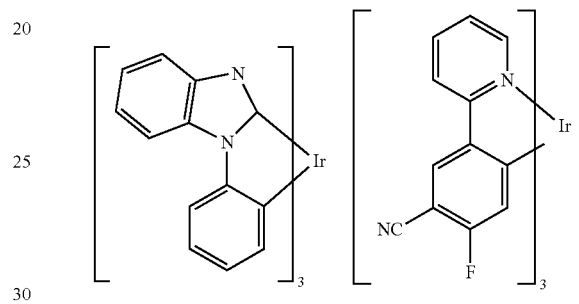
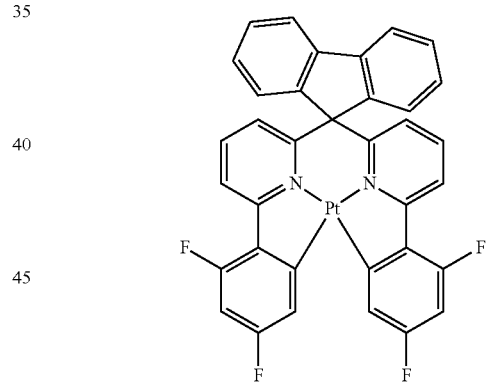
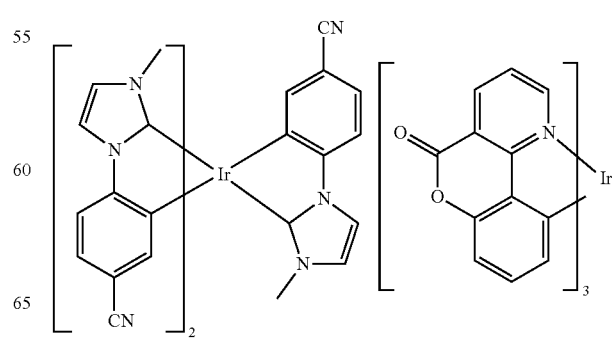

-continued
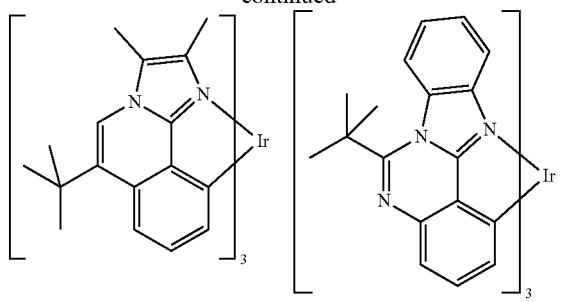
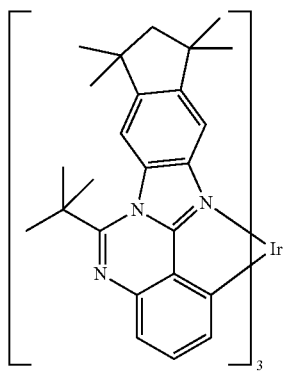
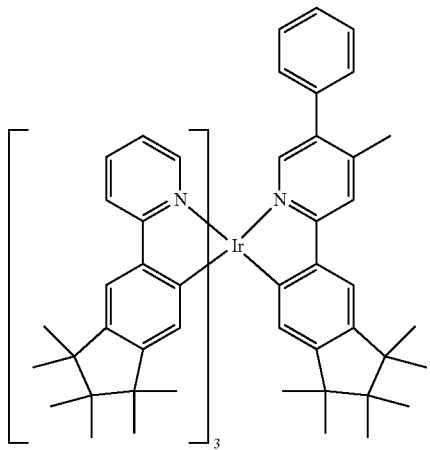
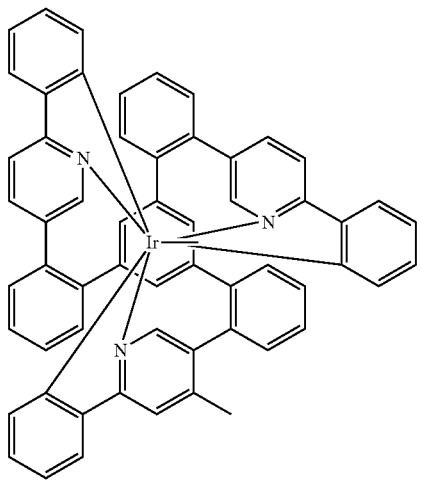
-continued
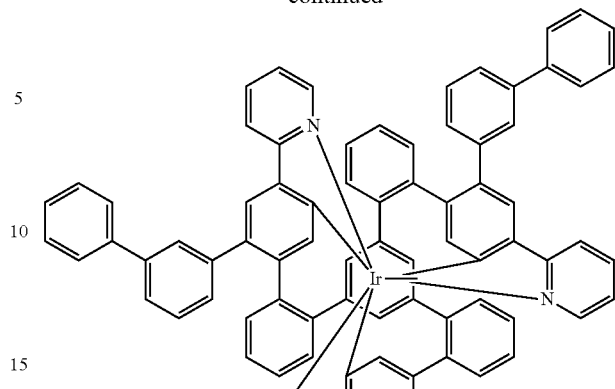
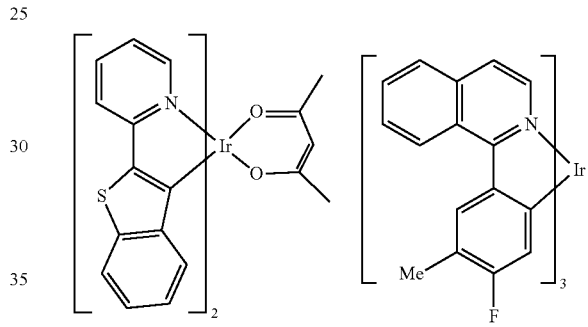
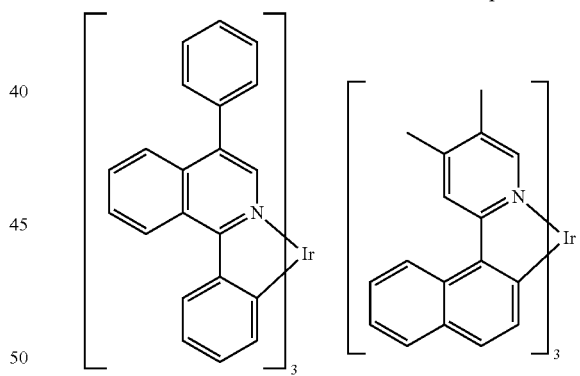
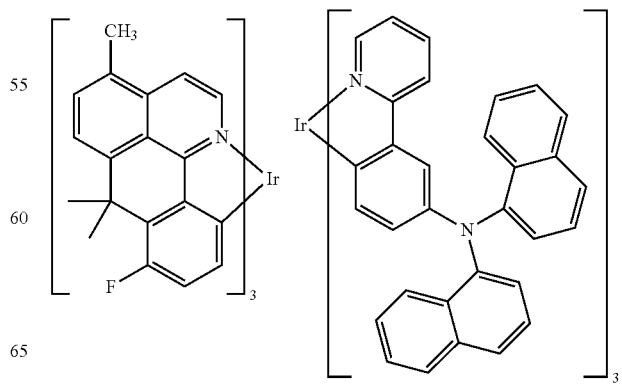

75
-continued
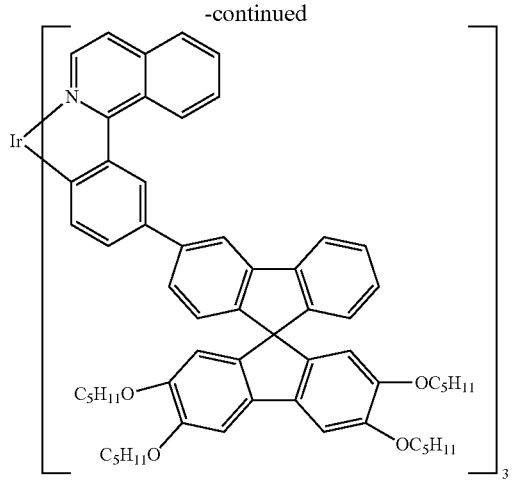
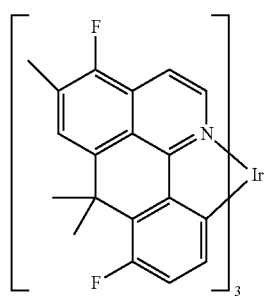
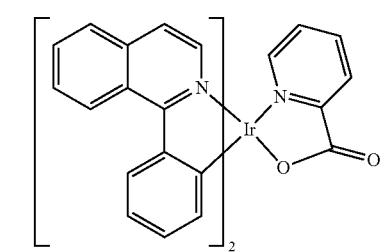
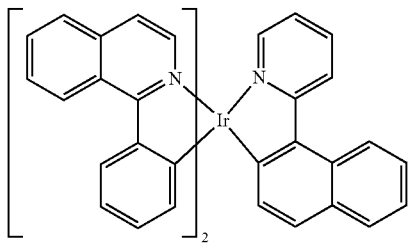
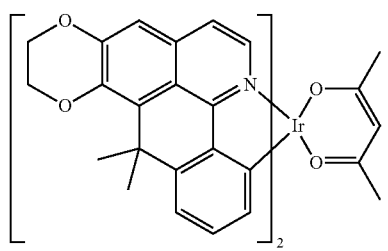
76
-continued
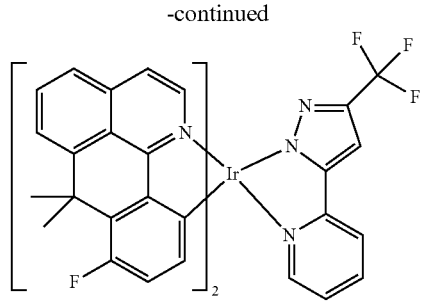
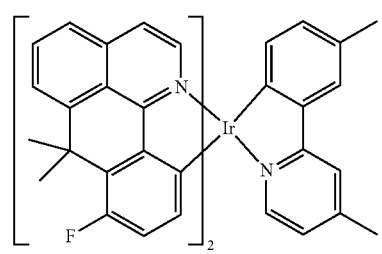
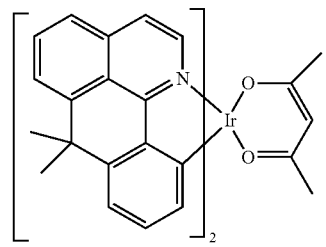
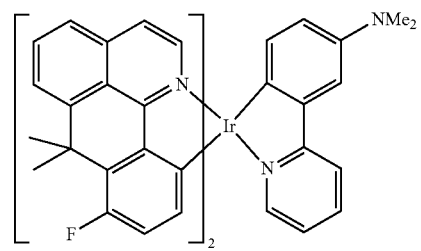
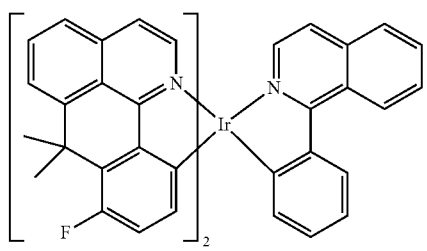

-continued
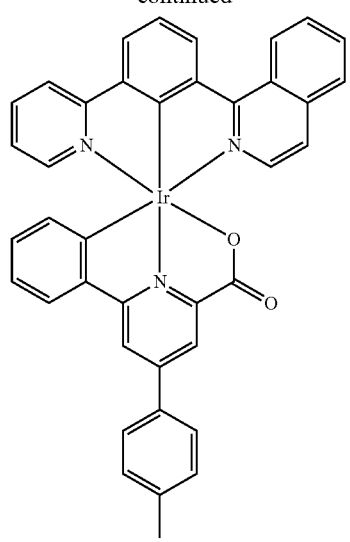
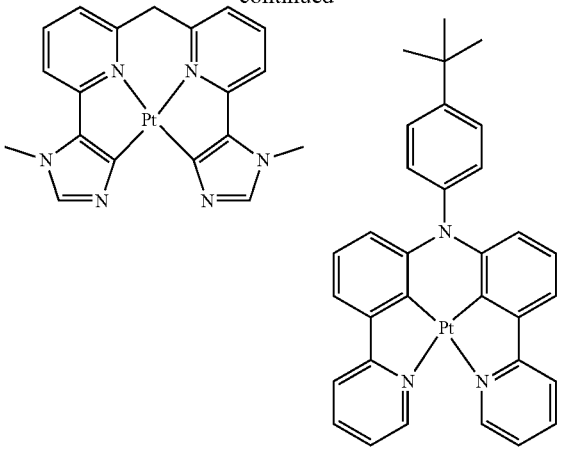
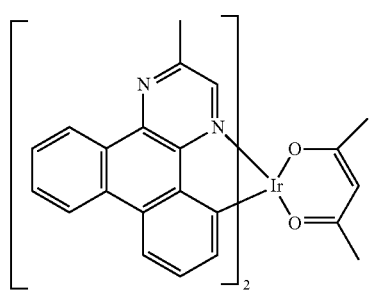
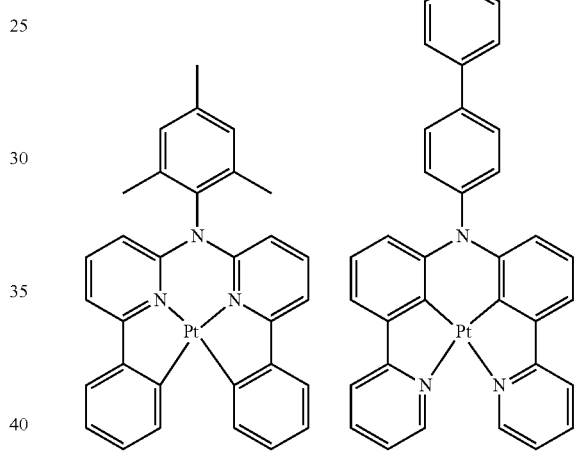
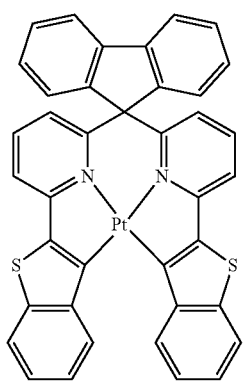
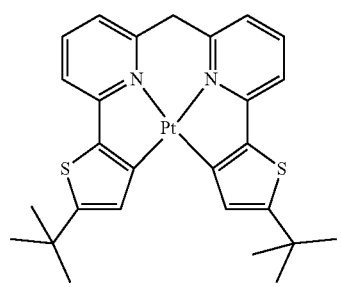
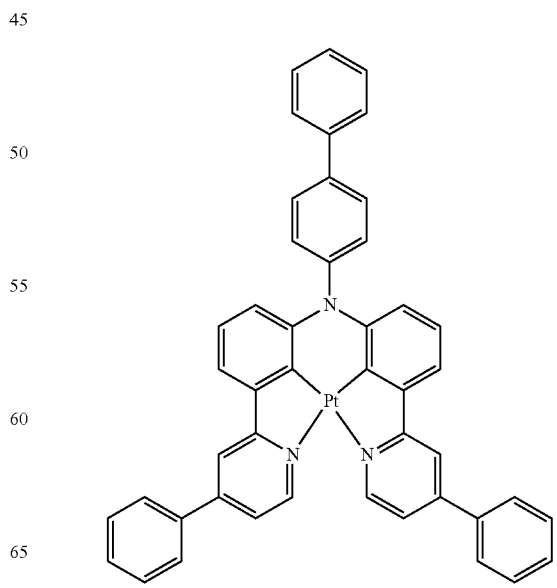

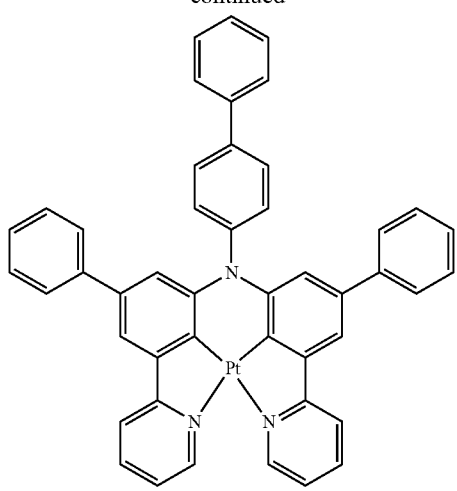
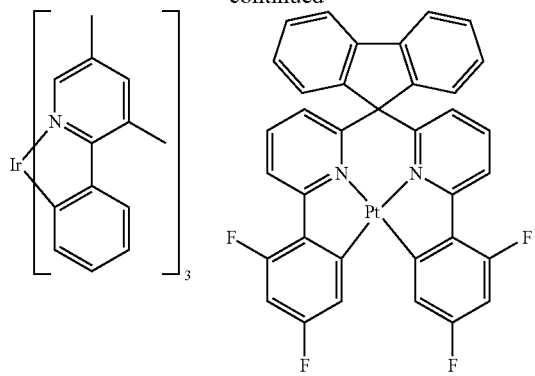
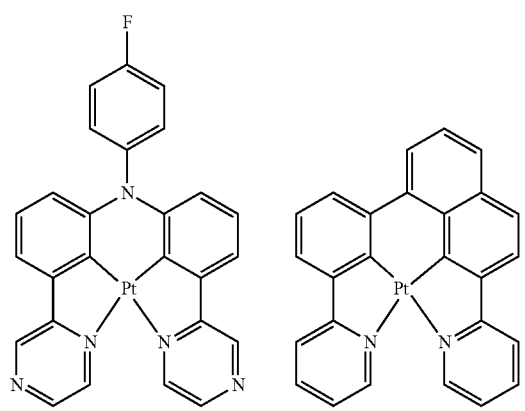
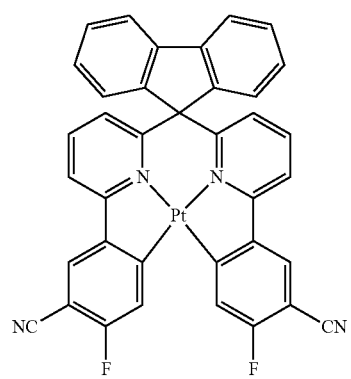
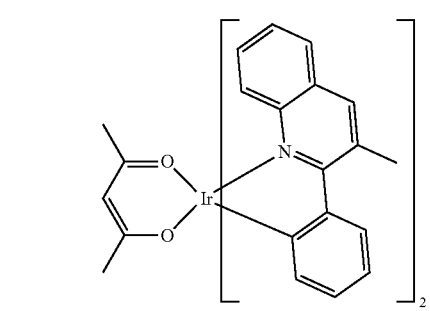
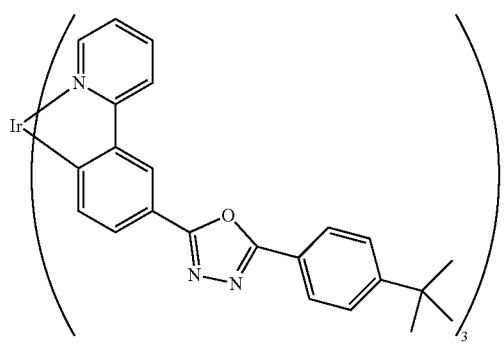
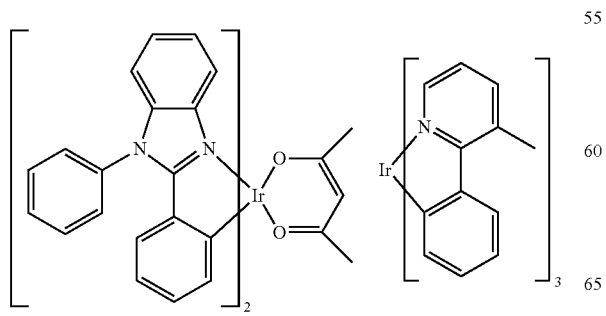
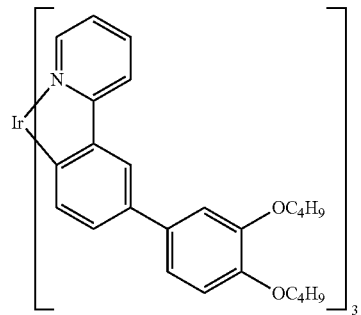

-continued
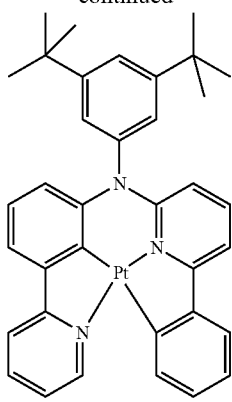
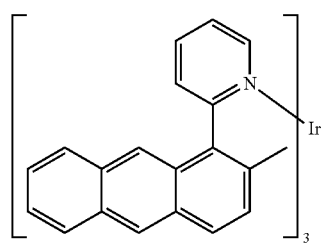
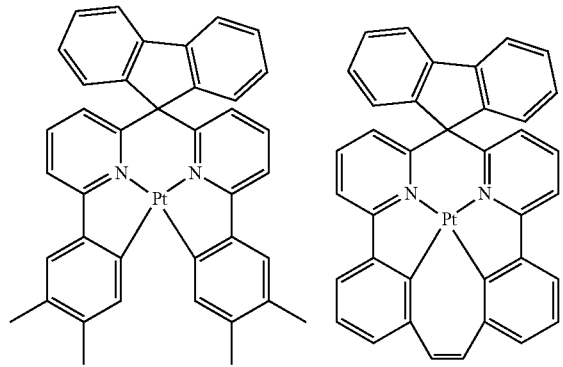
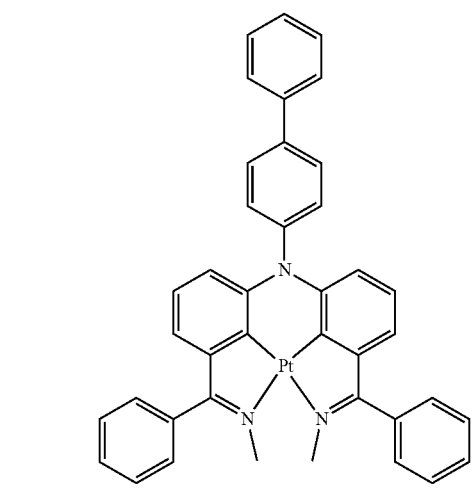
-continued
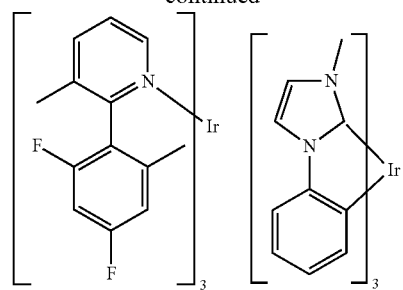
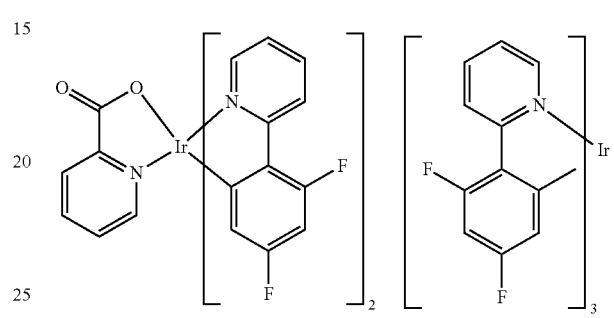
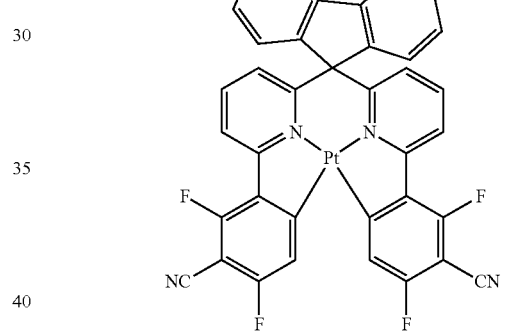
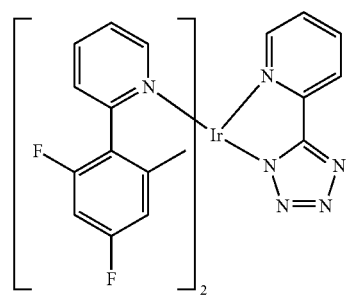
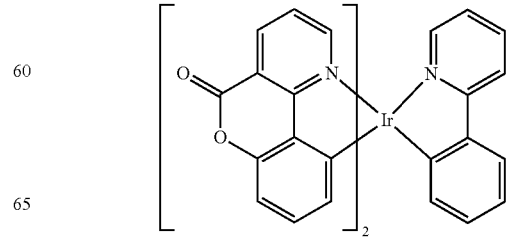

83
-continued
84
-continued
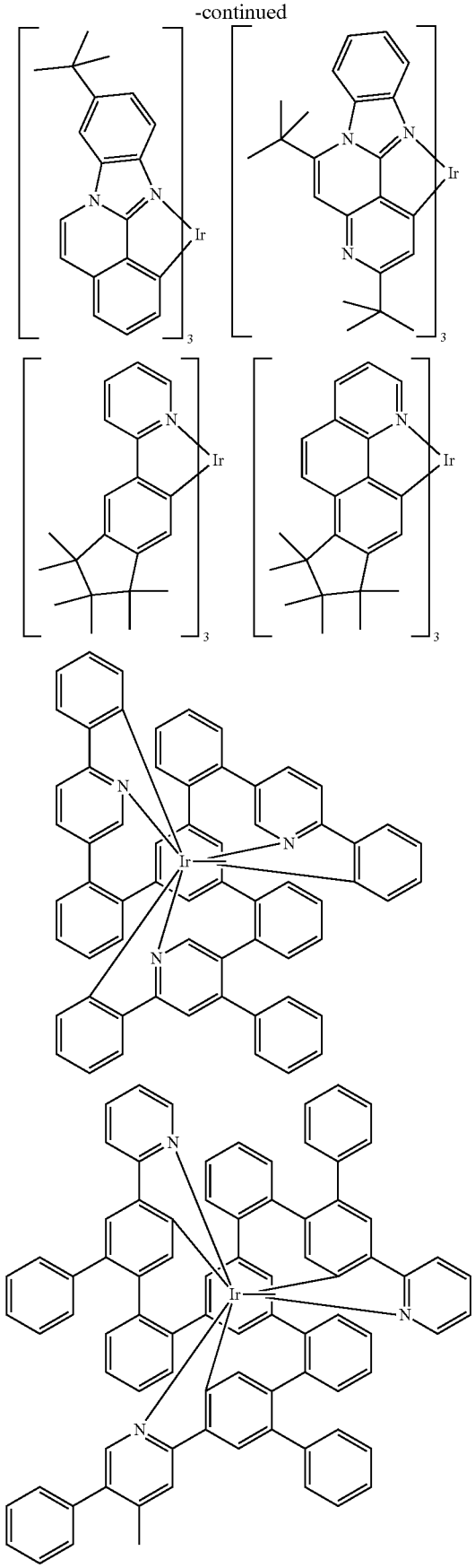
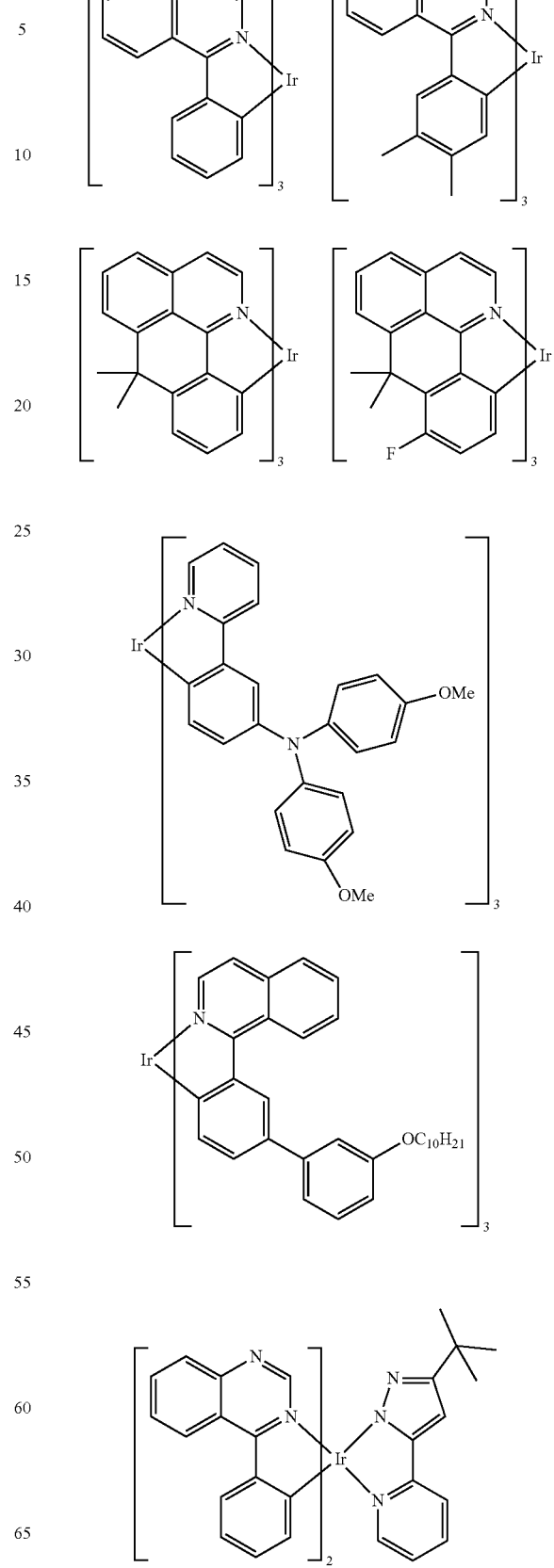

85
-continued
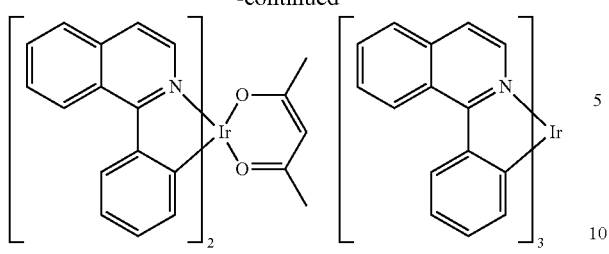
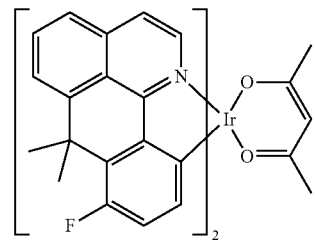
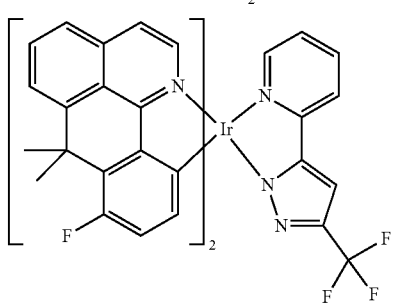
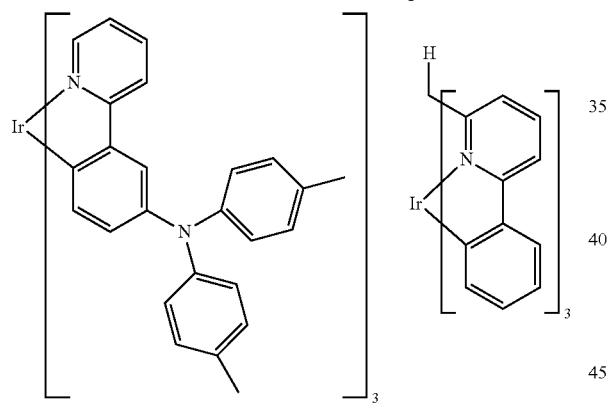
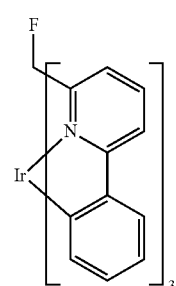
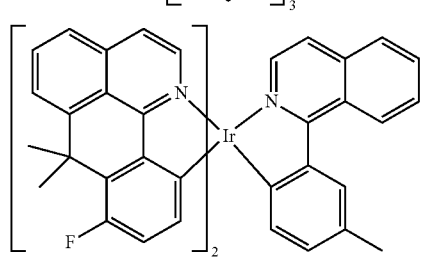
86
-continued
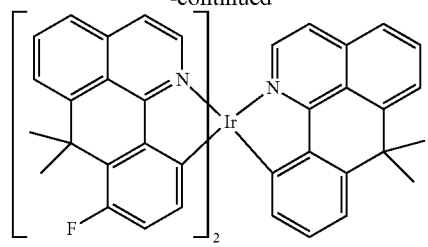
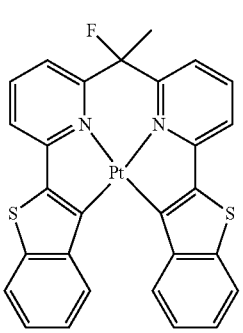
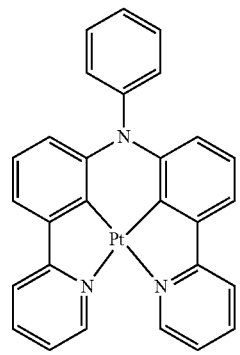
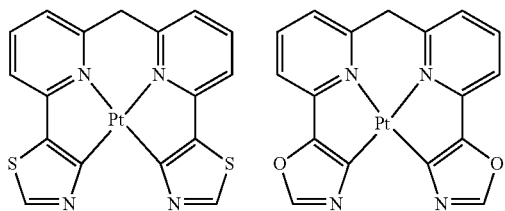
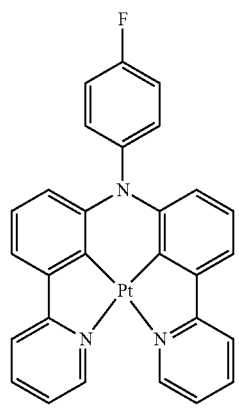

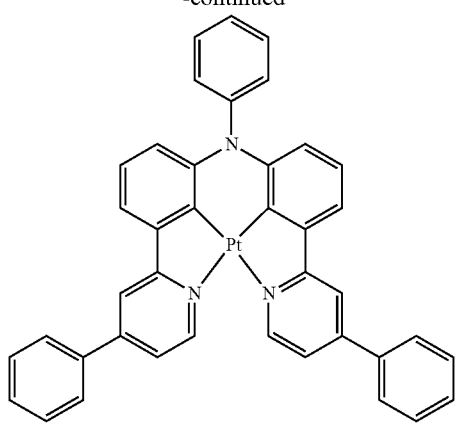
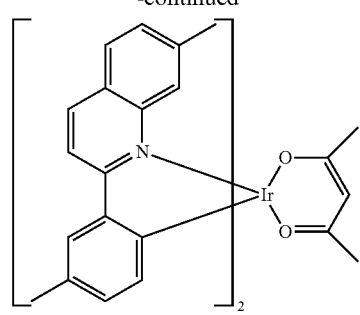
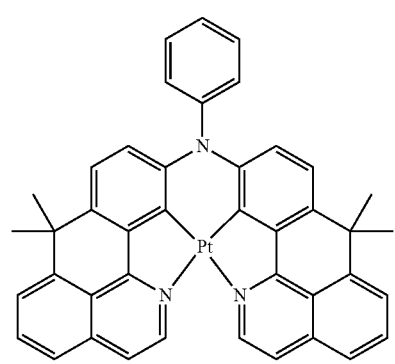
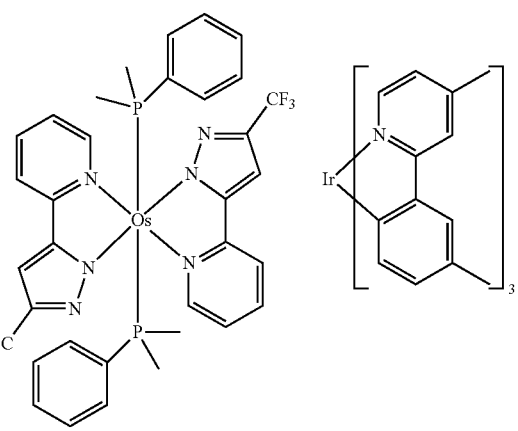
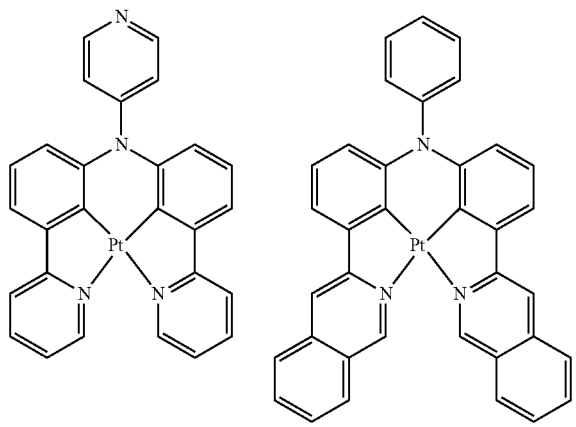
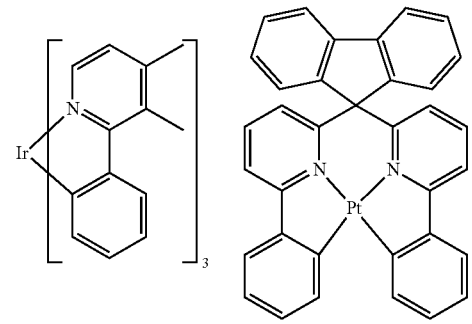
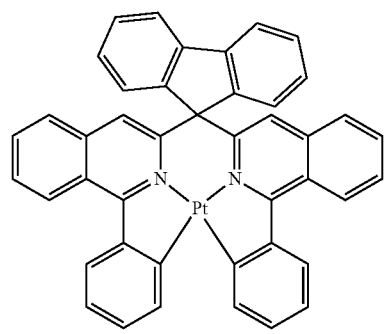
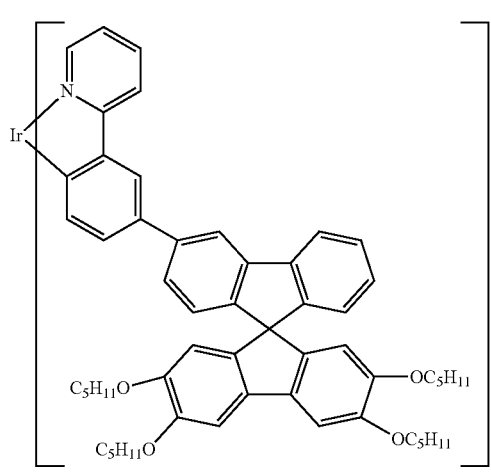

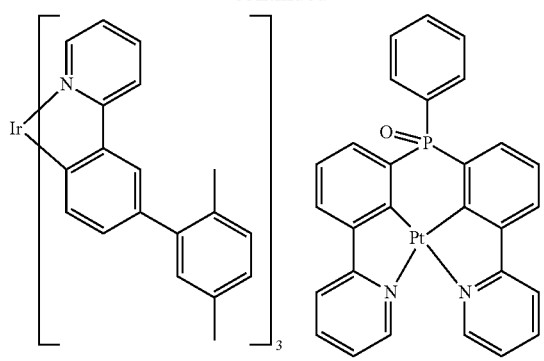
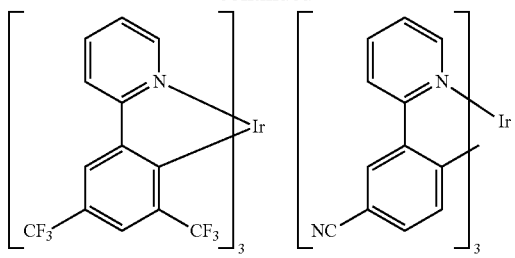
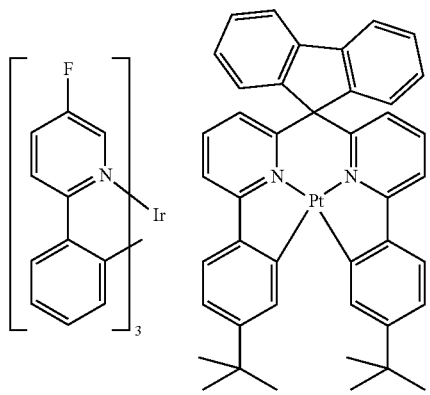
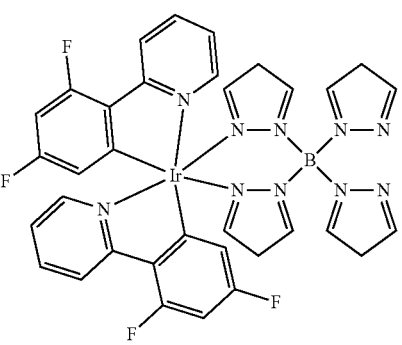
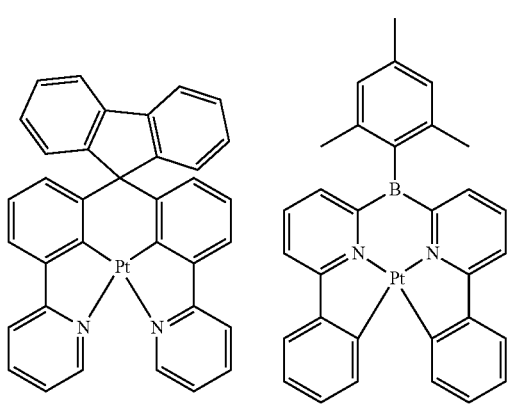
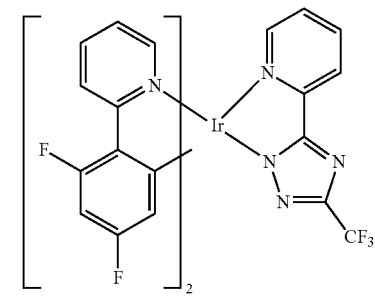
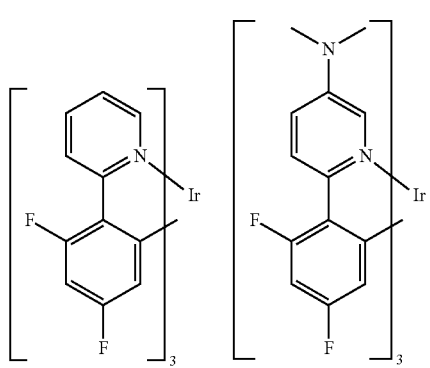
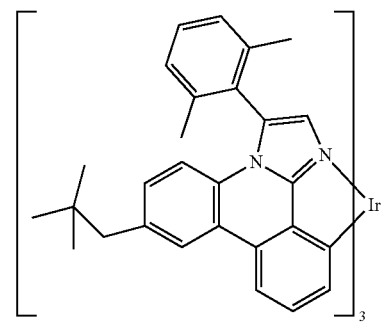
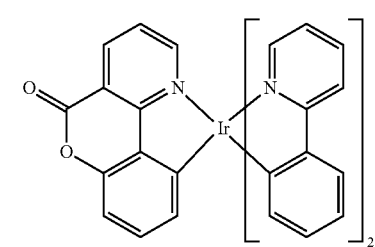

-continued

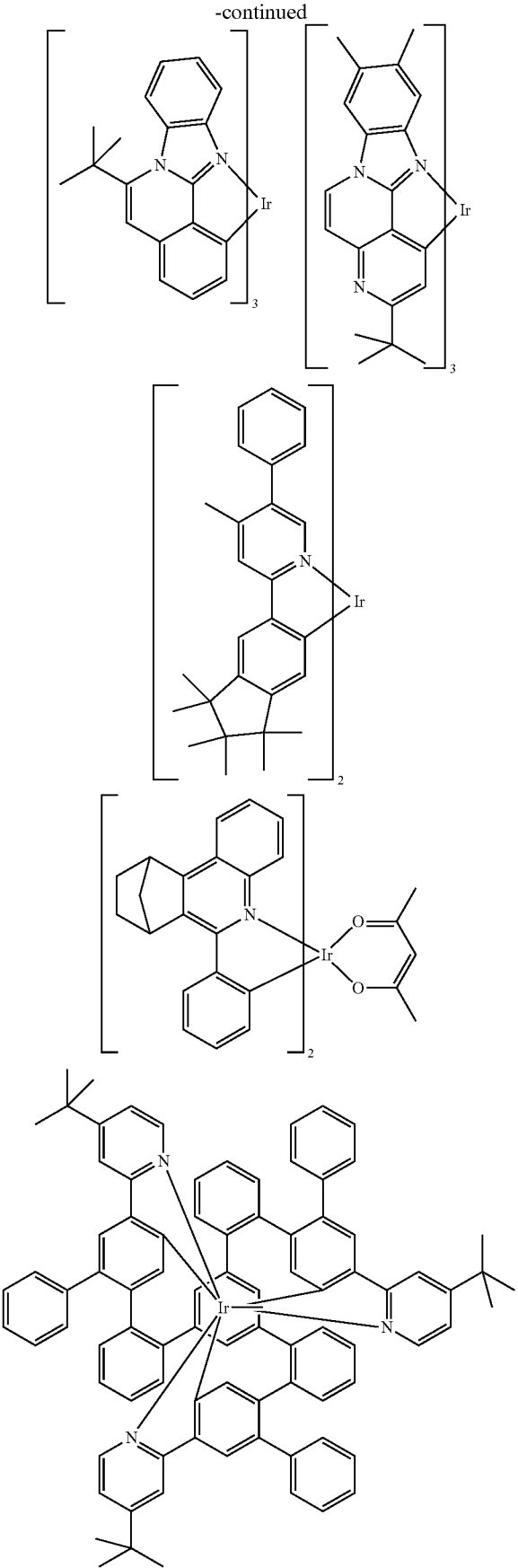

-continued

In a preferred embodiment of the present invention, the compound of the formula (I) is used in an emitting layer as matrix material in combination with one or more emitting compounds, preferably phosphorescent emitting compounds. The phosphorescent emitting compound is preferably a red- or green-phosphorescing emitter. This is the most strongly preferred use of the compounds of the formula (I).

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the emitting compound is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also contain systems comprising a plurality of matrix materials (mixed matrix systems) and/or a plurality of emitting compounds. In this case too, the emitting compounds are generally those compounds having the smaller proportion in the system and the matrix materials are those compounds having the greater proportion in the system. In individual cases, however, the proportion of a single matrix material in the system may be less than the proportion of a single emitting compound.

It is preferable that the compounds of formula (I) are used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The compound of the formula (I) is preferably the matrix material having hole-transporting properties. The desired electron-transporting and hole-transporting properties of the mixed matrix components may, however, also be combined mainly or entirely in a single mixed matrix component, in which case the further mixed matrix component(s) fulfill(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The mixed matrix systems may comprise one or more emitting compounds, preferably one or more phosphorescent emitting compounds. In general, mixed matrix systems are preferably used in phosphorescent organic electroluminescent devices.

Particularly suitable matrix materials which can be used in combination with the compounds of the invention as matrix components of a mixed matrix system are selected from the preferred matrix materials specified below for phosphorescent emitting compounds or the preferred matrix materials for fluorescent emitting compounds, according to what type of emitting compound is used in the mixed matrix system.

In an alternative preferred embodiment of the invention, the compounds of formula (I) are used as matrix material for emitter materials that exhibit TADF (thermally activated delayed fluorescence). Emitter materials of this kind are known to those skilled in the art. More particularly, it is possible to use the compounds shown in FIG. 1b) in H. Uoyama et al., Nature 2012, 492, 234 ff. as TADF emitter materials.

In an alternative preferred embodiment of the invention, the compounds of formula (I) are used as electron-transporting material. This is especially true when the compound of the formula (I) contains an electron-deficient heteroaryl group, for example triazinyl, pyrimidyl, pyrazinyl, pyridazinyl, pyridyl, benzimidazolyl, quinazolinyl, quinolinyl or phenanthrolinyl.

When the compounds are used as electron-transporting material, they are preferably used in a hole blocker layer, an electron transport layer or an electron injection layer. In a preferred embodiment, the layer mentioned is n-doped. Alternatively, the layer comprising the compound of the formula (I) may comprise this compound as pure material.

In the present context, an n-dopant is understood to mean an organic or inorganic compound capable of releasing electrons (electron donor), i.e. a compound that acts as a reducing agent.

The compounds used for n-doping can be used in the form of a precursor, in which case these precursor compounds release n-dopants through activation.

Preferably, n-dopants are selected from electron-rich metal complexes; P=N compounds; N-heterocycles, more preferably naphthylenecarbodiimides, pyridines, acridines and phenazines; fluorenes and free-radical compounds.

Particularly preferred electron-rich metal complexes are described inter alia in published specification WO 2005/86251 A2, which should be considered to form part of the present application for disclosure purposes. Among the electron-rich metal complexes, preference is given to uncharged electron-rich metal complexes.

Particularly preferred P=N compounds are disclosed inter alia in published specification WO 2012/175535 A1, which should be considered to form part of the present application for disclosure purposes.

A further group of n-dopants is that of N-heterocycles. N-Heterocycles are cyclic compounds having a ring structure that includes at least one nitrogen atom as well as hydrogen and carbon. These compounds may be saturated, partly unsaturated or heteroaromatic.

N-Heterocycles can preferably be used in the form of precursors, where precursor compounds have the feature that their effect as n-dopant sets in only after activation. Preferred N-heterocycles which can especially be used as precursors are described inter alia in published specification WO 2009/00237 A1, which should be considered to form part of the present application for disclosure purposes.

A further group of N-heterocycles suitable as n-dopants is that of naphthylenecarbodiimides. Naphthylenecarbodiimides comprise at least one carbodiimide group (N=C=N) and one naphthylene group.

Surprising advantages can be achieved by the naphthylenecarbodiimides described in published specification WO 2012/168358 A1, which should be considered to form part of the present application for disclosure purposes.

The preferred N-heterocycles usable as n-dopants also include pyridine derivatives, acridine derivatives and phenazine derivatives. These compounds comprise pyridine, acridine and phenazine structural elements and are known in the technical field. Preferred acridines and phenazines are detailed inter alia in published specification US 2007/0145355 A1, which should be considered to form part of the present application for disclosure purposes.

Surprising advantages can be achieved by the pyridines described in EP 2 452 946 A1 and EP 2 463 927 A1, which should be considered to form part of the present application for disclosure purposes.

In a particular configuration of the present invention, fluorenes can be used as n-dopants. Preferred fluorenes are described inter alia in published specification WO 2012/031735 A1, which should be considered to form part of the present application for disclosure purposes.

The preferred n-dopants include free-radical compounds that are known in the technical field. Preferred free-radical compounds comprise heterocyclic groups. Particularly preferred free-radical compounds are disclosed inter alia in EP 1 837 926 A1 and WO 2007/107306 A1, which should be considered to form part of the present application for disclosure purposes.

Of the n-dopants mentioned, particular preference is given to the electron-rich metal complexes disclosed in WO 2005/86251 A2, very particular preference to the metal complexes of the formula $W_2(hpp)_4$ where hpp is the anion of 1,3,4,6,7,8-hexahydro-2H-pyrimido[1,2-a]pyrimidine. Particular preference is given here to uncharged electron-rich metal complexes.

Preferred embodiments of the different functional materials in the electronic device are listed hereinafter.

Preferred fluorescent emitting compounds are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthraceneamines, aromatic anthracenediamines, aromatic pyreneamines, aromatic pyrenediamines, aromatic chryseneamines or aromatic chrysenediamines. An aromatic anthraceneamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyreneamines, pyrenediamines, chryseneamines and chrysenediamines are defined analogously, where the diarylamino groups are bonded to the pyrene preferably in the 1 position or 1,6 positions. Further preferred emitting compounds are indenofluoreneamines or -diamines, for example according to WO 2006/108497 or WO 2006/122630, benzoindenofluoreneamines or -diamines, for example according to WO 2008/006449, and dibenzoindenofluoreneamines or -diamines, for example according to WO 2007/140847, and the indenofluorene derivatives having fused aryl groups disclosed in WO 2010/012328. Likewise preferred are the pyrenearylamines disclosed in WO 2012/048780 and in WO 2013/185871. Likewise preferred are the benzoindenofluoreneamines disclosed in WO 2014/037077, the benzofluoreneamines disclosed in WO 2014/106522, the extended benzoindenofluorenes disclosed in WO 2014/111269 and in WO 2017/036574, the phenoxazines disclosed in WO 2017/028940 and WO 2017/028941, and the fluorene derivatives bonded to furan units or to thiophene units that are disclosed in WO 2016/150544.

Useful matrix materials, preferably for fluorescent emitting compounds, include materials of various substance classes. Preferred matrix materials are selected from the classes of the oligoarylenes (e.g. 2,2',7,7'-tetraphenylspirobifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulfoxides, etc. (for example according to WO 2005/084081 and WO 2005/084082), the atropisomers (for example according to WO 2006/048268), the boronic acid derivatives (for example according to WO 2006/117052) or the benzanthracenes (for example according to WO 2008/145239). Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another. Preference is further given to the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154, the pyrene compounds disclosed in EP 1749809, EP 1905754 and US 2012/0187826, the benzanthracenylanthracene compounds disclosed in WO 2015/158409, the indenobenzofurans disclosed in WO 2017/025165, and the phenanthrylanthracenes disclosed in WO 2017/036573.

Preferred matrix materials for phosphorescent emitting compounds are, as well as the compounds of the formula (I), aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109, WO 2011/000455 or WO 2013/041176, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, or lactams, for example according to WO 2011/116865 or WO 2011/137951.

Suitable charge transport materials as usable in the hole injection or hole transport layer or electron blocker layer or in the electron transport layer of the electronic device of the invention are, as well as the compounds of the formula (I), for example, the compounds disclosed in Y. Shirota et al., Chem. Rev. 2007, 107(4), 953-1010, or other materials as used in these layers according to the prior art.

Compounds which are preferably used in hole-transporting layers of the OLEDs of the invention are especially indenofluoreneamine derivatives (for example according to WO 06/122630 or WO 06/100896), the amine derivatives disclosed in EP 1661888, hexaazatriphenylene derivatives (for example according to WO 01/049806), amine derivatives with fused aromatics (for example according to U.S. Pat. No. 5,061,569), the amine derivatives disclosed in WO 95/09147, monobenzoindenofluoreneamines (for example according to WO 08/006449), dibenzoindenofluoreneamines (for example according to WO 07/140847), spirobifluoreneamines (for example according to WO 2012/034627 or WO 2013/120577), fluoreneamines (for example according to WO 2014/015937, WO 2014/015938, WO 2014/015935 and WO 2015/082056), spirodibenzopyranamines (for example according to WO 2013/083216), dihydroacridine derivatives (for example according to WO 2012/150001), spirodibenzofurans and spirodibenzothiophenes, for example according to WO 2015/022051, WO 2016/102048 and WO 2016/131521, phenanthrenediarylamines, for example according to WO 2015/131976, spirotribenzotropolones, for example according to WO 2016/087017, spirobifluorenes with meta-phenyldiamine groups, for example according to WO 2016/078738, spirobisacridines, for example according to WO 2015/158411, xanthenediarylamines, for example according to WO 2014/072017, and 9,10-dihydroanthracene spiro compounds with diarylamino groups according to WO 2015/086108.

Materials used for the electron transport layer may, as well as the compounds of the invention, be any materials as used according to the prior art as electron transport materials in the electron transport layer. Especially suitable are aluminum complexes, for example Alq$_3$, zirconium complexes, for example Zrq$_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Further suitable materials are derivatives of the abovementioned compounds as disclosed in JP 2000/053957, WO 2003/060956, WO 2004/028217, WO 2004/080975 and WO 2010/072300.

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (organic solar cell) or the emission of light (OLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The device is structured appropriately (according to the application), contact-connected and finally sealed, in order to rule out damaging effects of water and air.

In a preferred embodiment, the electronic device is characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

Preference is likewise given to an electronic device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example M. S. Arnold et al., Appl. Phys. Lett. 2008, 92, 053301).

Preference is additionally given to an electronic device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds of formula (I) are needed. High solubility can be achieved by suitable substitution of the compounds.

It is further preferable that an electronic device of the invention is produced by applying one or more layers from solution and one or more layers by a sublimation method.

According to the invention, the electronic devices comprising one or more compounds of formula (I) can be used in displays, as light sources in lighting applications and as light sources in medical and/or cosmetic applications (e.g. light therapy).

WORKING EXAMPLES

A) Synthesis Examples

Stage a) 7-bromo[1,4]benzothiazino[2,3,4-kl]phenothiazine

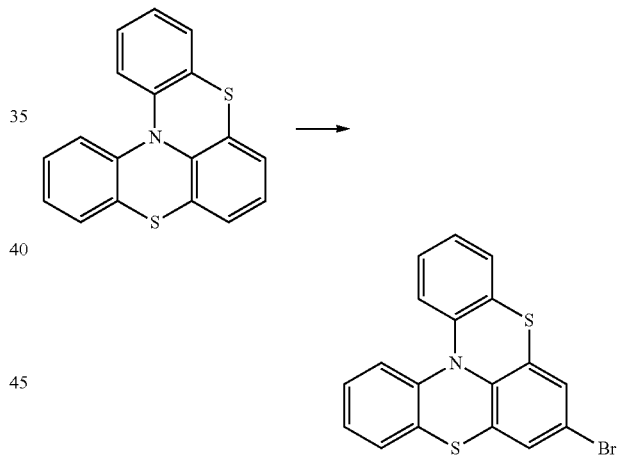

To a solution of [1,4]benzothiazino[2,3,4-kl]phenothiazine (CAS 1050521-47, 48.5 g, 154 mmol) in chloroform (1000 ml) is added N-bromosuccinimide (24.7 g, 139 mmol) in portions at 0° C. with exclusion of light, and the mixture is stirred at this temperature for 2 h. The reaction is ended by addition of sodium sulfite solution and the mixture is stirred at room temperature for a further 30 min. After phase separation, the organic phase is washed with water and the aqueous phase is extracted with dichloromethane. The combined organic phases are dried over sodium sulfate and concentrated under reduced pressure. The residue is dissolved in ethyl acetate and filtered through silica gel. Subsequently, the crude product is recrystallized from heptane.

Yield: 42 g (110 mmol), 64% of theory, colorless solid.

In an analogous manner, it is possible to obtain the following compounds:

| No. | Reactant | Product | Yield |
|---|---|---|---|
| 2a | [784189-24-8] | | 82% |
| 3a | [781643-18-3] | | 65% |
| 4a | [252020-71-6] | | 71% |

In an analogous manner, two eq. of NBS can be used to obtain the following compounds:

| No. | Reactant | Product | Yield |
|---|---|---|---|
| 5a | [784189-24-8] | | 56% |
| 6a | [781643-18-3] | | 58% |

| No. | Reactant | Product | Yield |
|---|---|---|---|
| 7a | ![structure] [252020-71-6] | ![structure with 2 Br] | 51% |

Stage b) dithia-13b-azanaphtho[3,2,1-de]anthracene-7-boronic acid

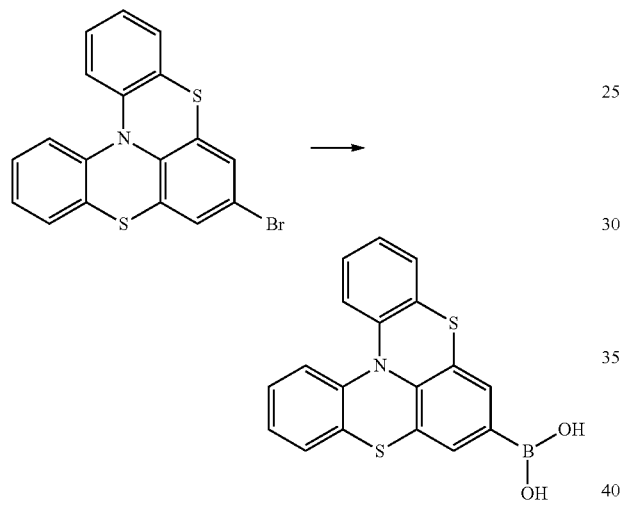

28 g (73 mmol) of 7-bromo-[1,4]benzothiazino[2,3,4-kl]phenothiazine are dissolved in 150 ml of dry THF and cooled to −78° C. At this temperature, 30 ml (76 mmol/2.5 M in hexane) of n-butyllithium are added within about 5 min and then the mixture is stirred at −78° C. for a further 2.5 h. At this temperature, 15 g (145 mmol) of trimethyl borate are added very rapidly and the reaction is allowed to come gradually to room temperature (about 18 h). The reaction solution is washed with water and the precipitated solids and the organic phase are subjected to azeotropic drying with toluene. The crude product is extracted while stirring from toluene/methylene chloride at about 40° C. and filtered off with suction. Yield: 22 g (63 mmol), 90% of theory.

The following compounds are prepared in an analogous manner:

| No. | Reactant | Product | Yield |
|---|---|---|---|
| 2b | ![structure with Br] | ![structure with B(OH)2] | 69% |
| 3b | ![structure with Br] [1416903-68-8] | ![structure with B(OH)2] | 71% |

| No. | Reactant | Product | Yield |
|---|---|---|---|
| 4b | | | 72% |
| 5b | | | 68% |
| 6b | | | 66% |
| 7b | | | 68% |

| No. | Reactant | Product | Yield |
|---|---|---|---|
| 8b | | | 71% |
| 9b | [1380076-62-9] | | 80% |

Stage c): 3,7-Bis(dibenzofuran-1-yl)-5,9-dioxa-13b-azanaphtho[3,2,1de]anthracene

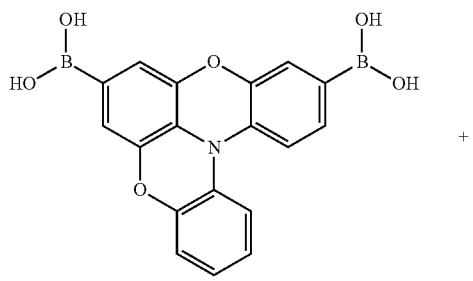

+

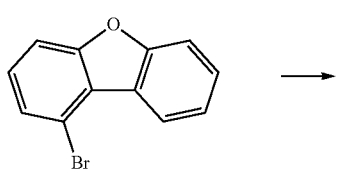

[50548-45-3]

→

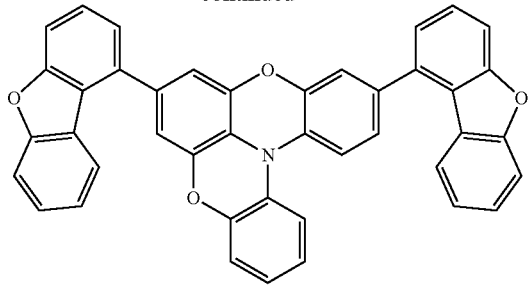

To a degassed mixture of 116 g (470 mmol) of 1-bromodibenzofuran, 169 g (470.0 mmol) of 5,9-dioxa-13b-azanaphtho[3,2,1-de]anthracene-3,7-bisboronic acid, 149.02 g (702.0 mmol) of $K_3PO_4$, 1000 ml of dioxane and 1000 ml of water are added 13.52 g (11.7 mmol) of Pd(PPh$_3$)$_4$. After heating the mixture to 80° C. for 7 h, 4.58 g (93.6 mmol) of NaCN are added. After cooling to room temperature, the aqueous phase is removed. The organic phase is washed twice with $H_2O$ and then dried over $Na_2SO_4$. After the solvent has been removed and the dark red solid has been recrystallized twice from dioxane, the product was obtained in the form of red needles.

Yield: 184 g (304 mmol), 66% of theory; purity: 97% by HPLC.

The following compounds can be prepared in an analogous manner:

| No. | Reactant 1 | Reactant 2 | Product | Yield |
|---|---|---|---|---|
| 1c | B(OH)₂ structure | 942615-32-9 | | 80% |
| 2c | B(OH)₂ structure | 955959-84-9 | | 74% |

Stage d) 3-bromo-7,11-bis(dibenzofuran-1-yl)-5,9-dioxa-13b-azanaphtho[3,2,1-de]anthracene

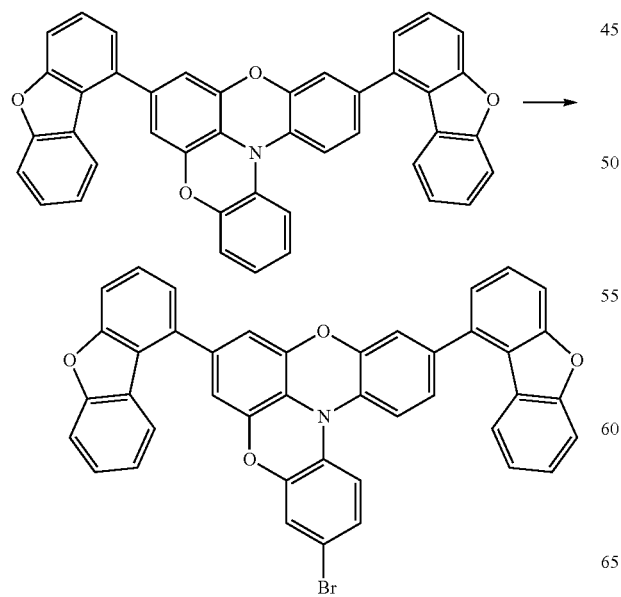

45.1 g (74.6 mmol) of 3,7-bis(dibenzofuran-1-yl)-5,9-dioxa-13b-azanaphtho[3,2,1de] anthracene are initially charged in 80 ml of DMF. Subsequently, 13.3 g (74.6 mmol) of NBS are added in portions and stirring is continued at this temperature for 4 h. Subsequently, 15 ml of water are added to the mixture and extraction is effected with CH₂Cl₂. The organic phase is dried over MgSO₄ and the solvents are removed under reduced pressure. The product is subjected to extractive stirring with hot hexane and filtered off with suction. Yield: 39 g (58 mmol), 78% of theory, purity by ¹H NMR about 96%.

The following compounds can be prepared in an analogous manner:

| No. | Reactant 1 | Product | Yield |
|---|---|---|---|
| 1d | | | 80% |
| 2d | | | 74% |
Stage e) 7-[9-(4,6-diphenyl-[1,3,5]triazin-2-yl)-9H-carbazol-3-yl]-5,9-dithia-13b-azanaphtho[3,2,1-de]anthracene
-continued
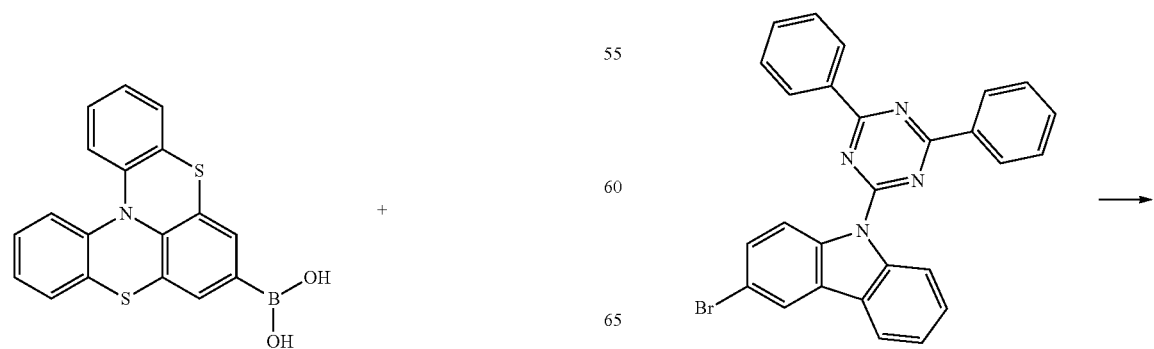

-continued

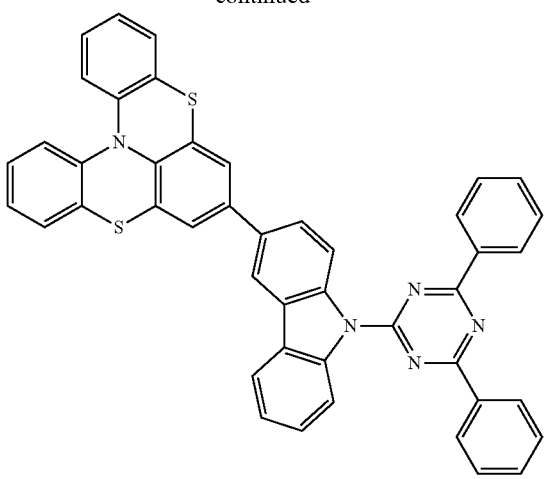

11 g (32 mmol) of dithia-13b-azanaphtho[3,2,1-de]anthracene-7-boronic acid, 14 g (31.6 mmol) of 3-bromo-9-(4,6-diphenyl-[1,3,5]triazin-2-yl)-9H-carbazole, and 31 ml (63 mmol) of $Na_2CO_3$ (2 M solution) are suspended in 120 ml of toluene, 120 ml of ethanol. 0.73 g (0.63 mmol) of $Pd(PPh_3)_4$ is added to this suspension, and the reaction mixture is heated under reflux for 16 h. After cooling, the organic phase is removed, filtered through silica gel, washed three times with 200 ml of water and then concentrated to dryness. The residue is recrystallized from toluene and purified by sublimation twice under reduced pressure (p=5× $10^{-5}$ mbar, T=329° C.). The yield is 16.7 g (24 mmol), corresponding to 76% of theory.

In an analogous manner, the following compounds are obtained:

| Ex. | Reactant 1 | Reactant 2 | Product | Yield |
|---|---|---|---|---|
| 1e | 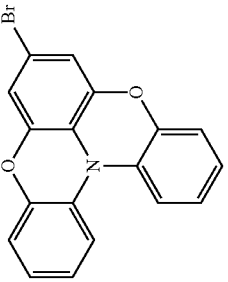 | 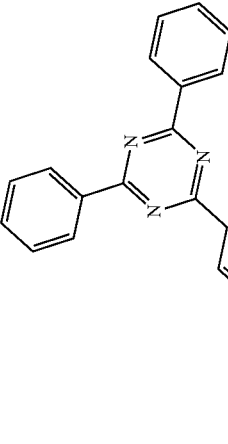 | 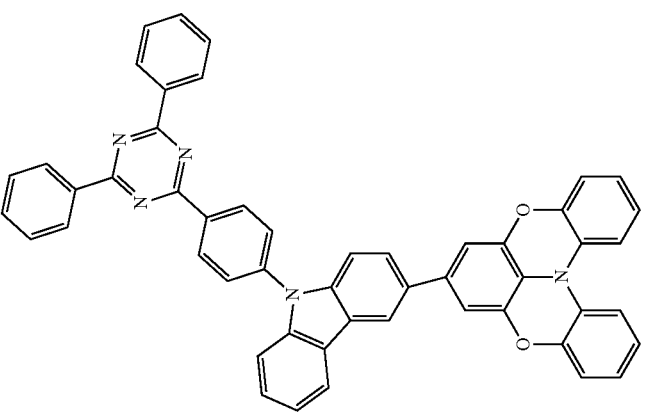 | 64% |

-continued

| Ex. | Reactant 1 | Reactant 2 | Product | Yield |
|---|---|---|---|---|
| 2e | (structure with Br, O, N, O) | (structure with triazine, phenyls, carbazole-naphthalene, Bpin) [1658982-98-5] | (coupled product) | 63% |

-continued

| Ex. | Reactant 1 | Reactant 2 | Product | Yield |
|---|---|---|---|---|
| 3e | [1416903-68-8] | [1656982-97-8] | | 73% |

| Ex. | Reactant 1 | Reactant 2 | Product | Yield |
|---|---|---|---|---|
| 4e | | [1656982-71-6] | | 79% |
| 5e | | [1642121-60-5] | | 70% |

-continued

| Ex. | Reactant 1 | Reactant 2 | Product | Yield |
|---|---|---|---|---|
| 6e | | [1628068-19-2] | | 74% |
| 7e | | [1628066-21-8] | | 71% |

-continued

| Ex. | Reactant 1 | Reactant 2 | Product | Yield |
|---|---|---|---|---|
| 8e | | [1346010-98-7] | | 65% |
| 9e | | [1628068-27-2] | | 87% |

-continued
| Ex. | Reactant 1 | Reactant 2 | Product | Yield |
|---|---|---|---|---|
| 10e | 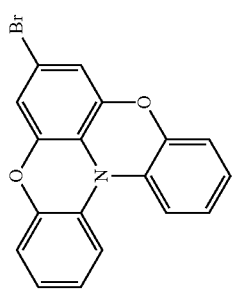 | 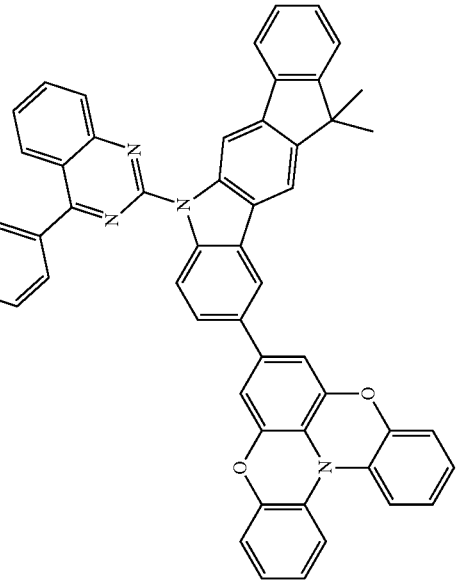 [1377576-61-8] | 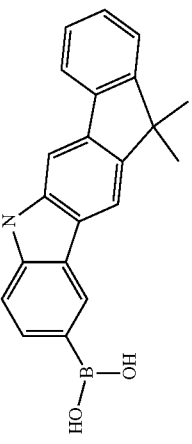 | 73% |

| Ex. | Reactant 1 | Reactant 2 | Product | Yield |
|---|---|---|---|---|
| 11e | | [1314019-71-0] | | 72% |
| 12e | | [1622875-81-3] | | 70% |

| Ex. | Reactant 1 | Reactant 2 | Product | Yield |
|---|---|---|---|---|
| 13e | 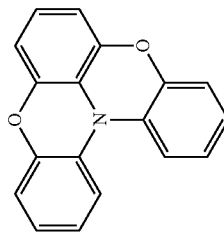 [1416903-68-8] | 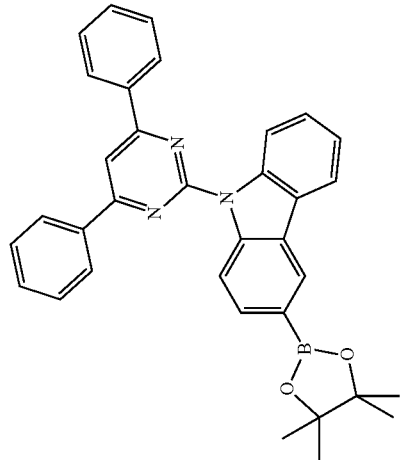 [1380100-30-0] | 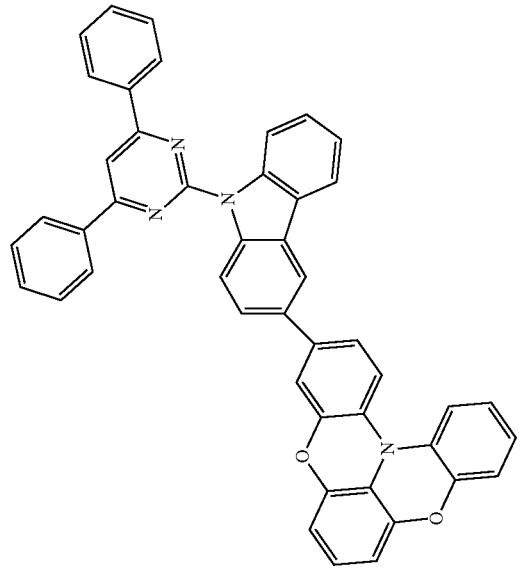 | 77% |
| 14e | 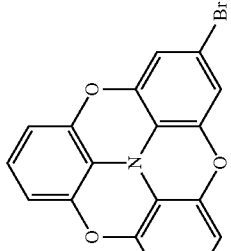 | 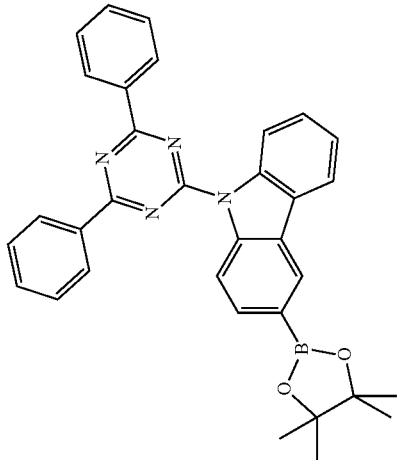 [1361094-91-8] | 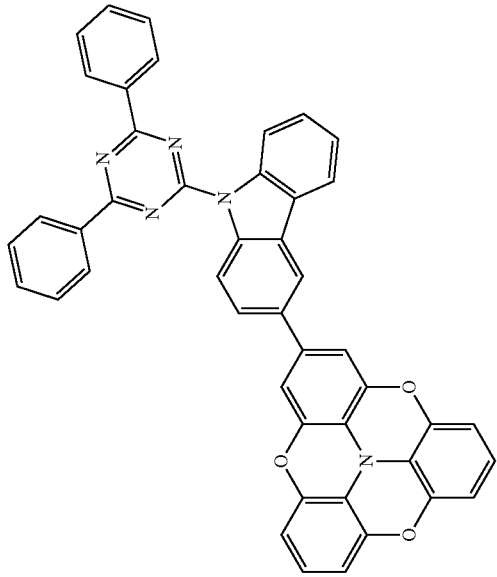 | 76% |

-continued

| Ex. | Reactant 1 | Reactant 2 | Product | Yield |
|---|---|---|---|---|
| 15e | (structure with Br) | (structure) [1702361-59-8] | (structure) | 70% |

| Ex. | Reactant 1 | Reactant 2 | Product | Yield |
|---|---|---|---|---|
| 16e | (structure) | (structure) [1423809-54-4] | (structure) | 69% |
| 17e | (structure) | (structure) [1702359-59-8] | (structure) | 80% |

-continued
| Ex. | Reactant 1 | Reactant 2 | Product | Yield |
|---|---|---|---|---|
| 18e | 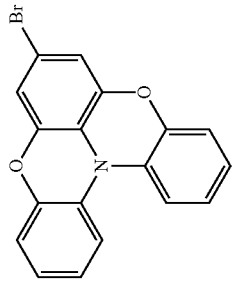 | 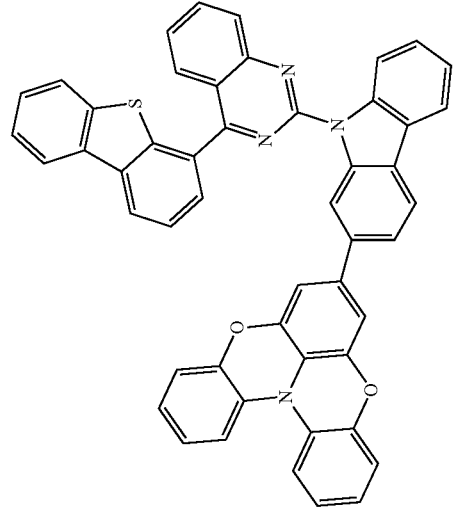 | | 72% |
| 19e | 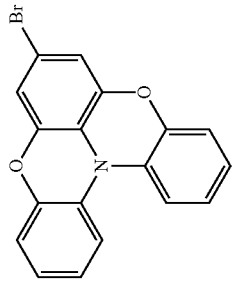 | 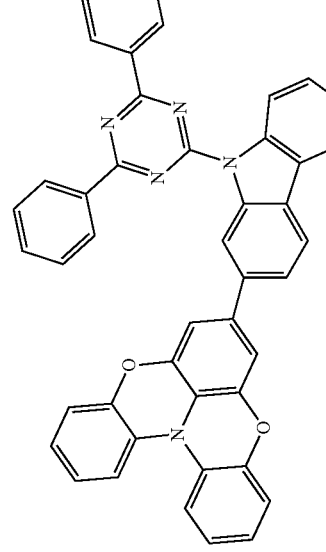 | | 73% |

-continued

| Ex. | Reactant 1 | Reactant 2 | Product | Yield |
|---|---|---|---|---|
| 20e | | [1642121-58-1] | | 77% |
| 21e | | [1642121-58-1] | | 71% |

-continued

| Ex. | Reactant 1 | Reactant 2 | Product | Yield |
|---|---|---|---|---|
| 22e | | [1642121-58-1] | | 56% |
| 23e | | [1658982-98-5] | | 72% |

| Ex. | Reactant 1 | Reactant 2 | Product | Yield |
|---|---|---|---|---|
| 24e | (structure) | (structure) [1656982-97-8] | (structure) | 78% |

| Ex. | Reactant 1 | Reactant 2 | Product | Yield |
|---|---|---|---|---|
| 25e | | [1658982-98-5] | | 77% |

| Ex. | Reactant 1 | Reactant 2 | Product | Yield |
|---|---|---|---|---|
| 26e | 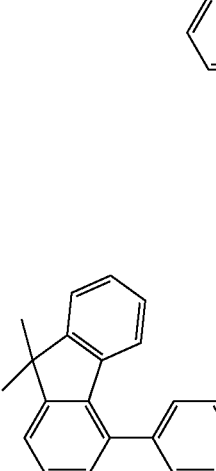 | 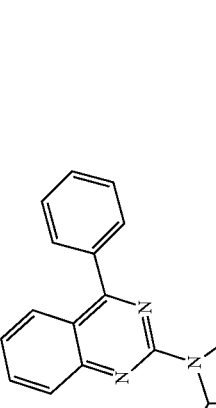 [1642121-58-1] | 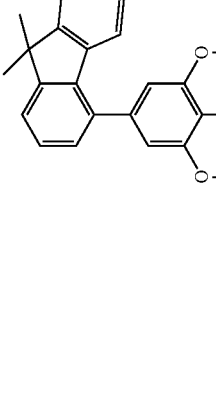 | 70% |

-continued

| Ex. | Reactant 1 | Reactant 2 | Product | Yield |
|---|---|---|---|---|
| 27e | | [1642121-58-1] | | 67% |
| 28e | | [63503-60-6] | | 69% |

| Ex. | Reactant 1 | Reactant 2 | Product | Yield |
|---|---|---|---|---|
| 29e | | [1642121-58-1] | | 72% |

-continued

| Ex. | Reactant 1 | Reactant 2 | Product | Yield |
|---|---|---|---|---|
| 31e | (structure shown) | (structure shown) [1821233-72-0] | (structure shown) | 67% |

| Ex. | Reactant 1 | Reactant 2 | Product | Yield |
|---|---|---|---|---|
| 32e | 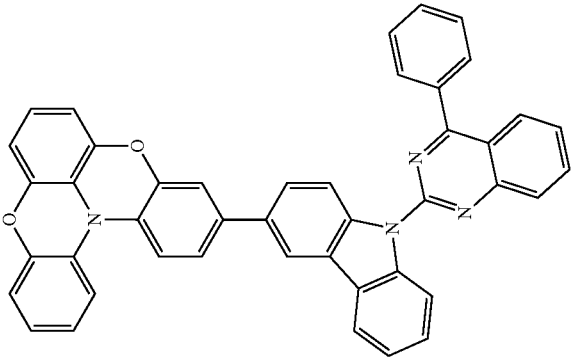 [1416903-68-8] | 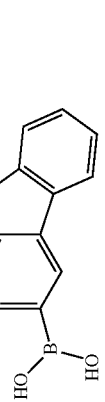 [1642121-58-1] | 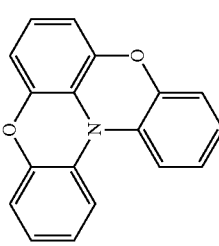 | 77% |

| Ex. | Reactant 1 | Reactant 2 | Product | Yield |
|---|---|---|---|---|
| 33e | | [1642121-58-1] | | 75% |
| 34e | | [1642121-58-1] | | 70% |

-continued

| Ex. | Reactant 1 | Reactant 2 | Product | Yield |
|---|---|---|---|---|
| 35e | | [1813537-15-3] | | 65% |
| 36e | | [1813537-17-5] | | 67% |

-continued
| Ex. | Reactant 1 | Reactant 2 | Product | Yield |
|---|---|---|---|---|
| 37e | 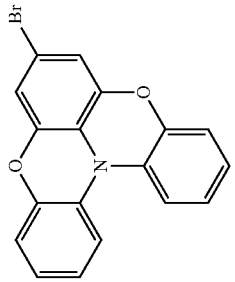 | 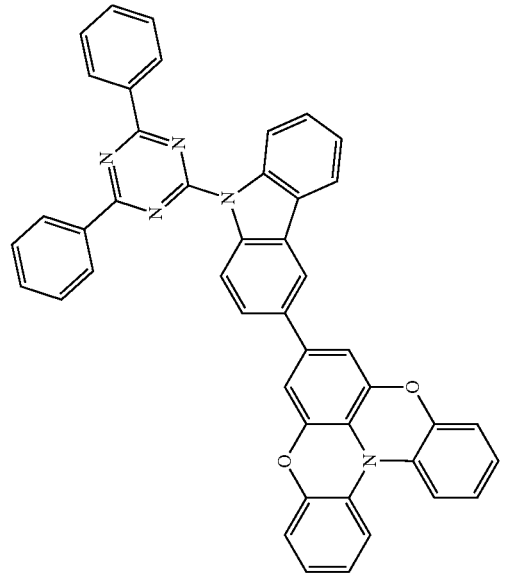 [1361094-91-8] | 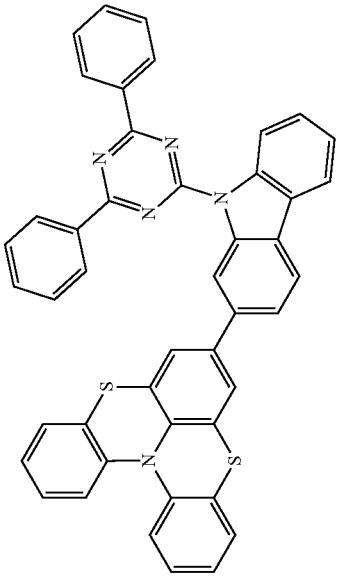 | 77% |
| 38e | 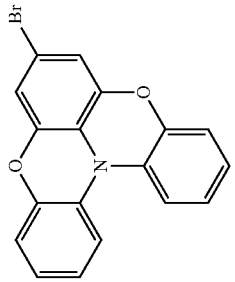 | 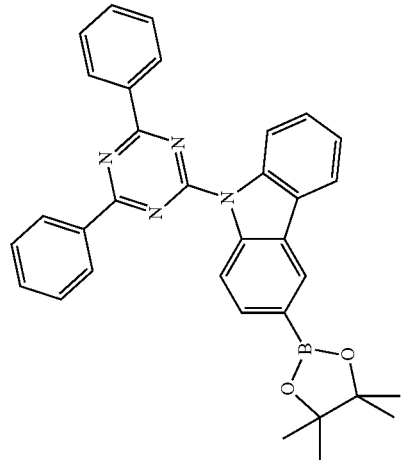 [1642121-55-8] | 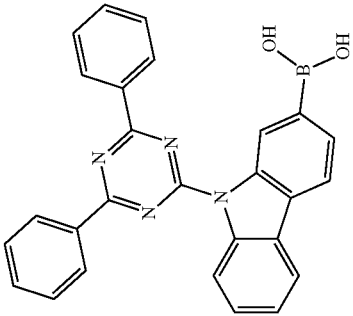 | 69% |

| Ex. | Reactant 1 | Reactant 2 | Product | Yield |
|---|---|---|---|---|
| 39e | 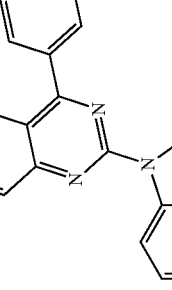 CAS [1415901-44-8] | 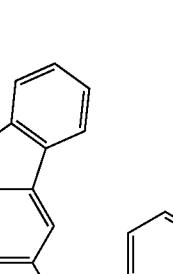 [1642121-58-1] | 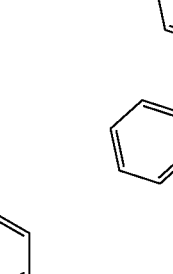 | 62% |
| 40e |  [1380485-64-2] | 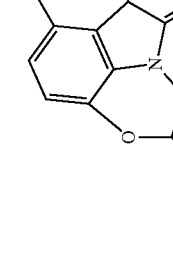 [1476799-10-6] | 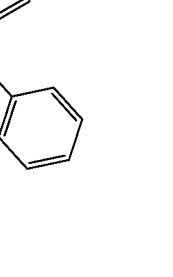 | 61% |

| Ex. | Reactant 1 | Reactant 2 | Product | Yield |
|---|---|---|---|---|
| 41e | [1380485-64-2] | [1266389-17-6] | | 66% |

B) Device Examples

Examples I1 to I12 which follow (see table 1) show the use of the compounds of the invention in OLEDs. Examples C1 to C4 (see table 1) are reference examples.

1) General Description of the Production and Analysis of the OLEDs:

Glass plaques coated with structured ITO (indium tin oxide) of thickness 50 nm are treated prior to coating with an oxygen plasma, followed by an argon plasma. These plasma-treated glass plaques form the substrates to which the OLEDs are applied.

The OLEDs basically have the following layer structure: substrate/hole injection layer (HIL)/hole transport layer (HTL)/electron blocker layer (EBL)/emission layer (EML)/ optional hole blocker layer (HBL)/electron transport layer (ETL) and finally a cathode. The cathode is formed by an aluminum layer of thickness 100 nm. The HIL used is a 5 nm-thick layer of the material HATCN. The HTL used is a 125 nm-thick layer of the material SpMA1. The EBL used is a 10 nm-thick layer of the material SpMA3. The further construction of OLEDs can be inferred from table 1. The materials used for production of the OLEDs are shown in Table 2.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC5:IC3:TEG2 (55%:35%:10%) mean here that the material IC5 is present in the layer in a proportion by volume of 55%, IC3 in a proportion of 35% and TEG2 in a proportion of 10%, based in each case on volume. Analogously, the electron transport layer may also consist of a mixture of two materials.

The OLEDs are characterized in a standard manner. For this purpose, the electroluminescence spectra and the current-voltage-luminance characteristics (IUL characteristics) are measured. The electroluminescence spectra are determined at a luminance of 1000 cd/m$^2$, and the CIE 1931 x and y color coordinates are calculated therefrom.

2) Comparison of the inventive compounds IV1-1V4 with prior art compounds PA1 to PA4

The materials of the invention can be used in the emission layer in phosphorescent red OLEDs. Compared to the prior art (compounds PA1-4 from examples C1-C4 in table 1), with use of the molecules of the invention as matrix material in the emission layer, a reduction in the voltage at a luminance of 1000 cd/m$^2$ by 10% in each case is found (direct comparison of example I1 with C1, I2 with C2, I3 with C3 and I4 with C4). This constitutes a significant improvement in the OLEDs.

3) Use of the compounds of the invention in the emitting layer, in the hole blocker layer and in the electron transport layer of OLEDs.

The inventive compounds IV1 to IV9 and IV13 to IV15 are used in examples I1 to I12 as matrix material in the emission layer in combination with phosphorescent emitters. The color coordinates of the electroluminescence spectra of the OLEDs from these experiments are CIEx=0.67 and CIEy=0.33. The materials are thus suitable for use in the emission layer of red OLEDs.

In addition, the materials of the invention can be used successfully in the electron transport layer (ETL) or the hole blocker layer (HBL). This is shown in experiments I13-I15. Here too, the color coordinates of the spectrum of the OLEDs are CIEx=0.67 and CIEy=0.33.

TABLE 1

| | Structure of the OLEDs | | |
|---|---|---|---|
| Ex. | EML thickness | HBL thickness | ETL thickness |
| C1 | PA1:TER5 (95%:5%) 40 nm | — | ST2:LiQ (50%:50%) 35 nm |
| C2 | PA2:TER5 (95%:5%) 40 nm | — | s.o. |
| C3 | PA3:TER5 (95%:5%) 40 nm | — | s.o. |
| C4 | PA4:TER5 (95%:5%) 40 nm | — | s.o. |
| I1 | IV1:TER5 (95%:5%) 40 nm | — | s.o. |
| I2 | IV2:TER5 (95%:5%) 40 nm | — | s.o. |
| I3 | IV3:TER5 (95%:5%) 40 nm | — | s.o. |
| I4 | IV4:TER5 (95%:5%) 40 nm | — | s.o. |
| I5 | IV5:PA1:TER5 (85%:10%:5%) 40 nm | — | s.o. |
| I6 | IV6:TER5 (95%:5%) 40 nm | — | s.o. |
| I7 | IV7:TER5 (95%:5%) 40 nm | — | s.o. |
| I8 | IV8:TER5 (95%:5%) 40 nm | — | s.o |
| I9 | IV9:TER5 (95%:5%) 40 nm | — | s.o. |
| I10 | IV13:TER5 (95%:5%) 40 nm | — | s.o. |
| I11 | IV14:TER5 (95%:5%) 40 nm | — | s.o. |
| I12 | IV15:TER5 (95%:5%) 40 nm | — | s.o. |
| I13 | IV1:TER5 (95%:5%) 40 nm | — | IV10:LiQ (50%:50%) 35 nm |
| I14 | s.o. | IV11 5 nm | ST2:LiQ (50%:50%) 30 nm |
| I15 | s.o. | SV12 5 nm | s.o. |

TABLE 2
Structural formulae of the materials for the OLEDs
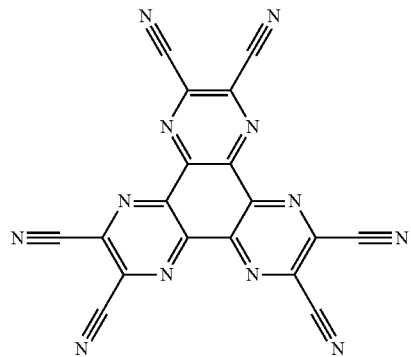 [SMILES: N#Cc1nc2c3nc(C#N)c(C#N)nc3c3nc(C#N)c(C#N)nc3c2nc1C#N]
HATCN
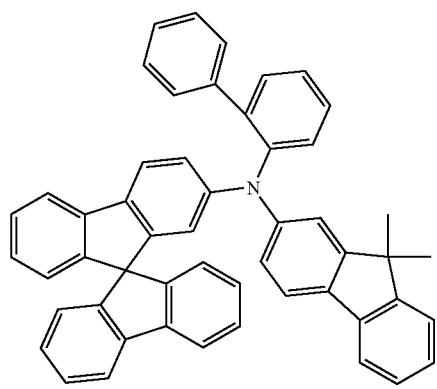 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
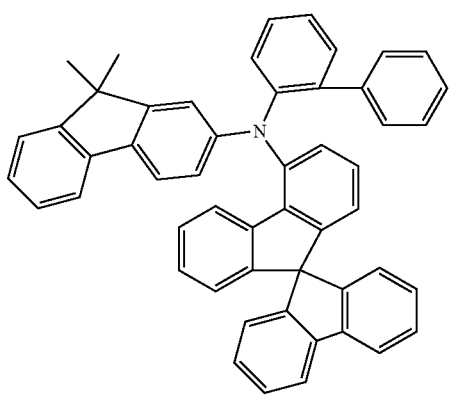 [SMILES: CC1(C)c2ccccc2-c2ccc(N(c3ccccc3-c3ccccc3)c3cccc4c3-c3ccccc3C43c4ccccc4-c4ccccc43)cc21]
SpMA3

TABLE 2-continued
Structural formulae of the materials for the OLEDs
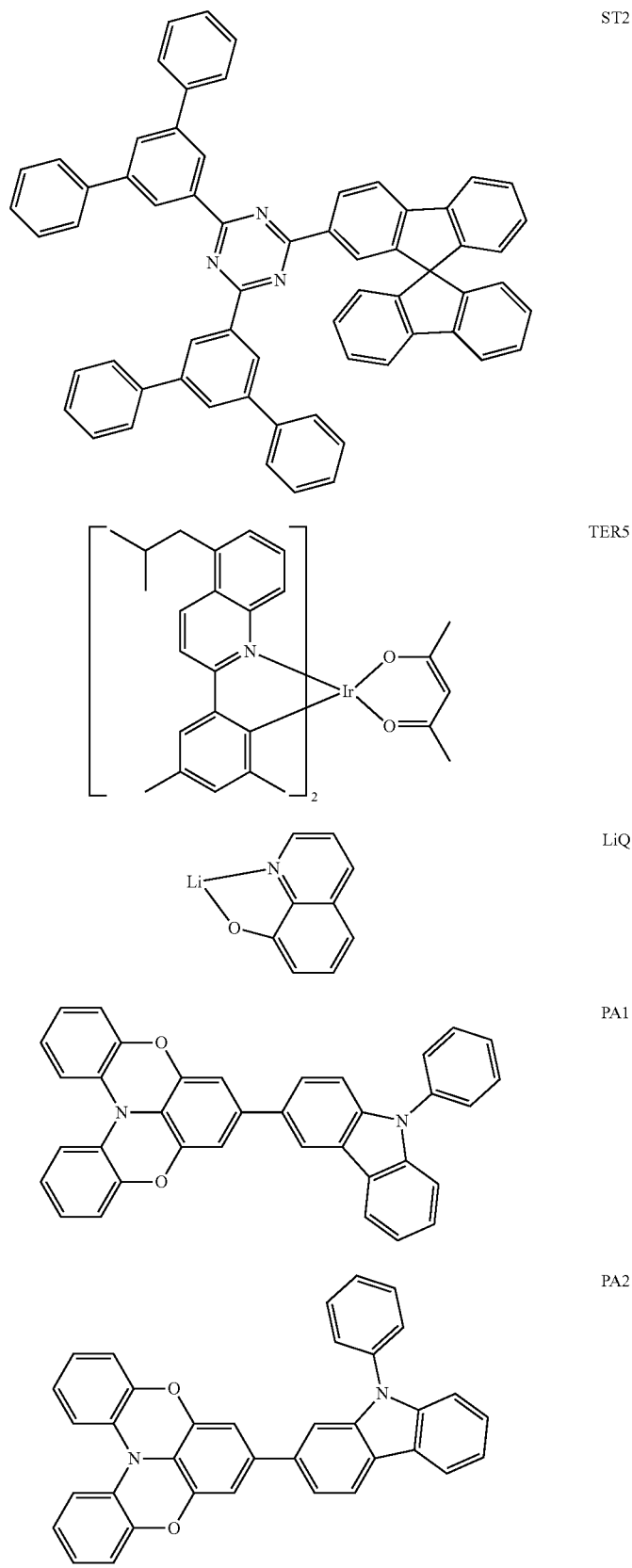
ST2
TER5
LiQ
PA1
PA2

TABLE 2-continued
Structural formulae of the materials for the OLEDs
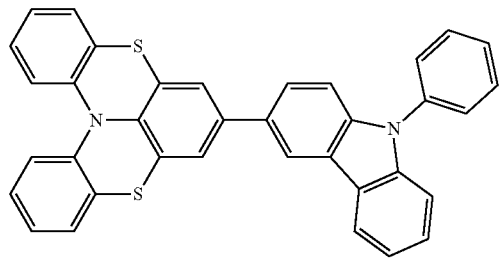 [SMILES: c1ccc(-n2c3ccccc3c3cc(-c4cc5c6c(c4)Oc4ccccc4N6c4ccccc4O5)ccc32)cc1]
PA3
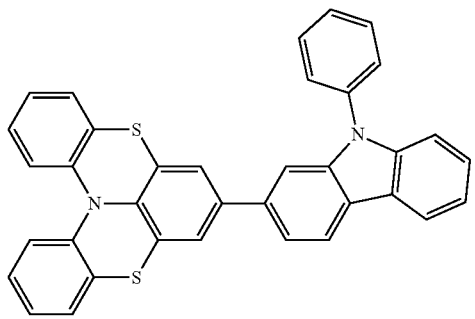 [SMILES: c1ccc(-n2c3ccccc3c3ccc(-c4cc5c6c(c4)Oc4ccccc4N6c4ccccc4O5)cc32)cc1]
PA4
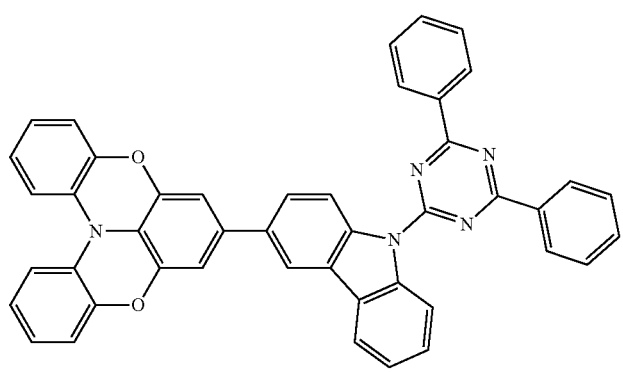
IV1
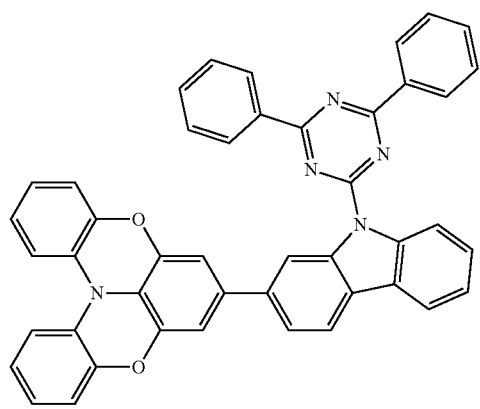 [SMILES: c1ccc(-c2nc(-c3ccccc3)nc(-n3c4ccccc4c4ccc(-c5cc6c7c(c5)Oc5ccccc5N7c5ccccc5O6)cc43)n2)cc1]
IV2

TABLE 2-continued
Structural formulae of the materials for the OLEDs
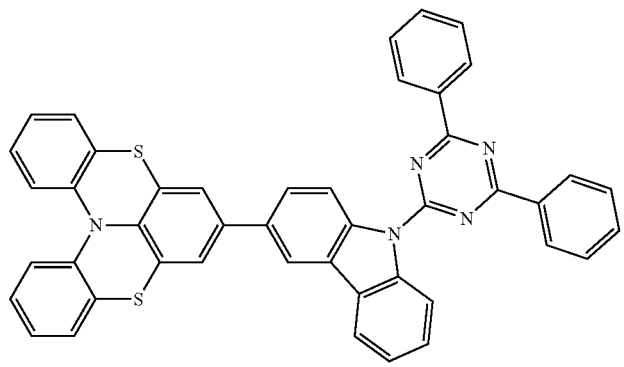 [SMILES: c1ccc(-c2nc(-c3ccccc3)nc(-n3c4ccccc4c4cc(-c5cc6c7c(c5)Sc5ccccc5N7c5ccccc5S6)ccc43)n2)cc1]
IV3
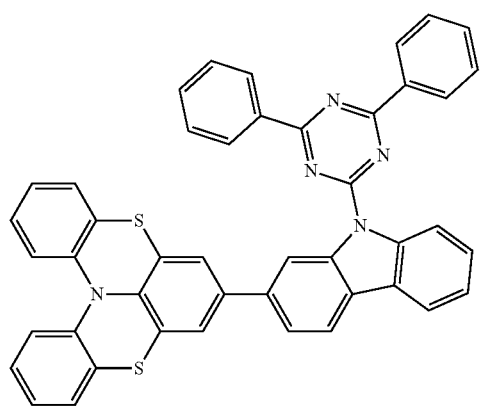
IV4
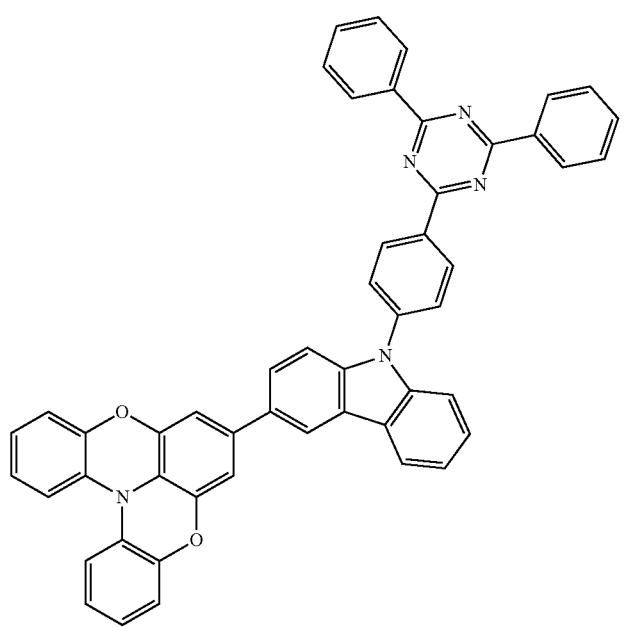
IV5

TABLE 2-continued
Structural formulae of the materials for the OLEDs
IV6
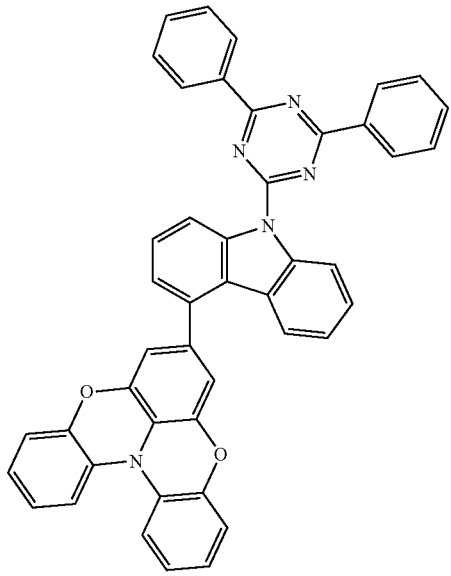 [SMILES: c1ccc(-c2nc(-c3ccccc3)nc(-n3c4ccccc4c4c(-c5cc6c7c(c5)Oc5ccccc5N7c5ccccc5O6)cccc43)n2)cc1]
IV7
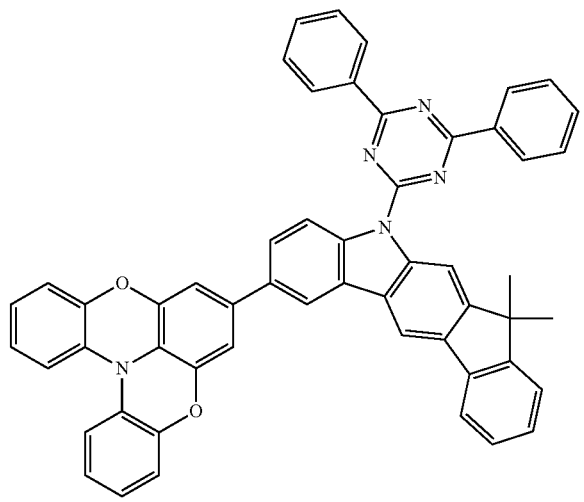
IV8
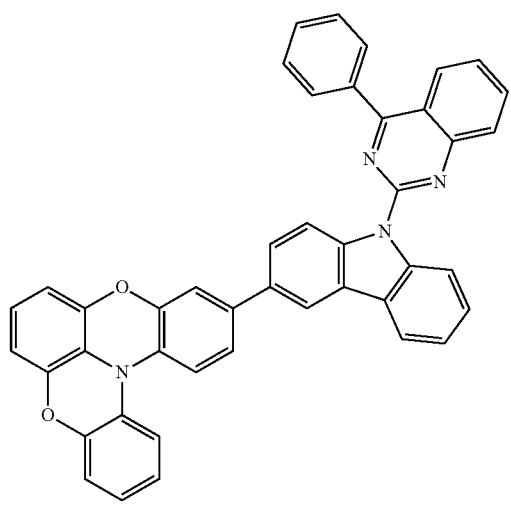

TABLE 2-continued
Structural formulae of the materials for the OLEDs
IV9
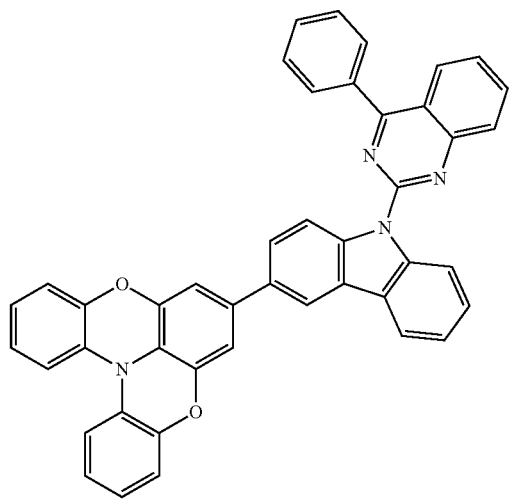
IV10
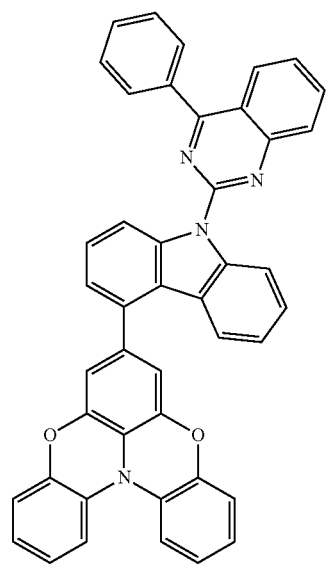 [SMILES: c1ccc(-c2nc(-n3c4ccccc4c4c(-c5cc6c7c(c5)Oc5ccccc5N7c5ccccc5O6)cccc43)nc3ccccc23)cc1]
IV11
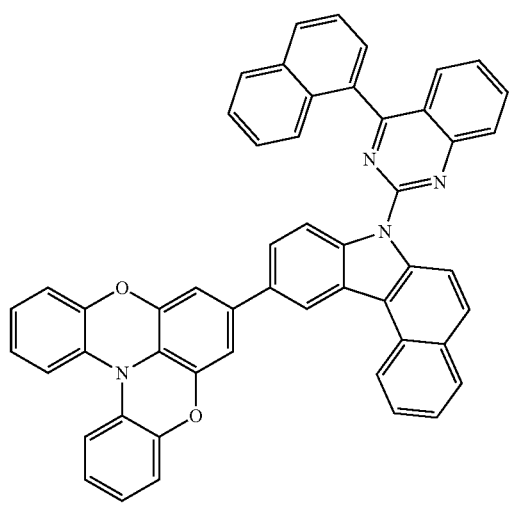

TABLE 2-continued
Structural formulae of the materials for the OLEDs
IV12
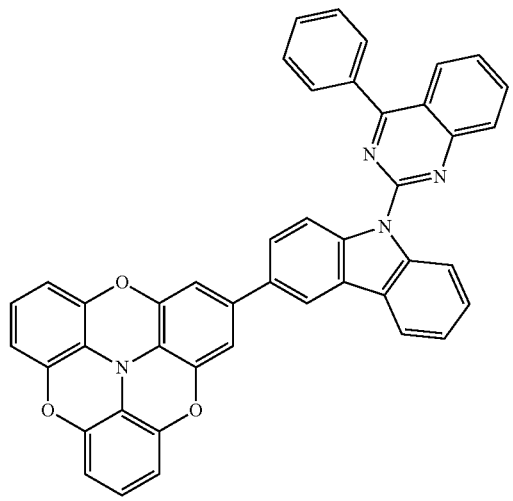
IV13
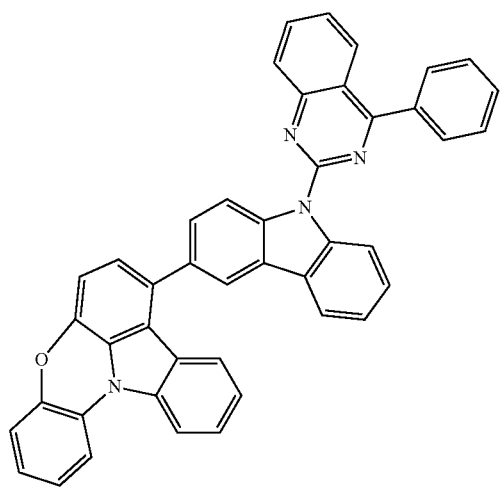 [SMILES: c1ccc(-c2nc(-n3c4ccccc4c4cc(-c5ccc6c7c5c5ccccc5n7-c5ccccc5O6)ccc43)nc3ccccc23)cc1]
IV14
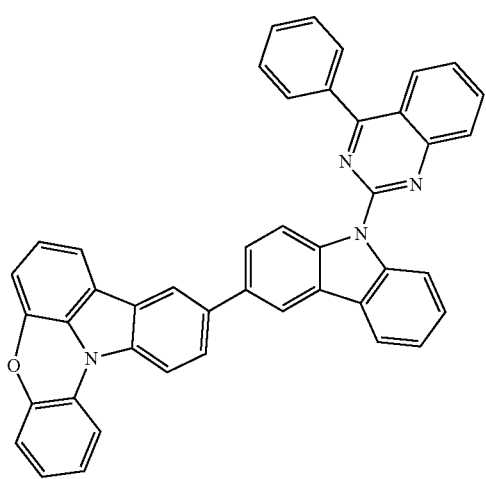 [SMILES: c1ccc(-c2nc(-n3c4ccccc4c4cc(-c5ccc6c(c5)c5cccc7c5n6-c5ccccc5O7)ccc43)nc3ccccc23)cc1]

TABLE 2-continued

Structural formulae of the materials for the OLEDs

IV15

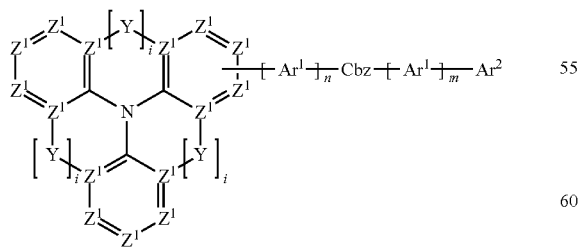

B) Device Examples

Examples I1 to I12 which follow (see table 1) show the use of the compounds of the invention in OLEDs. Examples C1 to C4 (see table 1) are reference examples.

1) General Description of the Production and Analysis of the OLEDs:

Glass plaques coated with structured ITO (indium tin oxide) of thickness 50 nm are treated prior to coating with an oxygen plasma, followed by an argon plasma. These plasma-treated glass plaques form the substrates to which the OLEDs are applied.

The OLEDs basically have the following layer structure: substrate/hole injection layer (HIL)/hole transport layer (HTL)/electron blocker layer (EBL)/emission layer (EML)/optional hole blocker layer (HBL)/electron transport layer (ETL) and finally a cathode. The cathode is formed by an aluminum layer of thickness 100 nm. The HIL used is a 5 nm-thick layer of the material HATCN. The HTL used is a 125 nm-thick layer of the material SpMA1. The EBL used is a 10 nm-thick layer of the material SpMA3. The

The invention claimed is:

1. A compound of formula (I)

Formula (I)

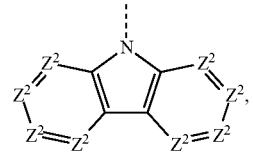

where the variables that occur are as follows:

Y is the same or different at each instance and is selected from a single bond, O and S, where there is at least one Y group selected from O and S;

$Z^1$ is the same or different at each instance and is $CR^1$, N or C, where a $Z^1$ group is C in the specific case when a Y group is bonded to it;

$Ar^1$ is the same or different at each instance and is an aromatic ring system which has 6 to 24 aromatic ring atoms and may be substituted by one or more $R^2$ radicals;

Cbz is a divalent group of the formula (Cbz)

Formula (Cbz)

substituted at each of its unoccupied positions by an $R^3$ radical, where one of the two bonds of the divalent group to the rest of the compound is the dotted bond on the nitrogen atom of the formula (Cbz), where the second of these two bonds may be at any unoccupied position in the group, and where $Z^2$ is the same or different at each instance and is selected from C and N;

$Ar^2$ is selected from the formulae (Ar²-A)

(Ar²-B)

-continued

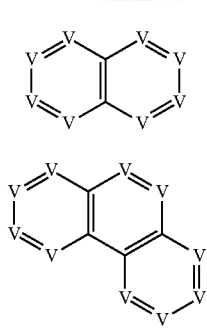
(Ar²-D)

(Ar²-E)

where the variables that occur are defined as follows:

V is the same or different at each instance and is N or CR⁴, where at least one V group in each of formulae (Ar²-A), (Ar²-D) and (Ar²-E) is N;

W is the same or different at each instance and is N or CR⁴;

U is NR⁴;

where at least one group selected from W and V groups in formula (Ar²—B) is N; and where one R⁴ group per formula is replaced by the bond to the Ar¹ group or Cbz;

R¹, R², R⁴ are the same or different at each instance and are selected from H, D, F, C(=O)R⁵, CN, Si(R⁵)₃, N(R⁵)₂, P(=O)(R⁵)₂, OR⁵, S(=O)R⁵, S(=O)₂R⁵, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R¹ or R² or R³ or R⁴ radicals may be joined to one another and may form a ring; where the alkyl, alkoxy, alkenyl and alkynyl groups mentioned and the aromatic ring systems and heteroaromatic ring systems mentioned may each be substituted by one or more R⁵ radicals; and where one or more CH₂ groups in the alkyl, alkoxy, alkenyl and alkynyl groups mentioned may be replaced by —R⁵C=CR⁵—, —C≡C—, Si(R⁵)₂, C=O, C=NR⁵, —C(=O)O—, —C(=O)NR⁵—, NR⁵, P(=O)(R⁵), —O—, —S—, SO, SO₂;

R³ are the same or different at each instance and are selected from H, D, F, C(=O)R⁵, CN, Si(R⁵)₃, N(R⁵)₂, P(=O)(R⁵)₂, OR⁵, S(=O)R⁵, S(=O)₂R⁵, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, and aromatic ring systems having 6 to 40 aromatic ring atoms; where two or more or R³ or R⁴ radicals may be joined to one another and may form a ring; where the alkyl, alkoxy, alkenyl and alkynyl groups mentioned and the aromatic ring systems; and where one or more CH₂ groups in the alkyl, alkoxy, alkenyl and alkynyl groups mentioned may be replaced by —R⁵C=CR⁵—, —C≡C—, Si(R⁵)₂, C=O, C=NR⁵, —C(=O)O—, —C(=O)NR⁵—, NR, P(=O)(R⁵), —O—, —S—, SO, SO₂;

R⁵ is the same or different at each instance and is selected from H, D, F, C(=O)R⁶, CN, Si(R⁶)₃, N(R⁶)₂, P(=O)(R⁶)₂, S(=OR⁶, S(=O)R⁶, S(=O)₂R⁶, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R⁵ radicals may be joined to one another and may form a ring; where the alkyl, alkoxy, alkenyl and alkynyl groups mentioned and the aromatic ring systems and heteroaromatic ring systems mentioned may each be substituted by one or more R⁶ radicals; and where one or more CH₂ groups in the alkyl, alkoxy, alkenyl and alkynyl groups mentioned may be replaced by —R⁶C=CR⁶—, —C≡C—, Si(R⁶)₂, C=O, C=NR⁶, —C(=O)O—, —C(=O)NR⁶—, NR⁶, P(=O)(R⁶), —O—, —S—, SO, or SO₂;

R⁶ is the same or different at each instance and is selected from H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more R⁶ radicals may be joined to one another and may form a ring; and where the alkyl, alkoxy, alkenyl and alkynyl groups, aromatic ring systems and heteroaromatic ring systems mentioned may be substituted by F or CN;

i is the same or different at each instance and is 0 or 1, where at least two indices i in formula (I) are 1, and where the Y group in question is absent when the corresponding index i=0;

n is 0, 1, 2, 3 or 4; and m is 0, 1, 2, 3 or 4.

2. The compound as claimed in claim 1, wherein the Cbz group is the same or different at each instance and is selected from carbazole, azacarbazole, benzocarbazole, dibenzocarbazole, indenocarbazole, indolocarbazole, carbazole fused to benzofuran and carbazole fused to benzothiophene, where the groups mentioned may each be substituted by one or more R³ radicals.

3. The compound as claimed in claim 1, wherein the Cbz group is selected from the formulae

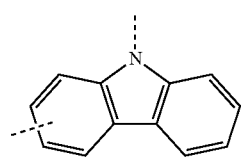
Formula (Cbz-1)

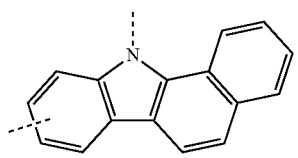
(Formula (Cbz-2)

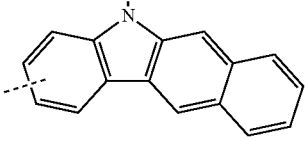
Formula (Cbz-3)

Formula (Cbz-4)
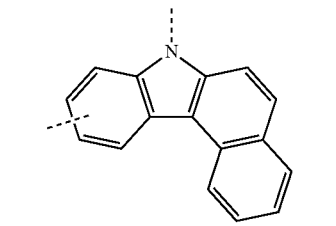
(Formula Cbz-5)
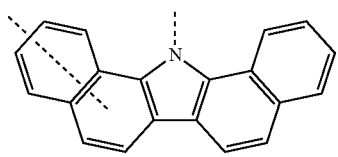
Formula (Cbz-6)
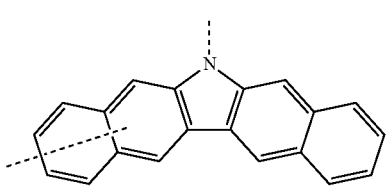
Formula (Cbz-7)
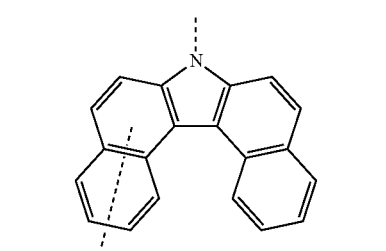
Formula (Cbz-8)
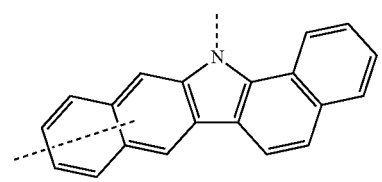
Formula (Cbz-9)
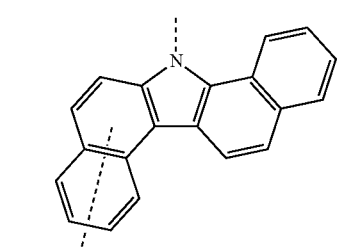
Formula (Cbz-10)
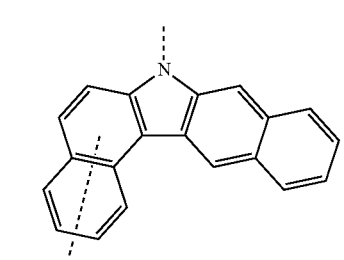
Formula (Cbz-11)
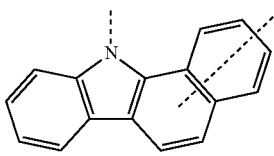
Formula (Cbz-12)
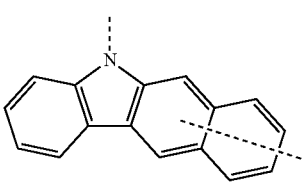
Formula (Cbz-13)
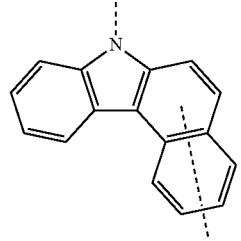
Formula (Cbz-14)
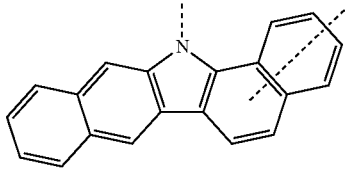
Formula (Cbz-15)
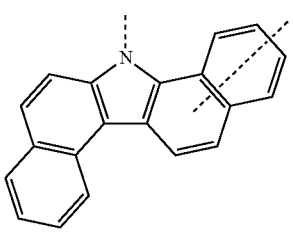
Formula (Cbz-16)
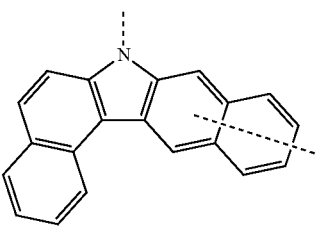
Formula (Cbz-17)
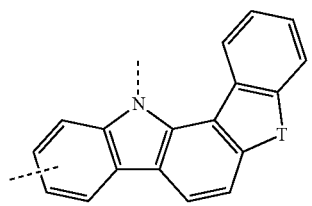

Formula (Cbz-18)

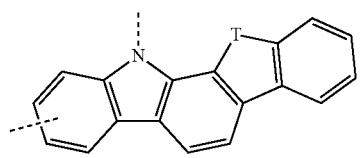

Formula (Cbz-19)

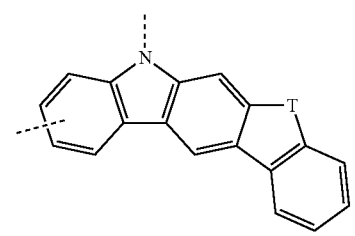

Formula (Cbz-20)

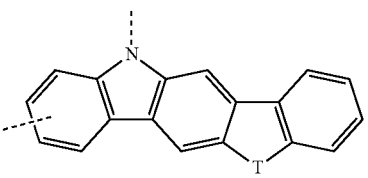

Formula (Cbz-21)

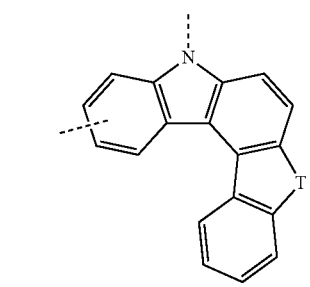

Formula (Cbz-22)

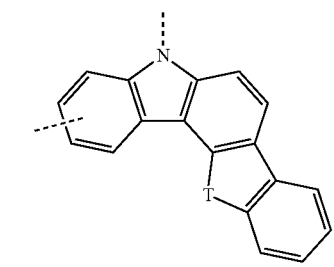

Formula (Cbz-23)

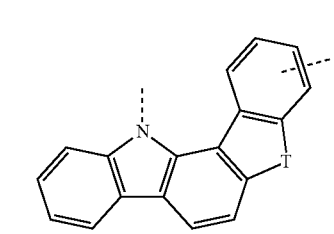

Formula (Cbz-24)

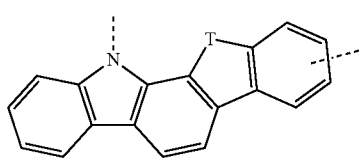

Formula (Cbz-25)

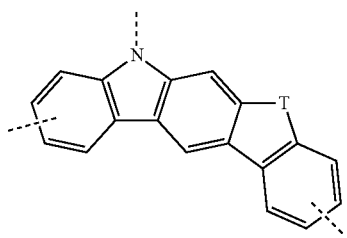

Formula (Cbz-26)

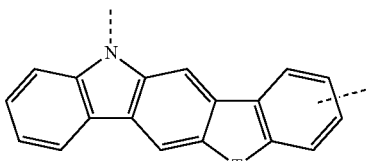

Formula (Cbz-27)

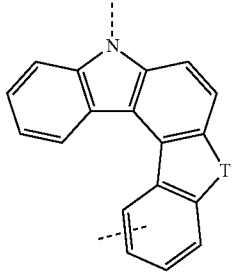

Formula (Cbz-28)

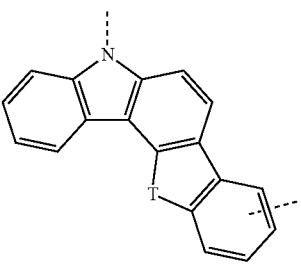

Formula (Cbz-29)

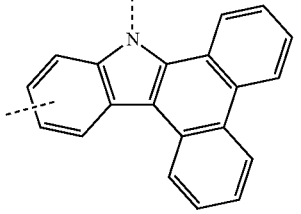

where:
T is $C(R^3)_2$, O, S or $NR^3$;
where the dotted bonds represent the bonds to the rest of the compound, and
where the groups in the abovementioned formulae may each be substituted by an $R^3$ radical at any position shown as unsubstituted.

4. The compound as claimed in claim 1, wherein Y is the same or different at each instance and is selected from O and S.

5. The compound as claimed in claim 1, wherein $Z^1$ is $CR^1$ or C, where a $Z^1$ group is C when a Y group is bonded thereto.

6. The compound as claimed in claim 1, wherein $Ar^1$ is the same or different at each instance and is a divalent group derived from the base skeletons of benzene, biphenyl, terphenyl, naphthalene, and fluorene, where the divalent group may be substituted by one or more $R^2$ radicals.

7. The compound as claimed in claim 1, wherein $R^1$, $R^2$, and $R^4$ are the same or different at each instance and are selected from H, D, F, CN, $Si(R^5)_3$, $N(R^5)_2$, straight-chain alkyl or alkoxy groups having 1 to 20 carbon atoms, branched or cyclic alkyl or alkoxy groups having 3 to 20 carbon atoms, aromatic ring systems having 6 to 40 aromatic ring atoms and heteroaromatic ring systems having 5 to 40 aromatic ring atoms; where the alkyl or alkoxy groups mentioned, the aromatic ring systems mentioned and the heteroaromatic ring systems mentioned may each be substituted by one or more $R^5$ radicals; and where one or more $CH_2$ groups in the alkyl or alkoxy groups mentioned may be replaced by —C≡C—, —$R^5$C=$CR^5$—, $Si(R^5)_2$, C=O, C=$NR^5$, —$NR^5$—, —O—, —S—, —C(=O)O— or —C(=O)$NR^5$—.

8. The compound as claimed in claim 1, wherein $R^5$ is the same or different at each instance and is selected from H, D, F, CN, $Si(R^6)_3$, $N(R^6)_2$, straight-chain alkyl or alkoxy groups having 1 to 20 carbon atoms, branched or cyclic alkyl or alkoxy groups having 3 to 20 carbon atoms, aromatic ring systems having 6 to 40 aromatic ring atoms and heteroaromatic ring systems having 5 to 40 aromatic ring atoms; where the alkyl and alkoxy groups mentioned, the aromatic ring systems mentioned and the heteroaromatic ring systems mentioned may each be substituted by one or more $R^6$ radicals; and where one or more $CH_2$ groups in the alkyl or alkoxy groups mentioned may be replaced by —C≡C—, —$R^6$C=$CR^6$—, $Si(R^6)_2$, C=O, C=$NR^6$, —$NR^6$—, —O—, —S—, —C(=O)O— or —C(=O)$NR^6$—.

9. The compound as claimed in claim 1, wherein $R^6$ is H.

10. The compound as claimed in claim 1, wherein m and n at each instance are 0.

11. The compound as claimed in claim 1, wherein formula (I) conforms to one of the following formulae Formula (I-1)

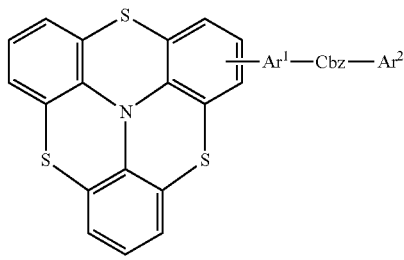

Formula (I-2)

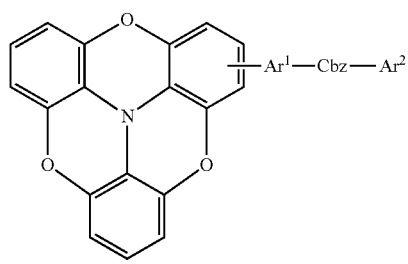

Formula (I-3)

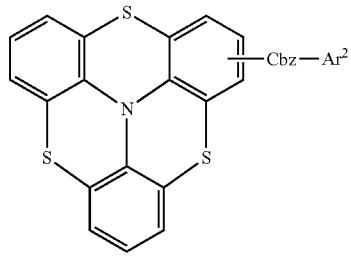

Formula (I-4)

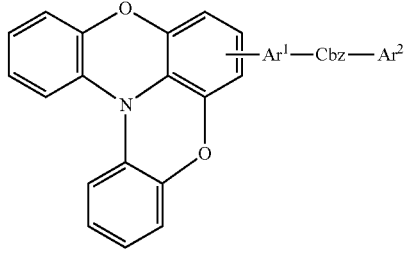

Formula (I-5)

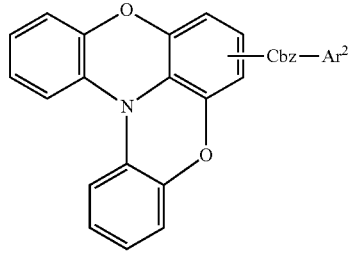

Formula (I-6)

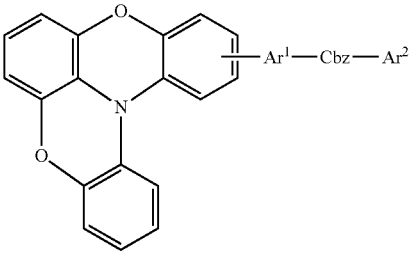

Formula (I-7)

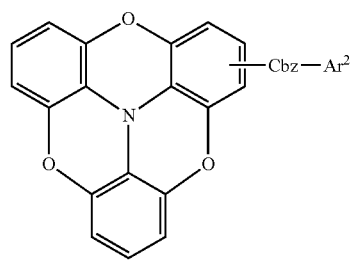

Formula (I-8)
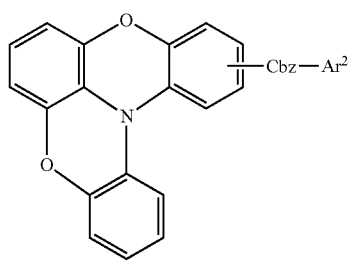
Formula (I-9)
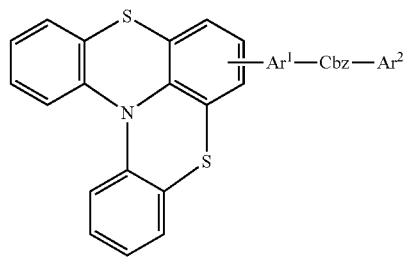
Formula (I-10)
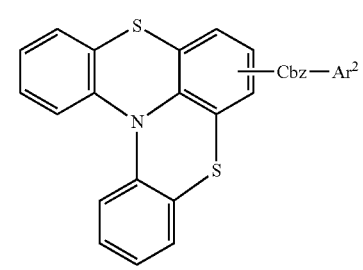
Formula (I-11)
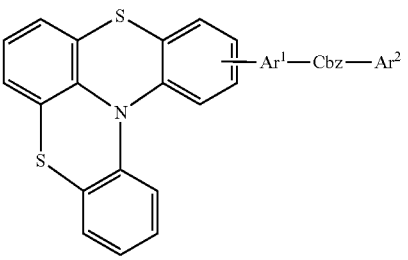
Formula (I-12)
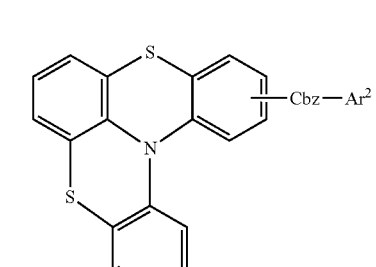
Formula (I-13)
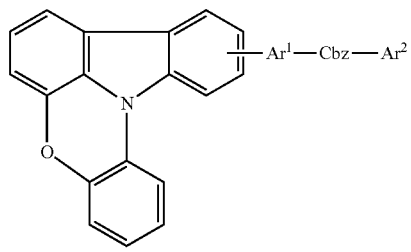
Formula (I-14)
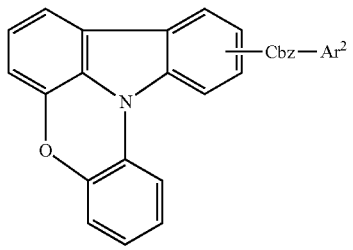
Formula (I-15)
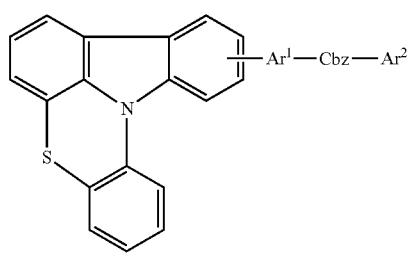
Formula (I-16)
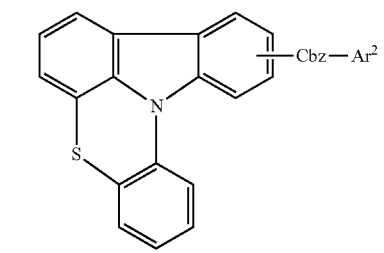
Formula (I-17)
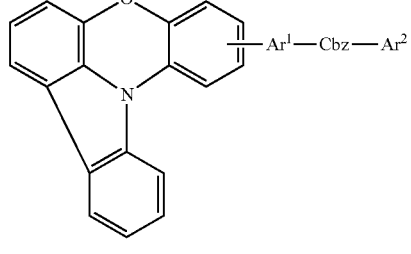
Formula (I-18)
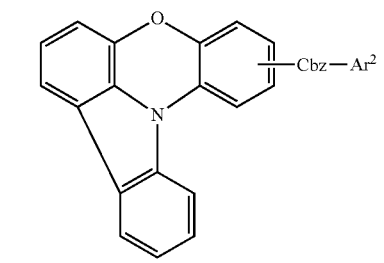

193
-continued

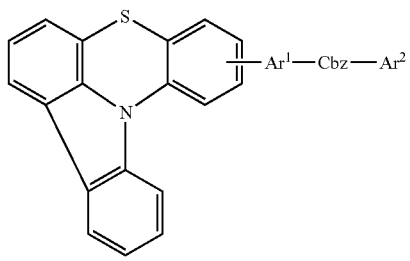

Formula (I-19)

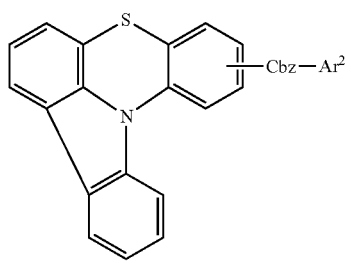

Formula (I-20)

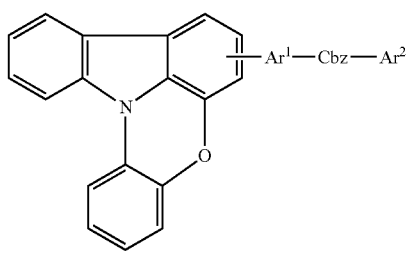

Formula (I-21)

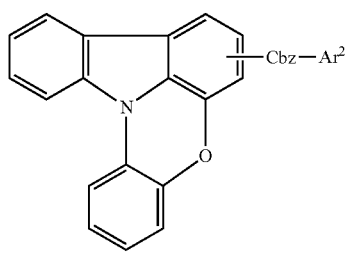

Formula (I-22)

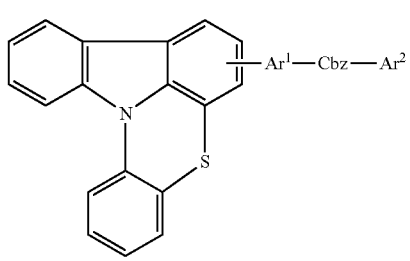

Formula (I-23)

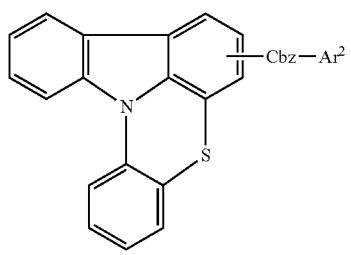

Formula (I-24)

where the variables that occur are as defined in claim 1, and the formulae may be substituted at each of the positions shown as unsubstituted on the aromatic six-membered rings by an $R^1$ group.

12. A process for preparing a compound as claimed in claim 1, characterized in that, in a first step, a triphenylamine compound substituted by a reactive group on one of the phenyl groups is prepared, where the bridges between the phenyl groups are selected from single bond, O and S, and where at least 2 bridges are present, and in that, in a further step, a carbazole group is introduced into the compound via a transition metal-catalyzed coupling reaction.

13. An oligomer, polymer or dendrimer containing one or more compounds of formula (I) as claimed in claim 1, wherein the bond(s) to the polymer, oligomer or dendrimer may be localized at any desired positions substituted by $R^1$, $R^2$, $R^3$ or $R^4$ in formula (I).

14. A formulation comprising at least one compound as claimed in claim 1, and at least one solvent.

15. An electronic device comprising at least one compound as claimed in claim 1.

16. The electronic device as claimed in claim 15, wherein the device is an organic electroluminescent device comprising anode, cathode and at least one emitting layer, where it is at least one organic layer of the device, which is an emitting layer, an electron transport layer or a hole blocker layer, that comprises the at least one compound.

17. The compound as claimed in claim 1, wherein $Ar^e$ is selected from pyridine, pyrimidine, pyridazine, pyrazine, triazine, benzimidazole, quinoline, quinazoline, benzo[h]quinazoline, phenanthroline, phenanthridine, diazaphenanthrene, and acridine that may each be substituted by one or more $R^4$ radicals.

18. A compound of formula (I)

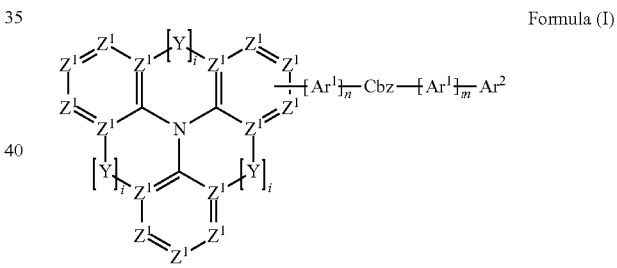

Formula (I)

where the variables that occur are as follows:

Y is the same or different at each instance and is selected from a single bond, O and S, where there is at least one Y group selected from O and S;

$Z^1$ is the same or different at each instance and is $CR^1$, N or C, where a $Z^1$ group is C in the specific case when a Y group is bonded to it;

$Ar^1$ is the same or different at each instance and is an aromatic ring system which has 6 to 24 aromatic ring atoms and may be substituted by one or more $R^2$ radicals;

Cbz is a divalent group of the formula (Cbz)

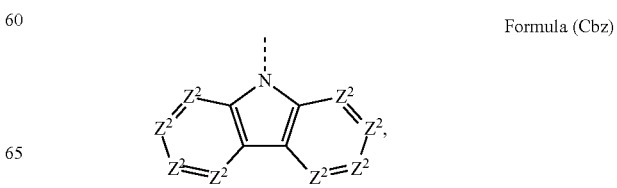

Formula (Cbz)

substituted at each of its unoccupied positions by an $R^3$ radical, where one of the two bonds of the divalent group to the rest of the compound is the dotted bond on the nitrogen atom of the formula (Cbz), where the second of these two bonds may be at any unoccupied position in the group, and where $Z^2$ is the same or different at each instance and is selected from C and N;

$Ar^2$ is selected from triazine and quinazoline that may each be substituted by one or more $R^4$ radicals;

$R^1$, $R^2$, $R^4$ are the same or different at each instance and are selected from H, D, F, $C(=O)R^5$, CN, $Si(R^5)_3$, $N(R^5)_2$, $P(=O)(R^5)_2$, $OR^5$, $S(=O)R^5$, $S(=O)_2R^5$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$ or $R^2$ or $R^3$ or $R^4$ radicals may be joined to one another and may form a ring; where the alkyl, alkoxy, alkenyl and alkynyl groups mentioned and the aromatic ring systems and heteroaromatic ring systems mentioned may each be substituted by one or more $R^5$ radicals; and where one or more $CH_2$ groups in the alkyl, alkoxy, alkenyl and alkynyl groups mentioned may be replaced by $-R^5C=CR^5-$, $-C\equiv C-$, $Si(R^5)_2$, $C=O$, $C=NR^5$, $-C(=O)O-$, $-C(=O)NR^5-$, $NR^5$, $P(=O)(R^5)$, $-O-$, $-S-$, SO, $SO_2$;

$R^3$ are the same or different at each instance and are selected from H, D, F, $C(=O)R^5$, CN, $Si(R^5)_3$, $N(R^5)_2$, $P(=O)(R^5)_2$, $OR^5$, $S(=O)R^5$, $S(=O)_2R^5$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, and aromatic ring systems having 6 to 40 aromatic ring atoms; where two or more or $R^3$ or $R^4$ radicals may be joined to one another and may form a ring; where the alkyl, alkoxy, alkenyl and alkynyl groups mentioned and the aromatic ring systems; and where one or more $CH_2$ groups in the alkyl, alkoxy, alkenyl and alkynyl groups mentioned may be replaced by $-R^5C=CR^5-$, $-C\equiv C-$, $Si(R^5)_2$, $C=O$, $C=NR^5$, $-C(=O)O-$, $-C(=O)NR^5-$, $NR^5$, $P(=O)(R^5)$, $-O-$, $-S-$, SO, $SO_2$;

$R^5$ is the same or different at each instance and is selected from H, D, F, $C(=O)R^6$, CN, $Si(R^6)_3$, $N(R^6)_2$, $P(=O)(R^6)_2$, $OR^6$, $S(=O)R^6$, $S(=O)_2R^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^5$ radicals may be joined to one another and may form a ring; where the alkyl, alkoxy, alkenyl and alkynyl groups mentioned and the aromatic ring systems and heteroaromatic ring systems mentioned may each be substituted by one or more $R^6$ radicals; and where one or more $CH_2$ groups in the alkyl, alkoxy, alkenyl and alkynyl groups mentioned may be replaced by $-R^6C=CR^6-$, $-C\equiv C-$, $Si(R^6)_2$, $C=O$, $C=NR^6$, $-C(=O)O-$, $-C(=O)NR^6-$, $NR^6$, $P(=O)(R^6)$, $-O-$, $-S-$, SO, or $SO_2$;

$R^6$ is the same or different at each instance and is selected from H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^6$ radicals may be joined to one another and may form a ring; and where the alkyl, alkoxy, alkenyl and alkynyl groups, aromatic ring systems and heteroaromatic ring systems mentioned may be substituted by F or CN;

is the same or different at each instance and is 0 or 1, where at least two indices i in formula (I) are 1, and where the Y group in question is absent when the corresponding index i=0;

n is 0, 1, 2, 3 or 4; and m is 0, 1, 2, 3 or 4.

\* \* \* \* \*